United States Patent
Bian et al.

(10) Patent No.: US 12,172,992 B2
(45) Date of Patent: Dec. 24, 2024

(54) PYRIMIDINES FOR DEGRADING BRUTON'S TYROSINE KINASE

(71) Applicant: AbbVie Inc., North Chicago, IL (US)

(72) Inventors: Zhiguo Bian, Lake Bluff, IL (US); Jason P. Burke, Libertyville, IL (US); Zhaozhong J. Jia, San Mateo, CA (US); Xingyu Jiang, San Jose, CA (US); Matthew H. Katcher, Evanston, IL (US); Venkat Reddy Mali, Cupertino, CA (US); Violeta L. Marin, Deerfield, IL (US); Elizabeth L. Noey, Franklin, WI (US); Alexey A. Rivkin, San Francisco, CA (US); Kevin R. Woller, Antioch, IL (US); Ashley M. Adams, Chesterbrook, PA (US); Shahab Mortezaei, Santa Clara, CA (US); Joshua N. Payette, Lafayette, CO (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 18/187,489

(22) Filed: Mar. 21, 2023

(65) Prior Publication Data
US 2024/0109877 A1 Apr. 4, 2024

Related U.S. Application Data

(60) Provisional application No. 63/322,505, filed on Mar. 22, 2022.

(51) Int. Cl.
C07D 413/14 (2006.01)
A61P 35/02 (2006.01)

(52) U.S. Cl.
CPC ............ C07D 413/14 (2013.01); A61P 35/02 (2018.01)

(58) Field of Classification Search
CPC ............................. C07D 413/14; A61P 35/02
See application file for complete search history.

(56) References Cited

U.S. PATENT DOCUMENTS

| | | |
|---|---|---|
| 5,578,550 A | 11/1996 | Buck |
| 5,593,946 A | 1/1997 | Buck |
| 5,707,935 A | 1/1998 | Buck |
| 6,998,233 B2 | 2/2006 | Wells et al. |
| 7,214,487 B2 | 5/2007 | Erlanson et al. |
| 7,988,944 B2 | 8/2011 | Ishiyama et al. |
| 8,580,829 B2 | 11/2013 | Bartolozzi et al. |
| 8,658,661 B2 | 2/2014 | Bartolozzi et al. |
| 8,975,254 B2 | 3/2015 | Wohlfahrt et al. |
| 9,157,875 B2 | 10/2015 | Warner et al. |
| 9,248,187 B2 | 2/2016 | Bylock |
| 9,605,070 B2 | 3/2017 | Sabatos-Peyton et al. |
| 9,657,003 B2 | 5/2017 | Wohlfahrt et al. |
| 9,684,000 B2 | 6/2017 | Arron et al. |
| 9,694,084 B2 | 7/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 9,884,913 B2 | 2/2018 | Sabatos-Peyton et al. |
| 9,908,936 B2 | 3/2018 | Triebel et al. |
| 9,995,755 B2 | 6/2018 | Arron et al. |
| 10,023,615 B2 | 7/2018 | Bonny |
| 10,118,901 B2 | 11/2018 | Chen et al. |
| 10,118,933 B2 | 11/2018 | Wohlfahrt et al. |
| 10,189,829 B2 | 1/2019 | Hopkins et al. |
| 10,227,341 B2 | 3/2019 | Hopkins et al. |
| 10,253,023 B2 | 4/2019 | Gaillard et al. |

(Continued)

FOREIGN PATENT DOCUMENTS

| | | |
|---|---|---|
| EP | 1441228 B1 | 6/2006 |
| EP | 1337853 B1 | 1/2009 |

(Continued)

OTHER PUBLICATIONS

Wang, Y., "Degradation of proteins by PROTACs and other strategies." Acta Pharmaceutica Sinica B 10.2 (2020): 207-238.*
Altan A., et al., "Free and Liposome form of Gallic Acid Improves Calvarial Bone Wound Healing in Wistar Rats," Asian Pacific Journal of Tropical Biomedicine, 2020, vol. 10(4), pp. 156-163.
Baumann U., et al.,"HAX1 Regulates Cell Surface Expression and Activity of CXCR4 in B-Cell Lymphoma," Oncology Research and Treatment, 2016, vol. 39(3), p. 219.
BD Biosciences, Cat No. 611117.
BD Biosciences, cat No. 624008.

(Continued)

*Primary Examiner* — John M Mauro
(74) *Attorney, Agent, or Firm* — Allisyn Monteleone

(57) ABSTRACT

The present invention provides for compounds of formula (I)

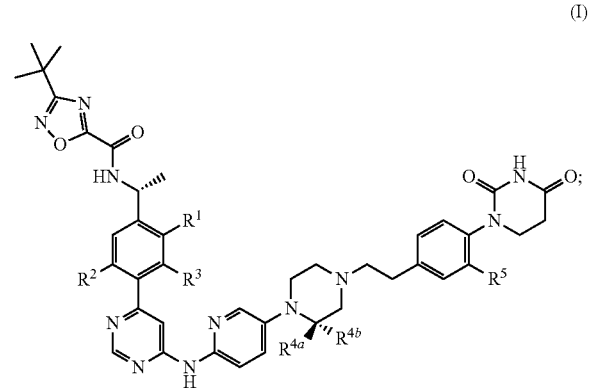

wherein $R^1$, $R^2$, $R^3$, $R^{4a}$, $R^{4b}$, and $R^5$, are as defined herein, and pharmaceutically acceptable salts thereof, that are useful as agents in the treatment of CLL.

3 Claims, 1 Drawing Sheet

(56) References Cited

U.S. PATENT DOCUMENTS

| | | |
|---|---|---|
| 10,266,528 B2 | 4/2019 | Caldwell |
| 10,336,744 B2 | 7/2019 | Harling et al. |
| 10,472,419 B2 | 11/2019 | Sabatos-Peyton et al. |
| 10,711,013 B2 | 7/2020 | Wohlfahrt et al. |
| 10,711,060 B2 | 7/2020 | Triebel et al. |
| 10,842,878 B2 | 11/2020 | Gray et al. |
| 10,849,980 B2 | 12/2020 | Bradner et al. |
| 10,899,753 B2 | 1/2021 | Hopkins et al. |
| 10,925,967 B2 | 2/2021 | Gray et al. |
| 10,961,237 B2 | 3/2021 | Hopkins et al. |
| 10,981,990 B2 | 4/2021 | Sabatos-Peyton et al. |
| 11,028,088 B2 | 6/2021 | Crews et al. |
| 11,046,713 B2 | 6/2021 | Wohlfahrt et al. |
| 11,098,041 B2 | 8/2021 | Gaillard et al. |
| 11,117,889 B1 | 9/2021 | Mainolfi et al. |
| 11,155,561 B2 | 10/2021 | Shu |
| 11,155,620 B2 | 10/2021 | Sabatos-Peyton et al. |
| 11,174,252 B2 | 11/2021 | Pham et al. |
| 11,226,341 B2 | 1/2022 | Arron et al. |
| 11,242,344 B2 | 2/2022 | Blaquiere et al. |
| 11,352,350 B2 | 6/2022 | Mainolfi et al. |
| 11,427,577 B2 | 8/2022 | Hopkins et al. |
| 11,433,053 B2 | 9/2022 | Wu et al. |
| 11,479,556 B1 | 10/2022 | Robbins et al. |
| 11,541,056 B2 | 1/2023 | Arista et al. |
| 11,542,251 B2 | 1/2023 | Gray et al. |
| 11,583,586 B2 | 2/2023 | Bradner et al. |
| 2004/0043426 A1 | 3/2004 | Wells et al. |
| 2008/0220441 A1 | 9/2008 | Birnbaum et al. |
| 2012/0142584 A1 | 6/2012 | Bonny |
| 2012/0156194 A1 | 6/2012 | Arron et al. |
| 2015/0259420 A1 | 9/2015 | Triebel et al. |
| 2015/0284394 A1 | 10/2015 | Bhagirath et al. |
| 2017/0037004 A1 | 2/2017 | Crew et al. |
| 2018/0085465 A1 | 3/2018 | Bradner et al. |
| 2018/0140571 A1 | 5/2018 | Bacha et al. |
| 2018/0194762 A1 | 7/2018 | Atallah et al. |
| 2019/0152946 A1 | 5/2019 | Harling et al. |
| 2019/0210996 A1 | 7/2019 | Harling et al. |
| 2019/0263798 A1 | 8/2019 | Harling et al. |
| 2019/0337988 A1 | 11/2019 | Bonny |
| 2020/0121684 A1 | 4/2020 | Crews et al. |
| 2021/0002295 A1 | 1/2021 | Gray et al. |
| 2021/0009687 A1 | 1/2021 | Triebel et al. |
| 2021/0030832 A1 | 2/2021 | Gray et al. |
| 2021/0038605 A1 | 2/2021 | Jin et al. |
| 2021/0100908 A1 | 4/2021 | Gray et al. |
| 2021/0276996 A1 | 9/2021 | Gray et al. |
| 2021/0363148 A1 | 11/2021 | Shu |
| 2022/0025050 A1 | 1/2022 | Poirier et al. |
| 2022/0056135 A1 | 2/2022 | Poirier et al. |
| 2022/0081430 A1 | 3/2022 | Wacker et al. |
| 2022/0143195 A1 | 5/2022 | Kato et al. |
| 2022/0162163 A1 | 5/2022 | Berlin et al. |
| 2022/0185883 A1 | 6/2022 | Sabatos-Peyton et al. |
| 2022/0259194 A1 | 8/2022 | Hopkins et al. |
| 2022/0324854 A1 | 10/2022 | Mainolfi et al. |
| 2022/0372017 A1 | 11/2022 | Gray et al. |
| 2022/0389004 A1 | 12/2022 | Caldwell et al. |
| 2023/0025892 A1 | 1/2023 | Marx et al. |
| 2023/0029378 A1 | 1/2023 | Robbins et al. |
| 2023/0062022 A1 | 3/2023 | Pham et al. |
| 2023/0071889 A1 | 3/2023 | Poirier et al. |
| 2023/0121818 A1 | 4/2023 | Ma et al. |
| 2023/0147490 A1 | 5/2023 | Hopkins et al. |
| 2023/0148436 A2 | 5/2023 | Jin et al. |
| 2023/0167118 A1 | 6/2023 | Wang et al. |

FOREIGN PATENT DOCUMENTS

| | | |
|---|---|---|
| EP | 2084519 B1 | 8/2012 |
| EP | 2511844 B1 | 8/2015 |
| EP | 3645001 A1 | 5/2020 |
| EP | 3458101 B1 | 12/2020 |
| EP | 4192587 A1 | 6/2023 |
| EP | 4192812 A1 | 6/2023 |
| EP | 4192813 A1 | 6/2023 |
| EP | 4192814 A1 | 6/2023 |
| JP | 3402153 B2 | 4/2003 |
| KR | 1582834 B1 | 1/2016 |
| KR | 1635848 B1 | 7/2016 |
| WO | 0242773 B1 | 12/2002 |
| WO | 2008127291 A2 | 10/2008 |
| WO | 2015138920 A1 | 9/2015 |
| WO | 2015154064 A3 | 1/2016 |
| WO | 2017201449 A1 | 11/2017 |
| WO | 2019006393 A1 | 1/2019 |
| WO | 2019084030 A1 | 5/2019 |
| WO | 2019183523 A1 | 9/2019 |
| WO | 2020165374 A1 | 8/2020 |
| WO | 2020206035 A1 | 10/2020 |
| WO | 2020252397 A1 | 12/2020 |
| WO | 2021180103 A1 | 9/2021 |
| WO | 2022032019 A1 | 2/2022 |
| WO | 2022143856 A1 | 7/2022 |
| WO | 2022235945 A1 | 11/2022 |
| WO | 2022268052 A1 | 12/2022 |
| WO | 2023275333 A1 | 1/2023 |
| WO | 2023275336 A1 | 1/2023 |
| WO | 2023275337 A1 | 1/2023 |
| WO | 2023066350 A1 | 4/2023 |
| WO | 2023086521 A1 | 5/2023 |
| WO | 2023104155 A1 | 6/2023 |
| WO | 2023110138 A1 | 6/2023 |
| WO | 2023125907 A1 | 7/2023 |
| WO | 2023125908 A1 | 7/2023 |

OTHER PUBLICATIONS

Blackburn T., et al., "Current Trends in Drug Discovery—Young Scientists and Tomorrow's Medicines: Highlights from a Joint Society for Medicines Research and British Pharmacological Society Meeting," Drugs of the Future, 2018, vol. 43(8), pp. 627-633.
Bofill X., "NME Digest," Drugs of the Future, 2020, vol. 45(4), pp. 267-272.
Buhimschi A.D., "Targeting the C481S Ibrutinib-Resistance Mutation in Bruton's Tyrosine Kinase Using PROTAC-Mediated Degradation," Biochemistry, 2018, vol. 57(26), pp. 3564-3575.
CAS 161265-03-8.
CAS 2151915-22-7.
CAS 52409-22-0.
Cell Signaling Technology, Cat No. 8547CF.
Cell Signaling Technology, Cat No. 9803.
Chiara T., et al., "PQR309-Containing Combinations Show Synergistic Antilymphoma Activity," Molecular Cancer Therapeutics, 2018, vol. 17(1), Meeting Info: AACR-NCI-EORTC International Conference: Molecular Targets and Cancer Therapeutics 2017. Philadelphia, PA, United States. pp. 1538-8514.
Costar, Cat No. 3894.
Dobrovolsky D., et al., "Bruton Tyrosine Kinase Degradation as a Therapeutic Strategy for Cancer," Blood, 2019, vol. 133(9), pp. 952-961.
Donovan K.A., et al., "Mapping the Degradable Kinome Provides a Resource for Expedited Degrader Development" Cell, 2020, vol. 183(6), pp. 1714-1731.
Extended European Search Report for Application No. EP23162731, mailed on May 8, 2023, 7 pages.
Fathipour Y., et al., "Increased Food Utilization Indices and Decreased Proteolytic Activity in Helicoverpa Armigera Larvae Fed Sublethal Bacillus Thuringiensis-treated Diet," Physiological Entomology, 2019, pp. 1-9.
Ferrer L.P., et al., "MYCN Repression of Lifeguard/FAIM2 Enhances Neuroblastoma Aggressiveness," Cell Death Disease, 2014, vol. 5(9), pp. e1401.
Figueroa S.J., et al., "Design, Synthesis and Biological Evaluation of Proteolysis Targeting Chimeras (PROTACs) as a BTK Degraders with Improved Pharmacokinetic Properties" Bioorganic Medicinal Chemistry Letters, Feb. 1, 2020, vol. 30(3), 29 pages.
Fiskus W., et al., "BET Protein Antagonist-Based Therapy of Novel Models of Richter Transformation-Diffuse Large B-Cell Lymphoma

(56) References Cited

OTHER PUBLICATIONS (RT-DLBCL)," 605 Molecular Pharmacology, Drug Resistance—Lymphoid and Other Diseases, 2020, vol. 136(Suppl. 1), pp. 17-18.
Gabizon R., et al., "Correction to Efficient Targeted Degradation via Reversible and Irreversible Covalent PROTACs," Journal of the American Chemical Society, 2020, vol. 142(25), 1 Pages.
Gabizon R., et al., "Efficient targeted degradation via reversible and irreversible covalent PROTACs" ChemRxiv, 2020, pp. 1-20.
George B., et al., "Ibrutinib Resistance Mechanisms and Treatment Strategies for B-Cell lymphomas," Review Cancers (Basel). 2020, vol. 12(5), 31 Pages.
Groppe J.C., "Induced Degradation of Protein Kinases by Bifunctional Small Molecules: a Next-generation Strategy," Expert Opinion on Drug Discovery, 2019, vol. 14(12), pp. 1-17.
Hanan E.J., et al., "Monomeric Targeted Protein Degraders," Journal of Medicinal Chemistry, 2020, vol. 63(20), pp. 11330-11361.
Horwood N.J., et al., "Bruton's Tyrosine Kinase Is Required for Lipopolysaccharide-induced Tumor Necrosis Factor a Production," The Journal of Experimental Medicine, Jun. 2003, vol. 197 (12), pp. 1603-1611.
Huang H.T., "A Chemoproteomic Approach to Query the Degradable Kinome Using a Multi-kinase Degrader," Cell Chemical Biology, 2018, vol. 25(1), pp. 88-99.
International Search Report and Written Opinion for Application No. PCT/US2023/064775, mailed on May 3, 2023, 11 pages.
Iwaki S., et al., "Btk Plays a Crucial Role in the Amplification of FceRI-mediated Mast Cell Activation by Kit," Journal of Biological Chemistry, Dec. 2005, vol. 280 (48), pp. 40261-40270.
Jain N., et al., "Targetable Genetic Alterations of TCF4 ( E2-2) Drive Immunoglobulin Expression in Diffuse Large B Cell Lymphoma," Science Translational Medicine, 2019, vol. 11, pp. 1-14.
Jefferies C.A., et al., "Bruton's Tyrosine Kinase is a Toll/interleukin-1 Receptor Domain-binding Protein that Participates in Nuclear Factor kappaB Activation by Toll-like Receptor 4," Journal of Biological Chemistry, Jul. 2003, vol. 278 (28), pp. 26258-26264.
Jones L.H., "Small-Molecule Kinase Downregulators," Cell Chemical Biology, 2018 , vol. 25(1), pp. 30-35.
Karkhanis V., et al., "Efficacy of Targeted Therapy in Novel Pre-Clinical in Vitro and In Vivo Models of Richter Transformation-Diffuse Large B-Cell Lymphoma (RT-DLBCL)," Blood, 2019, vol. 134, pp. 1-3.
Kelleher J.F., et al., "Abstract Lb-272: Kym-001, a First-in-class Oral IRAK4 Protein Degrader, Induces Tumor Regression in Xenograft Models of Myd88-mutant ABC DLBCL Alone and in Combination With BTK Inhibition," Cancer Research, 2019, vol. 79(13), pp. 1-3.
Krajcovicova S., et al., "Solid-phase Synthesis for Thalidomide-based Proteolysis-targeting Chimeras (PROTAC)," Chemical Communications, 2019, vol. 55(7), pp. 929-932.
Kupzig S., et al., "GAP1 Family Members Constitute Bifunctional Ras and Rap GTPase-Activating Proteins," The Journal of Biological Chemistry, 2006, vol. 281(15), pp. 9891-9900.
Kurosaki T., "Functional Dissection of BCR Signaling Pathways," Current Opinion in Immunology, Jun. 2000, vol. 12 (3), pp. 276-281.
Liu J., et al., "PROTACs: A Novel Strategy for Cancer Therapy," Seminars in Cancer Biology, 2020, vol. 67, Part 2, pp. 171-179.
Liu S., et al., "Targeted Selective Degradation of Bruton's Tyrosine Kinase by PROTACs," Medicinal Chemistry Research, 2020, vol. 29, pp. 802-808.
Li-Wen X., et al., "Triazol: A Privileged Scaffold for Proteolysis Targeting Chimeras," Future Medicinal Chemistry, 2019, vol. 11(22), pp. 1-19.
Lu X., et al., "Medicinal Chemistry Strategies for the Development of Kinase Inhibitors Targeting Point Mutations," Journal of Medicinal Chemistry, 2020, vol. 63(19), pp. 10726-1074.
Meso Scale Discovery, Cat No. L45XB-3.
Meso Scale Discovery, Cat No. R32AC-1.
Meso Scale Discovery, R92TC-1.
MSD, cat No. L15SA-1.
MSD, cat No. R32AB-1.
MSD, cat No. R61TX-1.
MSD, cat No. R92TC-1.
MSD, cat No. R93BA-4.
Nonionic polyoxyethylene surfactant, ThermoFisher, cat No. 28324.
Pares S., et al., "European Federation of Medicinal Chemistry—XXV International Symposium on Medicinal Chemistry," Drugs of the Future, 2018, vol. 43(10), pp. 783-792.
Quek I.S., et al., "A Role for Bruton's Tyrosine Kinase (BTK) in Platelet Activation by Collagen," Current Biology, Oct. 1998, vol. 8 (20), pp. 1137-1140.
Rabbit polyclonal antibody, CST, cat No. 8547S, D3H5 clone.
Robbins D.W., et al., "Nx-2127, A Degrader of BTK and IMiD Neo Substrates, for the Treatment of B-Cell Malignancies," 605 Molecular Pharmacology, Drug Resistance—Lymphoid and Other Diseases, 2020, vol. 136(Suppl. 1), 3 Pages.
Roche, cat No. 04906837001.
Roche, cat No. 05892970001.
Schaeffer E.M., et al., "Tec Family Kinases in Lymphocyte Signaling and Function," Current Opinion in Immunology, Jun. 2000, vol. 12 (3), pp. 282-288.
Scheepstra M., et al., "Bivalent Ligands for Protein Degradation in Drug Discovery," Computational and Structural Biotechnology Journal, 2019, vol. 17, pp. 160-176.
Siriwardena S.U., et al., "Phosphorylation-Inducing Chimeric Small Molecules," Journal of American Chemical Society, 2020, vol. 142(33), pp. 14052-14057.
Smith C.E.,"Correcting Exon Skipping Splicing Defects in BTK RNA by Using Bifunctional Oligonucleotides," Molecular Therapy, 2016, vol. 24(1), pp. S231.
Sun B., et al., "BET Protein Proteolysis Targeting Chimera (PROTAC) Exerts Potent Lethal Activity Against Mantle Cell Lymphoma Cells," Leukemia, 2018, vol. 32(2), pp. 343-352.
Sun B., et al., "Preclinical Activity of Novel BET Protein Proteolysis Targeting Chimeras (BETP-PROTACs) and Their Combination with Venetoclax or CDK4/6 Inhibitor Against Human Mantle Cell Lymphoma (MCL) Cells," Blood, 2017, vol. 130(1), 59th Annual Meeting of the American Society of Hematology, pp. 1-2.
Sun B., "Novel BET Protein Proteolysis Targeting Chimeras (BETP-PROTACs) Exert Potent Single Agent and Synergistic Activity with Ibrutinib and Venetoclax Against Human Mantle Cell Lymphoma Cells," Blood, 2016, vol. 128 (22), pp. 1-3.
Sun X., et al., "A Chemical Approach for Global Protein Knockdown From Mice to Non-human Primates," Cell Discovery, 2019, vol. 5(1), pp. 1-13.
Sun X., et al., "PROTACs as Potential Therapeutic Agents for Cancer Drug Resistance," Biochemistry, 2020, vol. 59, pp. 240-249.
Sun X., et al., "PROTACs as Potential Therapeutic Agents for Cancer Drug Resistance," Biochemistry, 2020, vol. 59 (3), pp. 240-249.
Sun Y., et al., "PROTAC-induced BTK Degradation as a Novel Therapy for Mutated BTK C481S Induced Ibrutinib-Resistant B-cell Malignancies," Cell Research, 2018, vol. 28(7), pp. 779-781.
Tasso B., et al., "The Development of BTK Inhibitors: A Five-Year Update," Molecules : A Journal of Synthetic Chemistry and Natural Product Chemistry, 2021, vol. 26(23), pp. 1-31.
Thermofisher, Cat No. 23225.
Thermofisher, cat No. PR5442A.
Tinworth C.P., et al., "PROTAC-Mediated Degradation of Bruton's Tyrosine Kinase Is Inhibited by Covalent Binding," ACS Chemical Biology, 2019, vol. 14(3), pp. 342-347.
Toenjes S., et al., "Atropisomerism and PROTACs as Strategies Towards Increased Potency and Selectivity of Analogs of Common Kinase Inhibitors," Abstracts of Papers, ACS Fall, 2019, pp. 1-2.
Tong B., et al., "A Nimbolide-based Kinase Degrader Preferentially Degrades Oncogenic BCR-ABL," ACS Chemical Biology, 2020, vol. 15(7), pp. 1-20.
Vassilev A., et al., "Bruton's Tyrosine Kinase as an Inhibitor of the Fas/CD95 Death-inducing Signaling Complex," Journal of Biological Chemistry, Jan. 1999, vol. 274 (3), pp. 1646-1656.
Vetter M., et al., "Fluorescent Visualization of Src by Using Dasatinib-BODIPY," Chembiochem, 2014, vol. 15(9), pp. 1317-1324.

(56) References Cited

OTHER PUBLICATIONS

VWR, cat No. 10032-756.

Wan Y., et al., "Small-molecule PROTACs: Novel Agents for Cancer Therapy," Future Medicinal Chemistry, 2020, vol. 12(10), pp. 915-938.

Wang., et al., "Proteolysis Targeting Chimera(PROTAC): A Paradigm-Shifting Approach in Small Molecule Drug Discovery," Current Topics in Medicinal Chemistry, 2018, vol. 18(16), pp. 1354-1356.

Wang S., et al., "Progress on Bruton's Tyrosine Kinase Targeted Drugs," 2020, vol. 37(24), pp. 3063-3072.

Watt G.F., et al., "Targeted Protein Degradation in Vivo With Proteolysis Targeting Chimeras: Current Status and Future Considerations," Drug Discovery Today. Technologies, 2019, vol. 31, pp. 69-80.

Xue G., et al., "Protein Degradation Through Covalent Inhibitor-based PROTACs," Chemical Communications (Cambridge, England), 2020, vol. 56(10), pp. 1521-1524.

Xue G., "Light-Induced Protein Degradation with Photocaged PROTACs," Journal of the American Chemical Society, 2019, vol. 141(46), pp. 18370-18374.

Yonghui S., et al., "Degradation of Bruton's Tyrosine Kinase Mutants by PROTACs for Potential Treatment of Ibrutinib-resistant Non-hodgkin Lymphomas," Leukemia, 2019, vol. 33(8), pp. 1-6.

Zhao Q., et al., "Discovery of SIAIS178 as an Effective BCR-ABL Degrader by Recruiting Von Hippel-Lindau (VHL) E3 Ubiquitin Ligase," Journal of Medicinal Chemistry, 2019, vol. 62(20), pp. 9281-9298.

Zhou X., et al., "PROTAC: A Promising Technology for Cancer Treatment," European Journal of Medicinal Chemistry, 2020, vol. 203, 11 Pages.

Zorba A., et al., "Delineating the Role of Cooperativity in the Design of Potent PROTACs for BTK," Proceedings of the National Academy of Sciences of the United States of America, 2018, vol. 115(31), pp. E7285-E7292.

Hannah L., et al., "Investigating the impact of covalency on PROTAC-mediated degradation of BTK, "Abstracts of Papers, 255th ACS National Meeting & Exposition, 2018, pp. 18-22.

Sara M., et al., "Triple Degradation of BTK, IKZF1 and IKZF3 in B-Cell Malignancies. "Blood: 60th Annual Meeting of the American-Society-of-Hematology, 2018 vol. 132(1), pp. 1-3.

\* cited by examiner

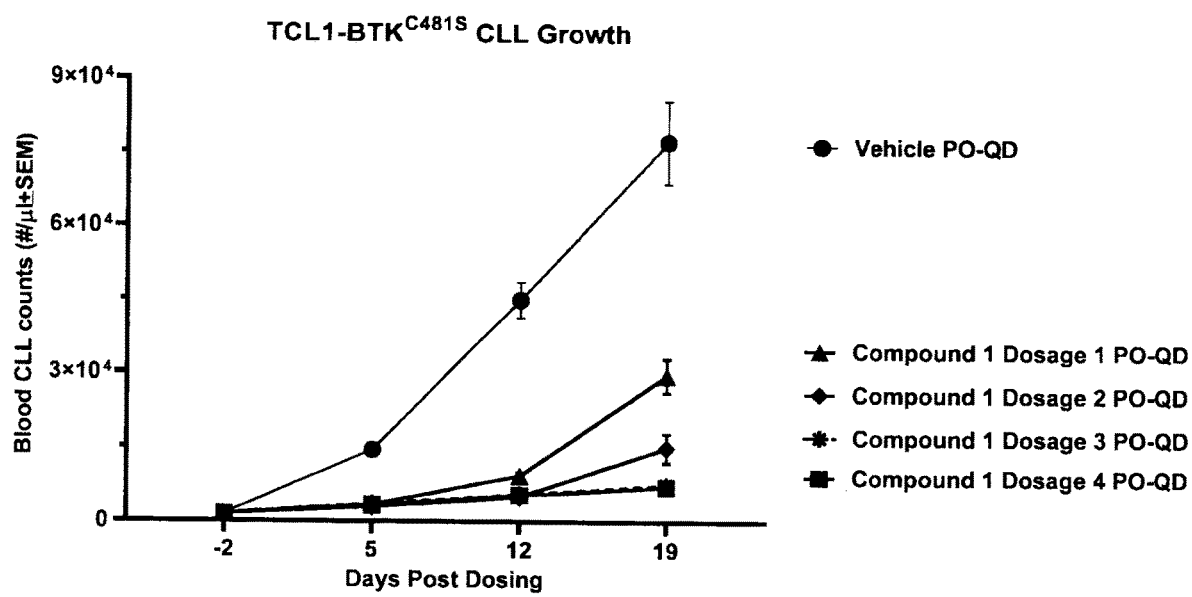

PYRIMIDINES FOR DEGRADING BRUTON'S TYROSINE KINASE

CROSS REFERENCE TO RELATED APPLICATIONS

This application is a non-provisional application which claims the benefit of, and priority to, U.S. Provisional Application No. 63/322,505, filed on Mar. 22, 2022, the content of which is hereby incorporated by reference in its entirety.

BACKGROUND OF THE INVENTION

Bruton's tyrosine kinase (Btk) is a key signaling enzyme expressed in hematopoietic cell types. Btk plays an essential role in the B-cell signaling pathway linking cell surface B-cell receptor (BCR) stimulation to downstream intracellular responses. Btk is a key regulator of B-cell development, activation, signaling, and survival (Kurosaki, *Curr Op Imm*, 2000, 276-281; Schaeffer and Schwartzberg, *Curr Op Imm* 2000, 282-288). In addition, Btk plays a role in other hematopoietic cell signaling pathways, e.g., Toll like receptor (TLR) and cytokine receptor-mediated TNF-α production in macrophages, IgE receptor (FcepsilonRI) signaling in mast cells, inhibition of Fas/APO-1 apoptotic signaling in B-lineage lymphoid cells, and collagen-stimulated platelet aggregation. See, e.g., C. A. Jeffries, et al., (2003), *Journal of Biological Chemistry* 278:26258-26264; N. J. Horwood, et al., (2003), *The Journal of Experimental Medicine* 197: 1603-1611; Iwaki et al. (2005), *Journal of Biological Chemistry* 280(48):40261-40270; Vassilev et al. (1999), *Journal of Biological Chemistry* 274(3):1646-1656, and Quek et al. (1998), *Current Biology* 8(20):1137-1140. Currently, Btk inhibitors are being investigated. As an alternative to inhibition, proteolytic degradation of Btk may affect B cell function by not only blocking BCR signaling, but by reducing the presence of the Btk protein from the cell itself. Reduction of the Btk protein would reduce Btk kinase activity as well as reduce any protein interactions or scaffolding functions of Btk. Accordingly, there is a medical need to develop Btk degraders.

SUMMARY OF THE INVENTION

In certain embodiments, provided herein are compounds that induce the proteolytic degradation of Btk via a ubiquitin proteolysis pathway.

In certain embodiments, compounds of formula (I) are provided:

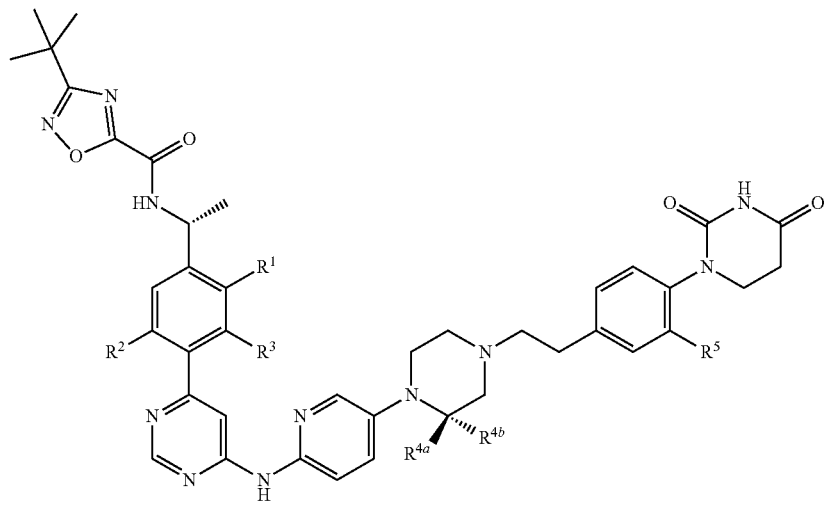

(I)

wherein
$R^1$ is selected from the group consisting of hydrogen, $C_1$-$C_3$ alkyl, CN, $C_1$-$C_3$ haloalkyl, halo, $CH_2OCH_3$, $CH_2OH$, and $CH_2CN$;
$R^2$ and $R^3$ are each independently selected from the group consisting of hydrogen and halo;
$R^{4a}$ and $R^{4b}$ are each independently selected from the group consisting of hydrogen, $C_1$-$C_3$ alkyl, and $CH_2OCH_3$; and
$R^5$ is selected from the group consisting of hydrogen, halo, and $C_1$-$C_3$ alkyl; or a pharmaceutically acceptable salt thereof.

In certain embodiments, $R^1$ is selected from the group consisting of hydrogen, $C_1$-$C_3$ alkyl, CN (cyano), $C_1$-$C_3$ haloalkyl, halo, $CH_2OCH_3$; $CH_2OH$; and $CH_2CN$; or a pharmaceutically acceptable salt thereof. In certain embodiments, $R^1$ is $C_1$-$C_3$ alkyl, or a pharmaceutically acceptable salt thereof. In certain embodiments, $R^1$ is methyl, or a pharmaceutically acceptable salt thereof. In certain embodiments, $R^1$ is hydrogen, or a pharmaceutically acceptable salt thereof. In certain embodiments, $R^1$ is CN, or a pharmaceutically acceptable salt thereof. In certain embodiments, $R^1$ is $C_1$-$C_3$ haloalkyl, or a pharmaceutically acceptable salt thereof. In certain embodiments, $R^1$ is $CF_3$, or a pharmaceutically acceptable salt thereof. In certain embodiments, $R^1$ is halo, or a pharmaceutically acceptable salt thereof. In certain embodiments, $R^1$ is Cl, or a pharmaceutically acceptable salt thereof. In certain embodiments, $R^1$ is F, or a pharmaceutically acceptable salt thereof. In certain embodiments, $R^1$ is $CH_2OCH_3$, or a pharmaceutically acceptable salt thereof. In certain embodiments, $R^1$ is $CH_2OH$ or a pharmaceutically acceptable salt thereof. In certain embodiments, $R^1$ is $CH_2CN$, or a pharmaceutically acceptable salt thereof.

In certain embodiments, $R^2$ is selected from the group consisting of hydrogen and halo, or a pharmaceutically acceptable salt thereof. In certain embodiments, $R^2$ is hydrogen, or a pharmaceutically acceptable salt thereof. In certain embodiments, $R^2$ is halo, or a pharmaceutically acceptable salt thereof. In certain embodiments, $R^2$ is F, or a pharmaceutically acceptable salt thereof.

In certain embodiments, $R^3$ is selected from the group consisting of hydrogen and halo, or a pharmaceutically acceptable salt thereof. In certain embodiments, $R^3$ is hydrogen, or a pharmaceutically acceptable salt thereof. In certain embodiments, $R^3$ is halo, or a pharmaceutically acceptable salt thereof. In certain embodiments, $R^3$ is F, or a pharmaceutically acceptable salt thereof.

In certain embodiments, $R^{4a}$ and $R^{4b}$ are each independently selected from the group consisting of hydrogen, $C_1$-$C_3$ alkyl, and $CH_2OCH_3$, or a pharmaceutically acceptable salt thereof. In certain embodiments, $R^{4a}$ is hydrogen and $R^{4b}$ is hydrogen, or a pharmaceutically acceptable salt thereof. In certain embodiments, $R^{4a}$ is hydrogen and $R^{4b}$ is methyl, or a pharmaceutically acceptable salt thereof. In certain embodiments, $R^{4a}$ is methyl and $R^{4b}$ is hydrogen, or a pharmaceutically acceptable salt thereof. In certain embodiments, $R^{4a}$ is hydrogen and $R^{4b}$ is ethyl, or a pharmaceutically acceptable salt thereof. In certain embodiments, $R^{4a}$ is ethyl and $R^{4b}$ is hydrogen, or a pharmaceutically acceptable salt thereof. In certain embodiments, $R^{4a}$ is methyl and $R^{4b}$ is methyl, or a pharmaceutically acceptable salt thereof. In certain embodiments, $R^{4a}$ is hydrogen and $R^{4b}$ is isopropyl, or a pharmaceutically acceptable salt thereof. In certain embodiments, $R^{4a}$ is isopropyl and $R^{4b}$ is hydrogen, or a pharmaceutically acceptable salt thereof. In certain embodiments, $R^{4a}$ is hydrogen and $R^{4b}$ is $CH_2OCH_3$, or a pharmaceutically acceptable salt thereof. In certain embodiments, $R^{4a}$ is $CH_2OCH_3$ and $R^{4b}$ is hydrogen, or a pharmaceutically acceptable salt thereof.

In certain embodiments, $R^5$ is selected from the group consisting of hydrogen, halo, and $C_1$-$C_3$ alkyl, or a pharmaceutically acceptable salt thereof. In certain embodiments, $R^5$ is hydrogen, or a pharmaceutically acceptable salt thereof. In certain embodiments, $R^5$ is halo, or a pharmaceutically acceptable salt thereof. In certain embodiments, $R^5$ is F, or a pharmaceutically acceptable salt thereof. In certain embodiments, $R^5$ is Cl, or a pharmaceutically acceptable salt thereof. In certain embodiments, $R^5$ is methyl, or a pharmaceutically acceptable salt thereof.

In certain embodiments, $R^1$ is methyl and $R^2$ is hydrogen, or a pharmaceutically acceptable salt thereof. In certain embodiments, $R^1$ is methyl, $R^2$ is hydrogen, and $R^3$ is hydrogen, or a pharmaceutically acceptable salt thereof. In certain embodiments, $R^1$ is methyl, $R^2$ is hydrogen, $R^3$ is hydrogen, $R^{4a}$ is hydrogen, and $R^{4b}$ is methyl, or a pharmaceutically acceptable salt thereof. In certain embodiments, $R^1$ is methyl, $R^2$ is hydrogen, $R^3$ is hydrogen, and $R^5$ is hydrogen, or a pharmaceutically acceptable salt thereof. In certain embodiments, $R^1$ is methyl, $R^{4a}$ is hydrogen and $R^{4b}$ is methyl, or a pharmaceutically acceptable salt thereof. In certain embodiments, $R^2$ is hydrogen, $R^{4a}$ is hydrogen and $R^{4b}$ is methyl, or a pharmaceutically acceptable salt thereof. In certain embodiments, $R^3$ is hydrogen, $R^{4a}$ is hydrogen, and $R^{4b}$ is methyl, or a pharmaceutically acceptable salt thereof.

In certain embodiments, $R^5$ is hydrogen, $R^{4a}$ is hydrogen, and $R^{4b}$ is methyl, or a pharmaceutically acceptable salt thereof. In certain embodiments, $R^5$ is hydrogen, $R^{4a}$ is hydrogen, $R^{4b}$ is methyl, and $R^3$ is hydrogen, or a pharmaceutically acceptable salt thereof. In certain embodiments, $R^5$ is hydrogen, $R^{4a}$ is hydrogen, $R^{4b}$ is methyl, and $R^3$ is hydrogen and $R^2$ is hydrogen, or a pharmaceutically acceptable salt thereof. In certain embodiments, $R^5$ is hydrogen, $R^{4a}$ is hydrogen, $R^{4b}$ is methyl, $R^3$ is hydrogen, and $R^1$ is methyl, or a pharmaceutically acceptable salt thereof.

In certain embodiments, $R^1$ is methyl and $R^3$ is halo, or a pharmaceutically acceptable salt thereof. In certain embodiments, $R^1$ is methyl and $R^3$ is F, or a pharmaceutically acceptable salt thereof. In certain embodiments, $R^1$ is methyl and $R^2$ is halo, or a pharmaceutically acceptable salt thereof. In certain embodiments, $R^1$ is methyl and $R^2$ is F, or a pharmaceutically acceptable salt thereof.

In certain embodiments, $R^5$ is halo, $R^{4a}$ is hydrogen, and $R^{4b}$ is methyl, or a pharmaceutically acceptable salt thereof. In certain embodiments, $R^5$ is F, $R^{4a}$ is hydrogen, and $R^{4b}$ is methyl, or a pharmaceutically acceptable salt thereof. In certain embodiments, $R^5$ is halo, $R^{4a}$ is methyl, and $R^{4b}$ is hydrogen, or a pharmaceutically acceptable salt thereof. In certain embodiments, $R^5$ is F, $R^{4a}$ is methyl, and $R^{4b}$ is hydrogen, or a pharmaceutically acceptable salt thereof. In certain embodiments, $R^5$ is halo, $R^{4a}$ is hydrogen, and $R^{4b}$ is ethyl, or a pharmaceutically acceptable salt thereof. In certain embodiments, $R^5$ is F, $R^{4a}$ is hydrogen, and $R^{4b}$ is ethyl, or a pharmaceutically acceptable salt thereof. In certain embodiments, $R^5$ is halo, $R^{4a}$ is ethyl, and $R^{4b}$ is hydrogen, or a pharmaceutically acceptable salt thereof. In certain embodiments, $R^5$ is F, $R^{4a}$ is ethyl, and $R^{4b}$ is hydrogen, or a pharmaceutically acceptable salt thereof.

In certain embodiments, pharmaceutical compositions comprising a therapeutically effective amount of a compound of formula (I), or a pharmaceutically acceptable salt thereof, in combination with a pharmaceutically acceptable carrier, are provided.

In certain embodiments, pharmaceutical compositions comprising a therapeutically effective amount of:

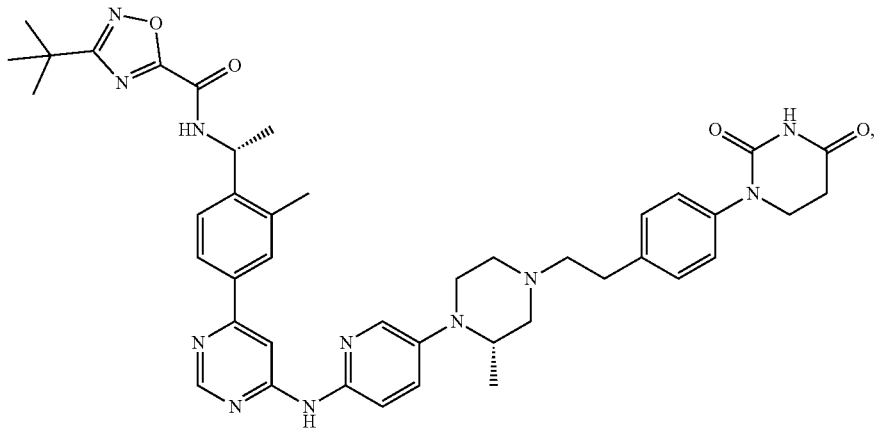 [SMILES: Cc1cc(-c2cc(Nc3ccc(N4CCN(CCc5ccc(N6CCC(=O)NC6=O)cc5)C[C@@H]4C)cn3)ncn2)ccc1[C@@H](C)NC(=O)c1nc(C(C)(C)C)no1]

or a pharmaceutically acceptable salt thereof, in combination with a pharmaceutically acceptable carrier, are provided.
In certain embodiments, the compound is:
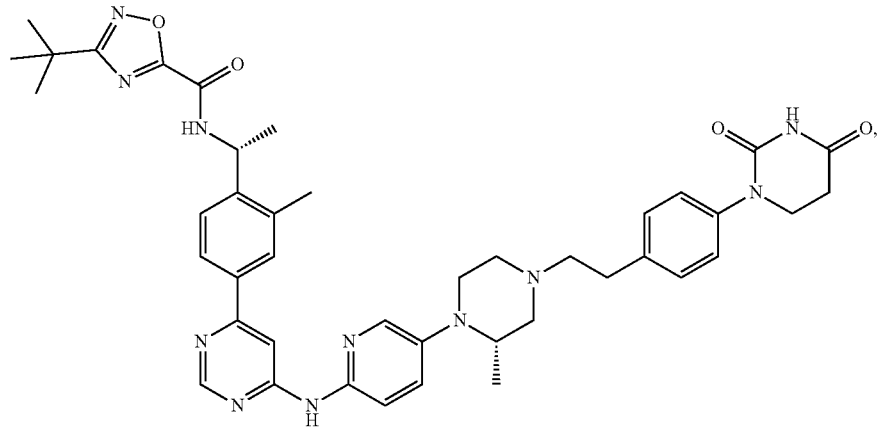 [SMILES: Cc1cc(-c2cc(Nc3ccc(N4CCN(CCc5ccc(N6CCC(=O)NC6=O)cc5)C[C@@H]4C)cn3)ncn2)ccc1[C@@H](C)NC(=O)c1nc(C(C)(C)C)no1]
or a pharmaceutically acceptable salt thereof.
In certain embodiments, the compound is:
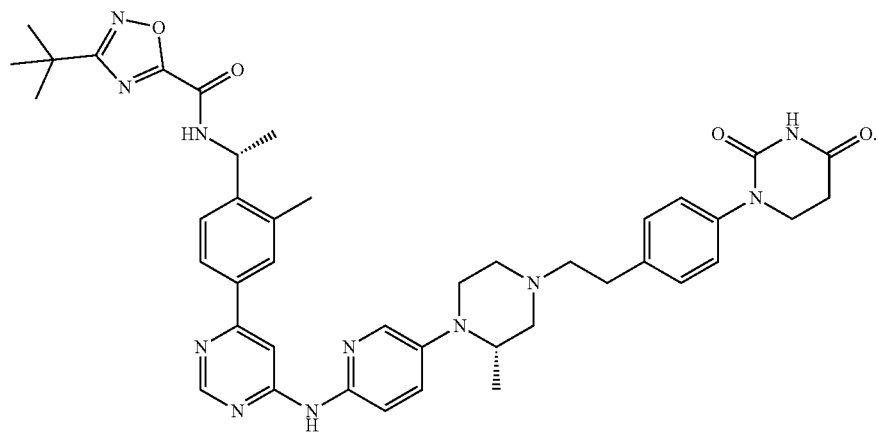 [SMILES: Cc1cc(-c2cc(Nc3ccc(N4CCN(CCc5ccc(N6CCC(=O)NC6=O)cc5)C[C@@H]4C)cn3)ncn2)ccc1[C@@H](C)NC(=O)c1nc(C(C)(C)C)no1]
In certain embodiments, the compound is the pharmaceutically acceptable salt of:
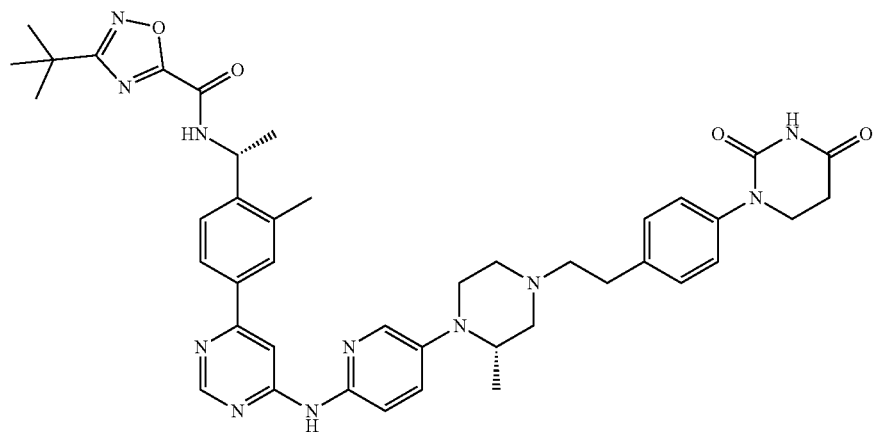 [SMILES: Cc1cc(-c2cc(Nc3ccc(N4CCN(CCc5ccc(N6CCC(=O)NC6=O)cc5)C[C@@H]4C)cn3)ncn2)ccc1[C@@H](C)NC(=O)c1nc(C(C)(C)C)no1]

In certain embodiments, the compound is 3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-methylphenyl}ethyl]-1,2,4-oxadiazole-5-carboxamide, or a pharmaceutically acceptable salt thereof.

In certain embodiments, the compound is 3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-methylphenyl}ethyl]-1,2,4-oxadiazole-5-carboxamide.

In certain embodiments, the compound is the pharmaceutically acceptable salt of: In certain embodiments, the compound is 3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-methylphenyl}ethyl]-1,2,4-oxadiazole-5-carboxamide.

In certain embodiments, the compound is selected from the group consisting of:

3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-methylphenyl}ethyl]-1,2,4-oxadiazole-5-carboxamide;

3-tert-butyl-N-[(1R)-1-{4-[6-({5-[(2R)-4-{2-[4-(2,4-dioxo-1,3-diazinan-1-yl)phenyl]ethyl}-2-methylpiperazin-1-yl]pyridin-2-yl}amino)pyrimidin-4-yl]-2-methylphenyl}ethyl]-1,2,4-oxadiazole-5-carboxamide;

3-tert-butyl-N-{(1R)-1-[4-(6-{[5-(4-{2-[4-(2,4-dioxo-1,3-diazinan-1-yl)phenyl]ethyl}piperazin-1-yl)pyridin-2-yl]amino}pyrimidin-4-yl)-2-methylphenyl]ethyl}-1,2,4-oxadiazole-5-carboxamide;

3-tert-butyl-N-[(1R)-1-{4-[6-({5-[(2S)-4-{2-[4-(2,4-dioxo-1,3-diazinan-1-yl)-3-fluorophenyl]ethyl}-2-methylpiperazin-1-yl]pyridin-2-yl}amino)pyrimidin-4-yl]-2-methylphenyl}ethyl]-1,2,4-oxadiazole-5-carboxamide;

3-tert-butyl-N-[(1R)-1-{4-[6-({5-[(2R)-4-{2-[4-(2,4-dioxo-1,3-diazinan-1-yl)-3-fluorophenyl]ethyl}-2-methylpiperazin-1-yl]pyridin-2-yl}amino)pyrimidin-4-yl]-2-methylphenyl}ethyl]-1,2,4-oxadiazole-5-carboxamide;

3-tert-butyl-N-[(1R)-1-{4-[6-({5-[(2S)-4-{2-[4-(2,4-dioxo-1,3-diazinan-1-yl)phenyl]ethyl}-2-ethylpiperazin-1-yl]pyridin-2-yl}amino)pyrimidin-4-yl]-2-methylphenyl}ethyl]-1,2,4-oxadiazole-5-carboxamide;

3-tert-butyl-N-[(1R)-1-{4-[6-({5-[(2S)-4-{2-[4-(2,4-dioxo-1,3-diazinan-1-yl)-3-fluorophenyl]ethyl}-2-ethylpiperazin-1-yl]pyridin-2-yl}amino)pyrimidin-4-yl]-2-methylphenyl}ethyl]-1,2,4-oxadiazole-5-carboxamide;

3-tert-butyl-N-[(1R)-1-{4-[6-({5-[(2R)-4-{2-[4-(2,4-dioxo-1,3-diazinan-1-yl)phenyl]ethyl}-2-ethylpiperazin-1-yl]pyridin-2-yl}amino)pyrimidin-4-yl]-2-methylphenyl}ethyl]-1,2,4-oxadiazole-5-carboxamide;

3-tert-butyl-N-{(1R)-1-[4-(6-{[5-(4-{2-[4-(2,4-dioxo-1,3-diazinan-1-yl)phenyl]ethyl}-2,2-dimethylpiperazin-1-yl)pyridin-2-yl]amino}pyrimidin-4-yl)-2-methylphenyl]ethyl}-1,2,4-oxadiazole-5-carboxamide;

3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-3-fluoro-2-methylphenyl}ethyl]-1,2,4-oxadiazole-5-carboxamide;

3-tert-butyl-N-{(1R)-1-[4-(6-{[5-(4-{2-[4-(2,4-dioxo-1,3-diazinan-1-yl)phenyl]ethyl}piperazin-1-yl)pyridin-2-yl]amino}pyrimidin-4-yl)-3-fluoro-2-methylphenyl]ethyl}-1,2,4-oxadiazole-5-carboxamide;

3-tert-butyl-N-{(1R)-1-[4-(6-{[5-(4-{2-[4-(2,4-dioxo-1,3-diazinan-1-yl)phenyl]ethyl}piperazin-1-yl)pyridin-2-yl]amino}pyrimidin-4-yl)-5-fluoro-2-methylphenyl]ethyl}-1,2,4-oxadiazole-5-carboxamide;

3-tert-butyl-N-[(1R)-1-{4-[6-({5-[(2S)-4-{2-[4-(2,4-dioxo-1,3-diazinan-1-yl)phenyl]ethyl}-2-(propan-2-yl)piperazin-1-yl]pyridin-2-yl}amino)pyrimidin-4-yl]-2-methylphenyl}ethyl]-1,2,4-oxadiazole-5-carboxamide;

3-tert-butyl-N-[(1R)-1-{2-chloro-4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]phenyl}ethyl]-1,2,4-oxadiazole-5-carboxamide;

3-tert-butyl-N-[(1R)-1-{4-[6-({5-[(2R)-4-{2-[4-(2,4-dioxo-1,3-diazinan-1-yl)phenyl]ethyl}-2-(methoxymethyl)piperazin-1-yl]pyridin-2-yl}amino)pyrimidin-4-yl]-2-methylphenyl}ethyl]-1,2,4-oxadiazole-5-carboxamide;

3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-(trifluoromethyl)phenyl}ethyl]-1,2,4-oxadiazole-5-carboxamide; and 3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-fluorophenyl}ethyl]-1,2,4-oxadiazole-5-carboxamide; or a pharmaceutically acceptable salt thereof.

Definition of Terms

As used in the specification and the appended claims, unless specified to the contrary, the following terms have the meaning indicated.

It is noted that, as used in this specification and the intended claims, the singular form "a," "an," and "the" include plural referents unless the context clearly dictates otherwise. Thus, for example, reference to "a compound" includes a single compound as well as one or more of the same or different compounds.

In some instances, the number of carbon atoms in a moiety is indicated by the prefix "$C_x$-$C_y$," wherein x is the minimum and y is the maximum number of carbon atoms in the substituent. Thus, for example, "$C_1$-$C_3$ alkyl" means an alkyl substituent containing from 1 to 3 carbon atoms.

The term "alkyl," as used herein, refers to a saturated, straight, or branched hydrocarbon chain radical having one, two, three, four, five, or six carbon atoms, unless otherwise specified. The term "$C_1$-$C_3$ alkyl" refers to an alkyl having one, two, or three carbon atoms. Examples of alkyls include, but are not limited to, methyl, ethyl, propyl, isopropyl, and the like. In certain embodiments, the alkyl is methyl. In certain embodiments, the alkyl is ethyl. In certain embodiments, the alkyl is propyl. In certain embodiments, the alkyl is isopropyl.

The term "halo" as used herein, means Cl (chloro), Br (bromo), I (iodo), and F (fluoro). In certain embodiments, halo is selected from the group consisting of Cl or F. In certain embodiments, the halo is Cl. In certain embodiments, the halo is F.

The term "haloalkyl," as used herein, refers to an alkyl group, as defined herein, in which one or more hydrogen atoms are replaced by a halo group. As an example, the term "$C_1$-$C_3$ haloalkyl" refers to a haloalkyl having one, two, or three carbon atoms. In certain embodiments, one, two or three hydrogen atoms may each be replaced by a fluoro group. An example of a haloalkyl is trifluoromethyl or $CF_3$.

BRIEF DESCRIPTION OF THE DRAWINGS

FIG. 1 shows in vivo activity of Compound 1 (Example 1) in TCL1-driven CLL bearing Btk$^{C481S}$ mutation in C57BL/6 mice.

DETAILED DESCRIPTION OF THE INVENTION

In certain embodiments, the compounds disclosed herein comprise two ligands connected via a linker. The first ligand is capable of binding Btk. The second ligand is capable of recruiting a ubiquitin ligase. In certain embodiments, the ubiquitin ligase is an E3 ligase. In certain embodiments, the E3 ubiquitin ligase is cereblon (CRBN) and/or comprises cereblon (CRBN). In certain embodiments, the second ligand is capable of recruiting CRBN. In certain embodiments, the second ligand is capable of binding CRBN. In certain embodiments, the compounds described herein are capable of binding Btk and capable of recruiting a ubiquitin ligase that comprises cereblon. In certain embodiments, the compounds disclosed herein recruit E3 ligase to Btk and cause proximity-induced ubiquitination and degradation of the Btk by the ubiquitin proteasome system (UPS). In certain embodiments, the compounds disclosed herein are capable of binding Btk and reducing the amount of Btk in the cell via degradation.

In certain embodiments, the compounds disclosed herein are useful in the treatment of chronic lymphocytic leukemia (CLL). For example, the compounds described herein are useful for treating CLL by degrading Btk in patients via a ubiquitin proteolytic pathway.

In certain embodiments, the compounds disclosed herein degrade $Btk^{C481S}$ protein (Btk protein having the $C_{481}$ mutation) in cell lines expressing $Btk^{C481S}$.

In certain embodiments, a method of treating a patient with CLL comprising administering to the patient a compound of formula (I) is provided.

In certain embodiments, methods for treating CLL comprising administering to a subject in need thereof a therapeutically effective amount of a compound of formula (I) are provided.

The phrase "pharmaceutically acceptable salt" refers to those salts which are, within the scope of sound medical judgement, suitable for use in contact with the tissues of humans and lower animals without undue toxicity, irritation, allergic response and the like and are commensurate with a reasonable benefit/risk ratio.

The term "subject," as used herein, refers to a human. The terms "human," "patient," and "subject" are used interchangeably herein.

The terms "treat," "treating," and "treatment," as used herein, refer to a method of alleviating or abrogating a disease and/or its attendant symptoms.

The phrase "therapeutically effective amount" refers to an amount of a compound, or a pharmaceutically acceptable salt thereof, sufficient to prevent the development of or to alleviate to some extent one or more of the symptoms of the condition or disorder being treated when administered for treatment in a particular subject or subject population. In certain embodiments, the amount is effective to degrade Btk in the patient.

General Synthesis

The compounds of the present disclosure can be better understood in connection with the following synthetic schemes and methods which illustrate a means by which the compounds can be prepared. Representative procedures are shown in, but are not limited to, Schemes 1-5. In Schemes 1-5, the variables $R^1$, $R^2$, $R^3$, $R^4$, and $R^5$ may be as described herein. Final compounds of the invention were named by using ACD/Name 2021.1.3 (File Version N15E41, Build 123232, 7 Jul. 2021) software program and/or by using Struct=Name naming algorithm as part of CHEMDRAW® Professional v. 20.1.1.125. Intermediates were named using CHEMDRAW® Professional v. 20.1.1.125.

Compounds of the present invention may be prepared according to the schemes set forth below.

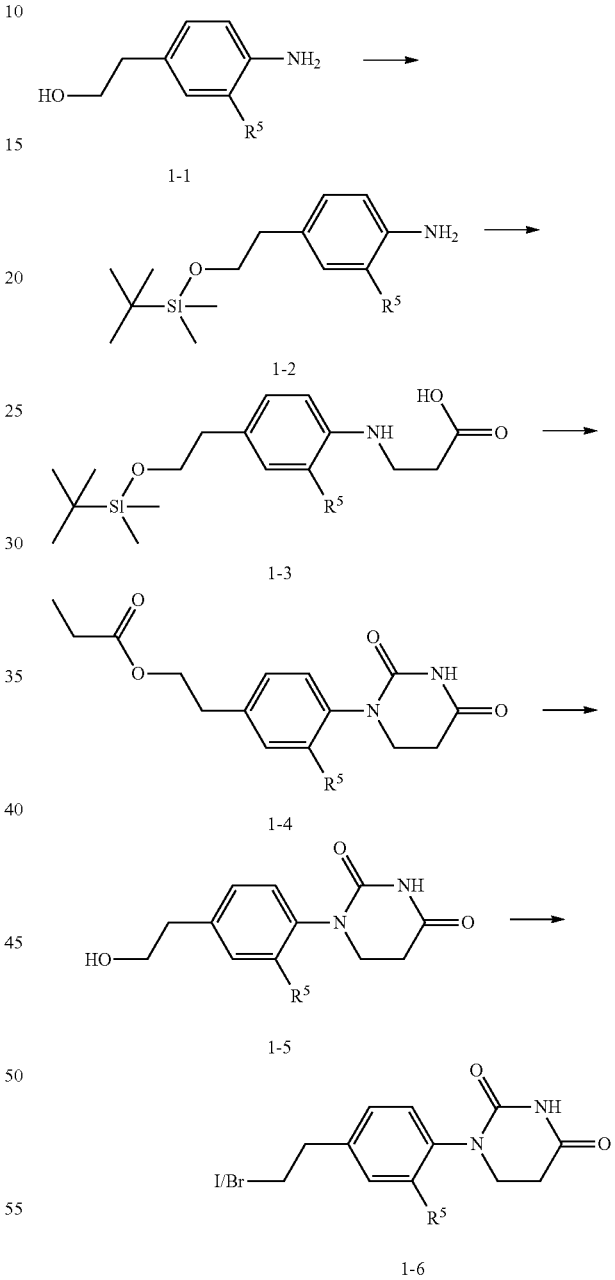

Scheme 1

Methods for preparing substituted 1-phenyldihydropyrimidine-2,4(1H,3H)-dione building block 1-6 are illustrated in Scheme 1. The substitution group $R^5$ on compound 1-1 may be a halo, hydrogen, or $C_1$-$C_3$ alkyl, as described herein. Reaction of compound 1-1 with tert-butyldimethylsilyl chloride in the presence of imidazole may provide compound 1-2. Reaction of compound 1-2 with acrylic acid using heat may form compound 1-3. Compound 1-3 may react with urea in heated acetic acid to yield compound 1-4. Compound 1-4 may be treated with aqueous HCl to provide intermediate 1-5. Intermediate 1-5 may be treated with iodine followed by Ph₃P in the presence of imidazole to provide iodo compound 1-6, or it may be treated with CBr₄ followed by Ph₃P to provide bromo compound 1-6.

Scheme 2

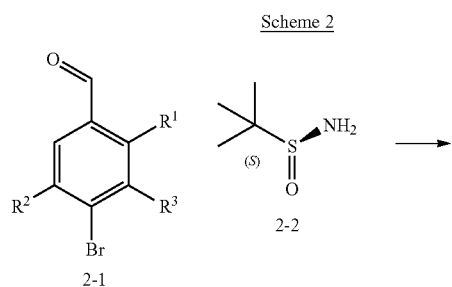

2-1     2-2

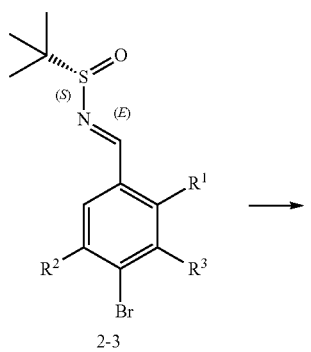

2-3

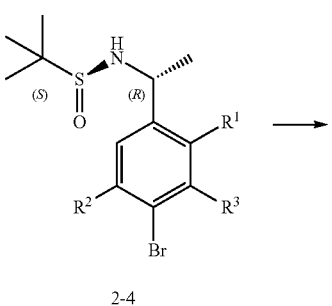

2-4

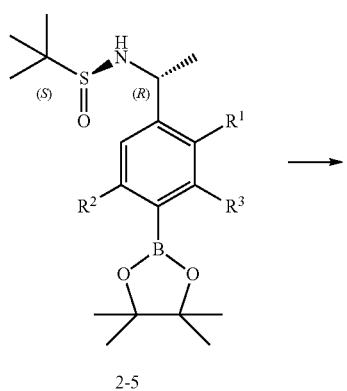

2-5

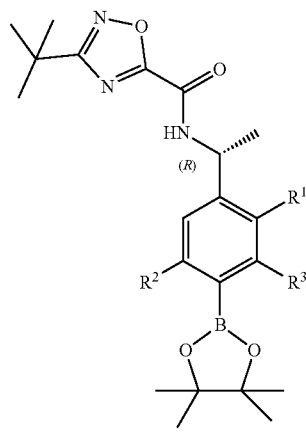

2-6     2-7

A method for preparing substituted building block 2-7 is illustrated in Scheme 2. Reaction of substituted benzaldehyde 2-1 wherein $R^1$, $R^2$, and $R^3$ may be as described herein, with (S)-2-methylpropane-2-sulfinamide 2-2 may provide compound 2-3. Reacting compound 2-3 with CH₃MgBr under Grignard reaction conditions may afford intermediate 2-4. Using bis(pinacolato)diboron and a palladium catalyst, intermediate 2-5 may be synthesized from intermediate 2-4. Amine 2-6 may be prepared from intermediate 2-5 by removing the t-butylsulfinyl group using strong acid or iodine. Heteroaryl carboxamide building block 2-7 may be directly synthesized from amine 2-6 with methyl 3-(tert-butyl)-1,2,4-oxadiazole-5-carboxylate.

Scheme 3

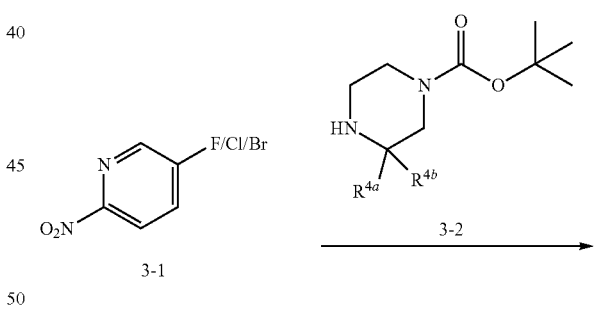

3-1     3-2

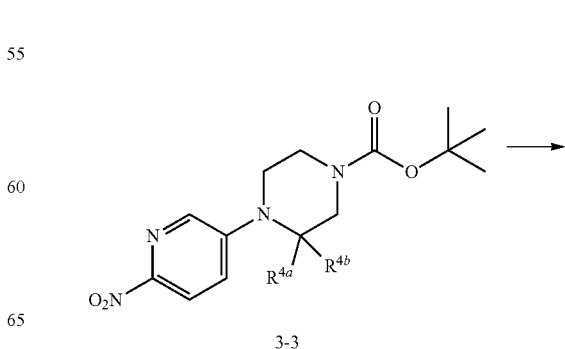

3-3

-continued
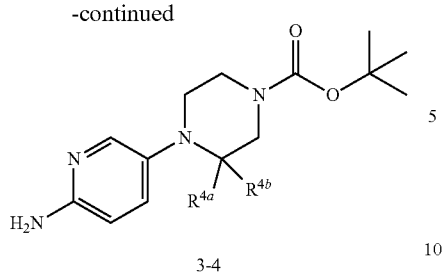
3-4
As shown in Scheme 3, building block 3-4, wherein $R^{4a}$ and $R^{4b}$ are as described herein, may be prepared from compound 3-3 by hydrogenation or a nitro reduction reaction. Intermediate compound 3-3 may be prepared from 2-nitro-5-halopyridine compound 3-1 and substituted piperazine compound 3-2 by a $S_NAr$ reaction or a Buchwald-Hartwing cross-coupling reaction.
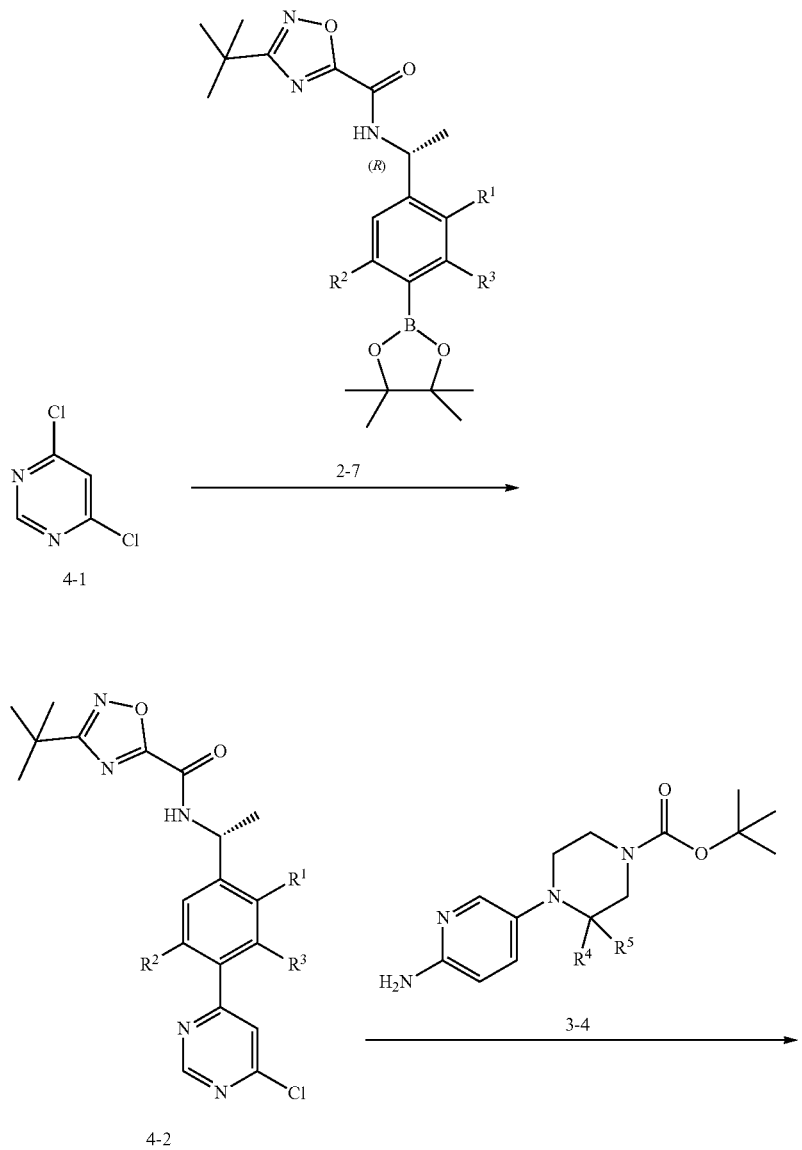
Scheme 4

-continued

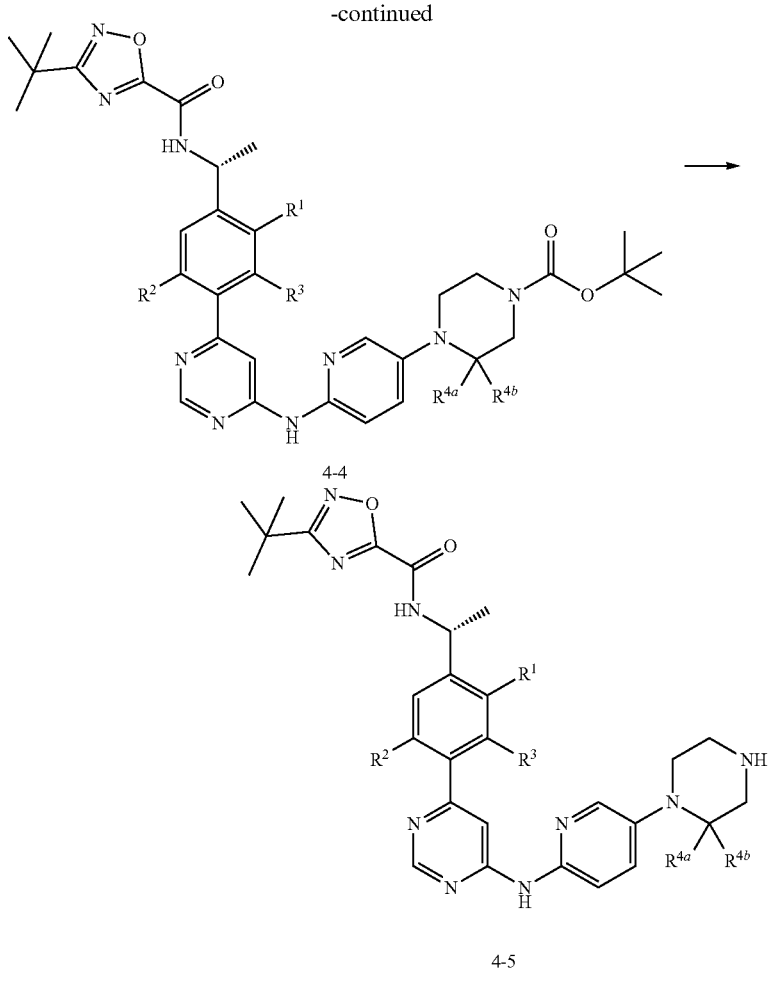

A general synthesis for intermediates of formula 4-5 is shown in Scheme 4, wherein $R^1$, $R^2$, $R^3$, $R^{4a}$, and $R^{4b}$ may be as described herein. Intermediate 4-2 may be prepared via a Suzuki reaction of building block 2-7 with 4,6-dicholopyrimidine 4-1. Intermediate 4-4 may be prepared from compound 4-2 via a Buchwald-Hartwing cross-coupling reaction with substituted 2-aminopyridine compound 3-4. The tert-butyloxycarbonyl protecting group may be cleaved using hydrochloric acid or trifluoroacetic acid to afford building block 4-5.

Scheme 5

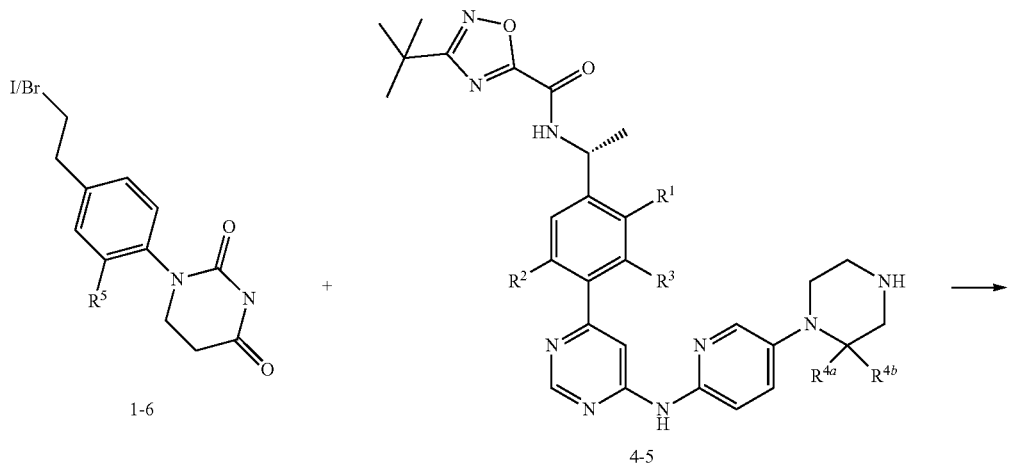

-continued

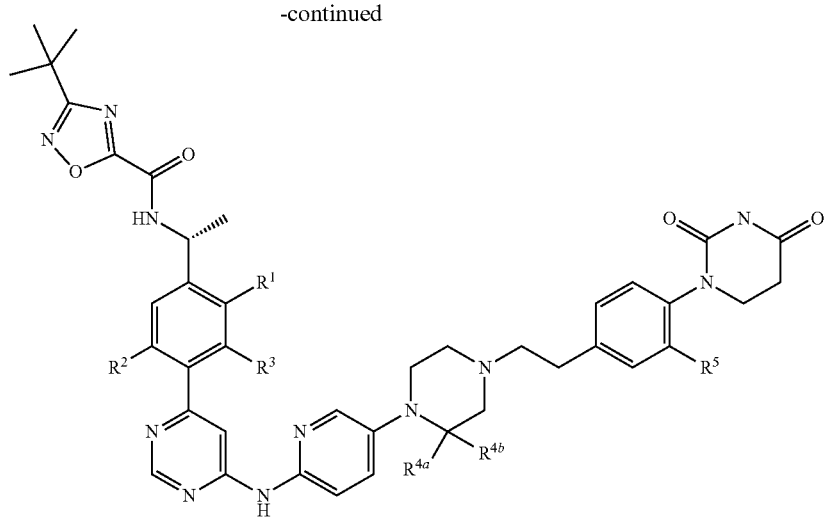

5-4

A general synthesis for target compounds of formula 5-4 is shown in Scheme 5, wherein $R^1$, $R^2$, $R^3$, $R^{4a}$, $R^{4b}$, and $R^5$ may be as described herein. Iodo or bromo building block 1-6 may react with intermediate 4-5 via an alkylation reaction using sodium iodide and a base such as N,N-diisopropylethylamine to provide target compound 5-4.

It can be appreciated that the synthetic schemes and specific examples as illustrated in the Examples section are illustrative and are not to be read as limiting the scope of the present disclosure as it is defined in the appended claims. All alternatives, modifications, and equivalents of the synthetic methods and specific examples are included within the scope of the claims.

The following Examples may be used for illustrative purposes and should not be deemed to narrow the scope of the present disclosure.

Exemplary compounds of formula (I) include, but are not limited to, the compounds shown in Table 1 below, and pharmaceutically acceptable salts thereof.

TABLE 1

| Exemplary Compounds | |
| --- | --- |
| EXAMPLE | COMPOUND STRUCTURE |
| 1 | |

TABLE 1-continued

Exemplary Compounds

| EXAMPLE | COMPOUND STRUCTURE |
|---|---|
| 2 | 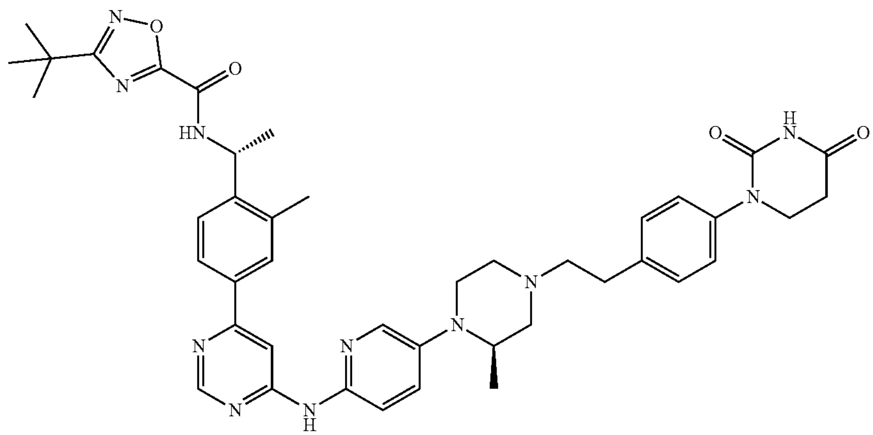 [SMILES: Cc1cc(-c2cc(Nc3ccc(N4CCN(CCc5ccc(N6CCC(=O)NC6=O)cc5)C[C@H]4C)cn3)ncn2)ccc1[C@@H](C)NC(=O)c1nc(C(C)(C)C)no1] |
| 3 | 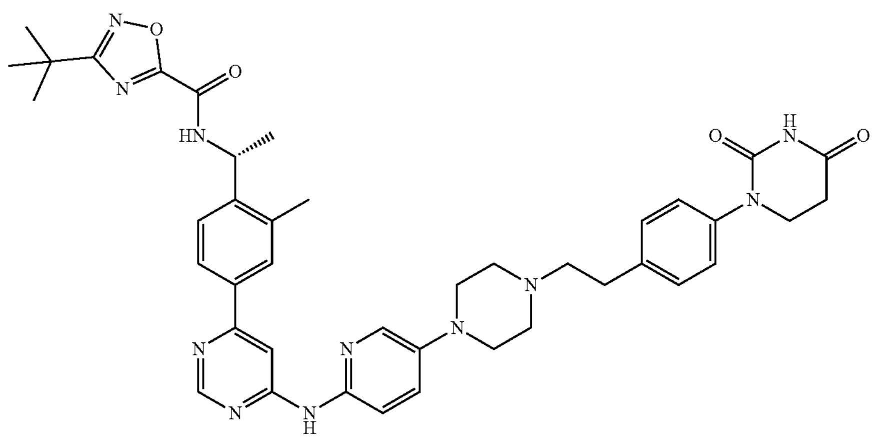 [SMILES: Cc1cc(-c2cc(Nc3ccc(N4CCN(CCc5ccc(N6CCC(=O)NC6=O)cc5)CC4)cn3)ncn2)ccc1[C@@H](C)NC(=O)c1nc(C(C)(C)C)no1] |
| 4 | 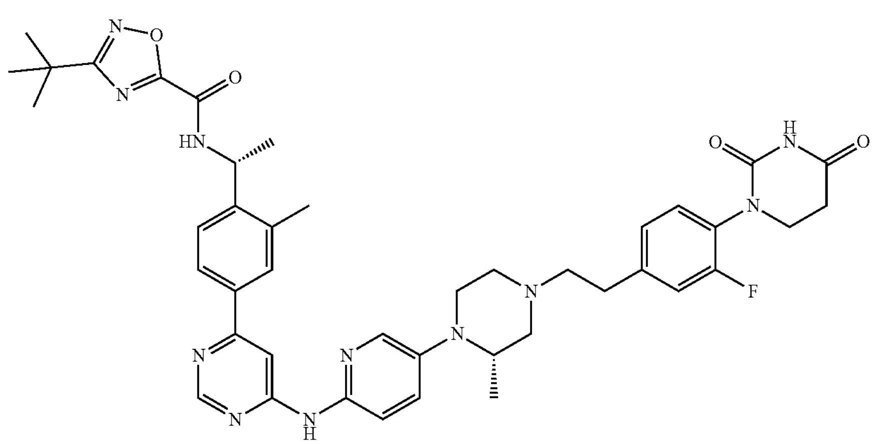 [SMILES: Cc1cc(-c2cc(Nc3ccc(N4CCN(CCc5ccc(N6CCC(=O)NC6=O)c(F)c5)C[C@@H]4C)cn3)ncn2)ccc1[C@@H](C)NC(=O)c1nc(C(C)(C)C)no1] |

TABLE 1-continued

Exemplary Compounds

| EXAMPLE | COMPOUND STRUCTURE |
| --- | --- |
| 5 | 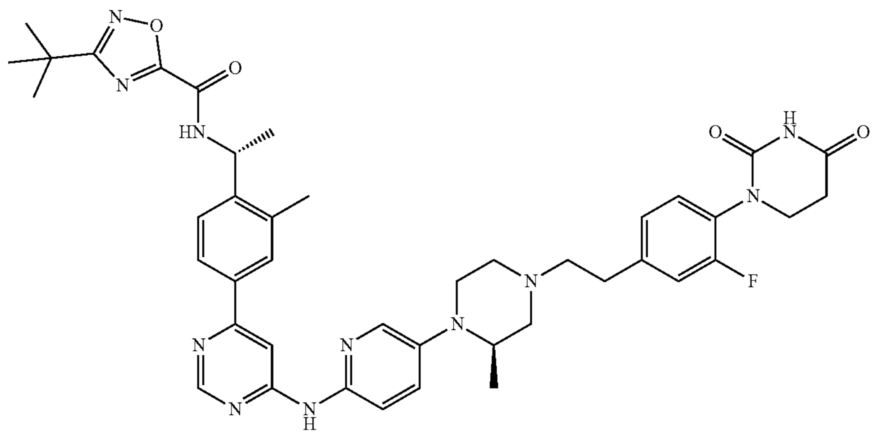 [SMILES: Cc1cc(-c2cc(Nc3ccc(N4CCN(CCc5ccc(N6CCC(=O)NC6=O)c(F)c5)C[C@H]4C)cn3)ncn2)ccc1[C@@H](C)NC(=O)c1nc(C(C)(C)C)no1] |
| 6 | 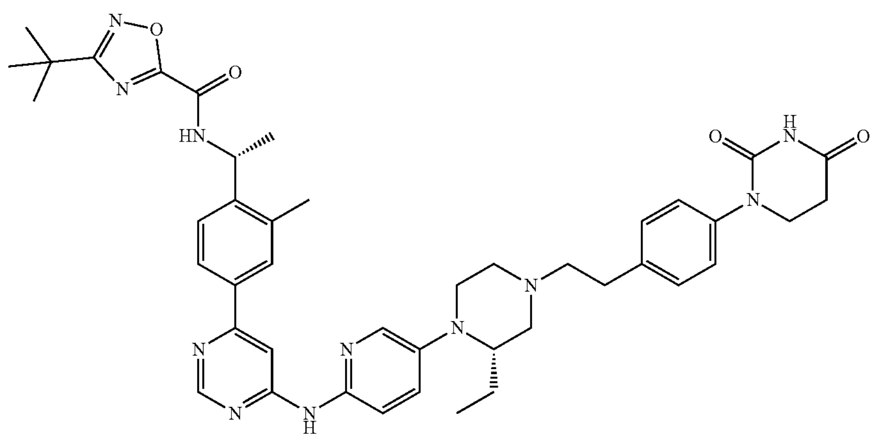 [SMILES: CC[C@H]1CN(CCc2ccc(N3CCC(=O)NC3=O)cc2)CCN1c1ccc(Nc2cc(-c3ccc([C@@H](C)NC(=O)c4nc(C(C)(C)C)no4)c(C)c3)ncn2)nc1] |
| 7 | 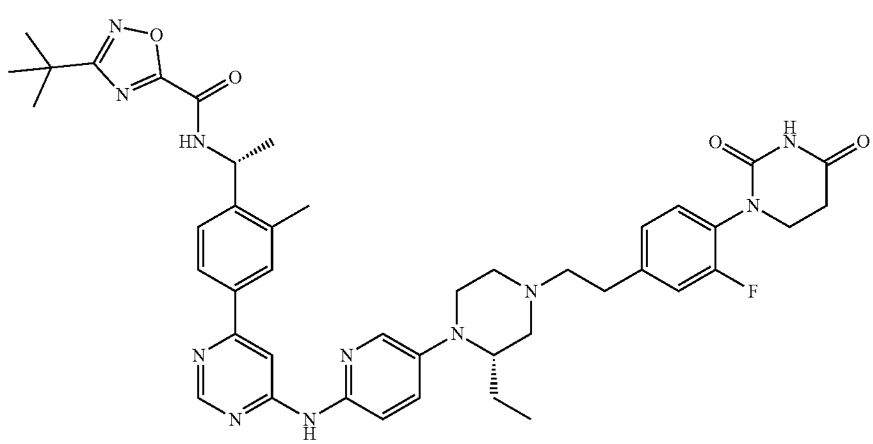 [SMILES: CC[C@H]1CN(CCc2ccc(N3CCC(=O)NC3=O)c(F)c2)CCN1c1ccc(Nc2cc(-c3ccc([C@@H](C)NC(=O)c4nc(C(C)(C)C)no4)c(C)c3)ncn2)nc1] |

TABLE 1-continued
Exemplary Compounds
| EXAMPLE | COMPOUND STRUCTURE |
|---|---|
| 8 | 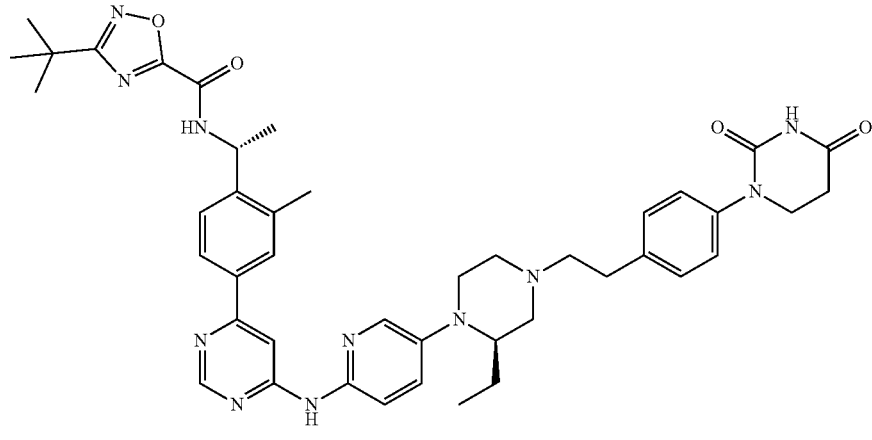 [SMILES: CC[C@@H]1CN(CCc2ccc(N3CCC(=O)NC3=O)cc2)CCN1c1ccc(Nc2cc(-c3ccc([C@@H](C)NC(=O)c4nc(C(C)(C)C)no4)c(C)c3)ncn2)nc1] |
| 9 | 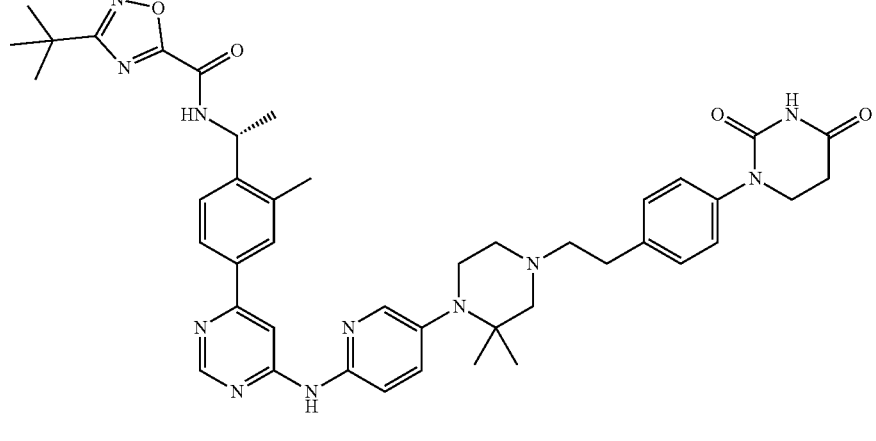 |
| 10 | 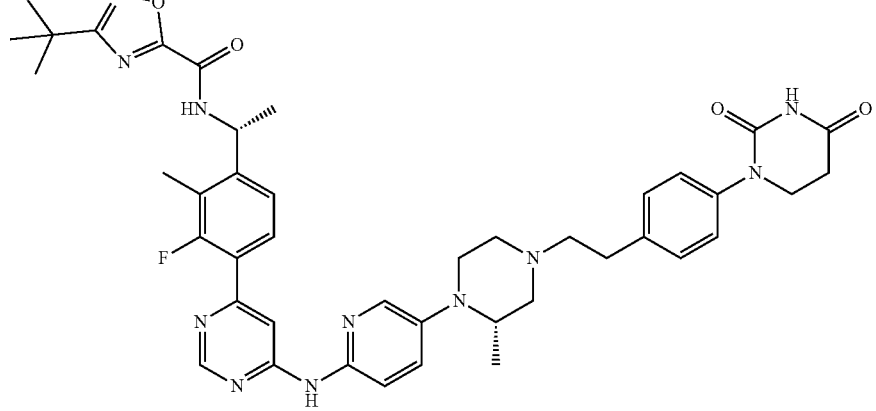 |

TABLE 1-continued

Exemplary Compounds

| EXAMPLE | COMPOUND STRUCTURE |
| --- | --- |
| 11 | 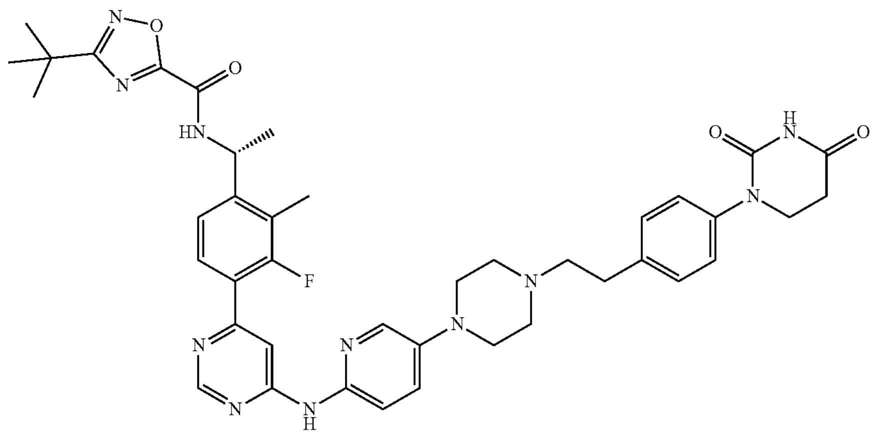 [SMILES: Cc1c([C@@H](C)NC(=O)c2nc(C(C)(C)C)no2)ccc(-c2cc(Nc3ccc(N4CCN(CCc5ccc(N6CCC(=O)NC6=O)cc5)CC4)cn3)ncn2)c1F] |
| 12 | 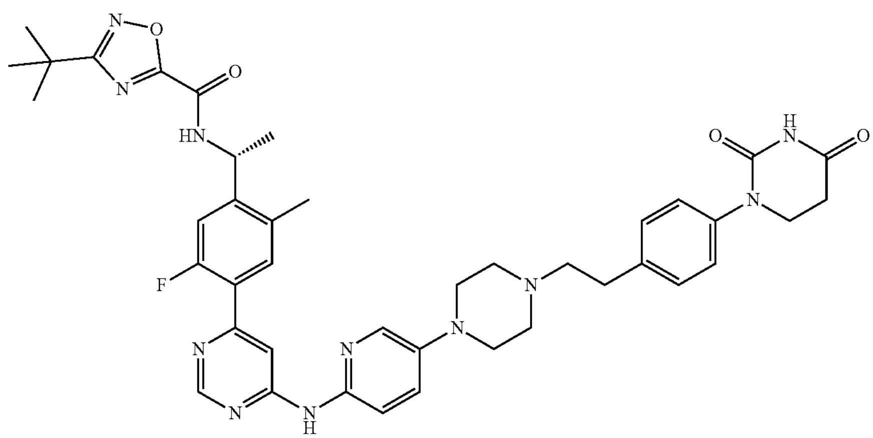 [SMILES: Cc1cc(-c2cc(Nc3ccc(N4CCN(CCc5ccc(N6CCC(=O)NC6=O)cc5)CC4)cn3)ncn2)c(F)cc1[C@@H](C)NC(=O)c1nc(C(C)(C)C)no1] |
| 13 | 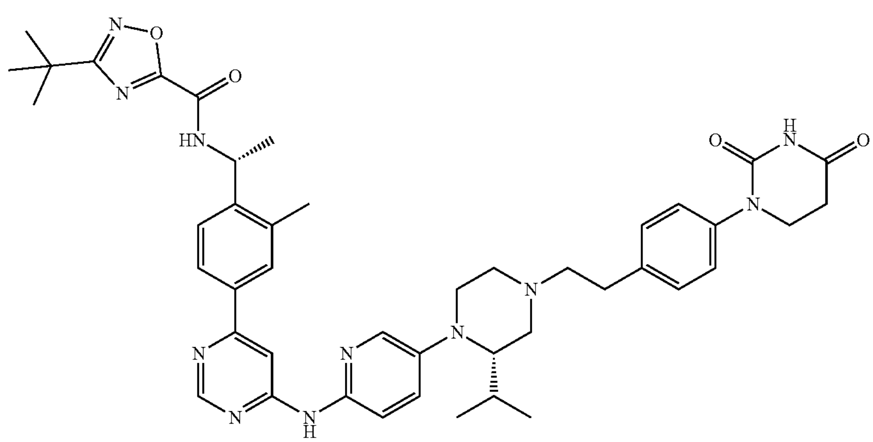 [SMILES: Cc1cc(-c2cc(Nc3ccc(N4CCN(CCc5ccc(N6CCC(=O)NC6=O)cc5)C[C@@H]4C(C)C)cn3)ncn2)ccc1[C@@H](C)NC(=O)c1nc(C(C)(C)C)no1] |

TABLE 1-continued

Exemplary Compounds

| EXAMPLE | COMPOUND STRUCTURE |
|---|---|
| 14 | 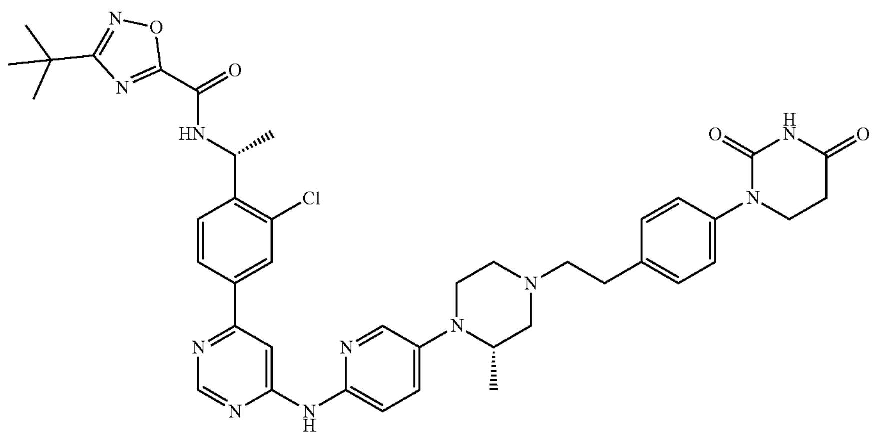 [SMILES: C[C@@H](NC(=O)c1nc(C(C)(C)C)no1)c1ccc(-c2cc(Nc3ccc(N4CCN(CCc5ccc(N6CCC(=O)NC6=O)cc5)C[C@@H]4C)cn3)ncn2)cc1Cl] |
| 15 | 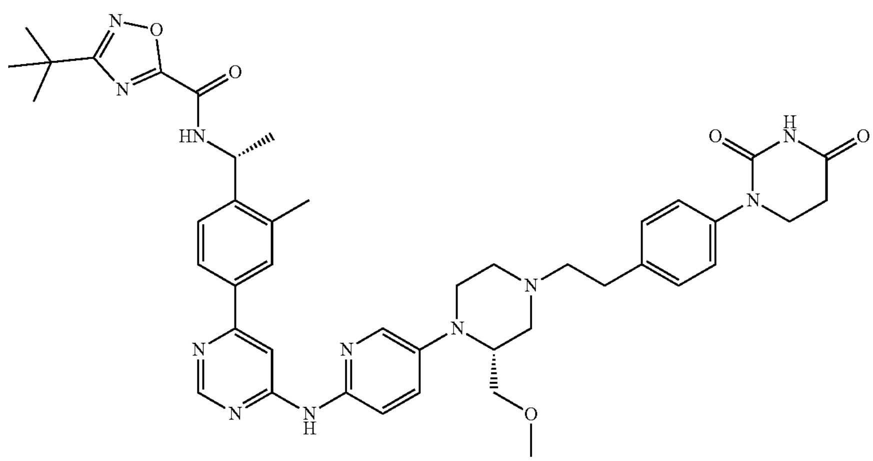 [SMILES: COC[C@H]1CN(CCc2ccc(N3CCC(=O)NC3=O)cc2)CCN1c1ccc(Nc2cc(-c3ccc([C@@H](C)NC(=O)c4nc(C(C)(C)C)no4)c(C)c3)ncn2)nc1] |
| 16 | 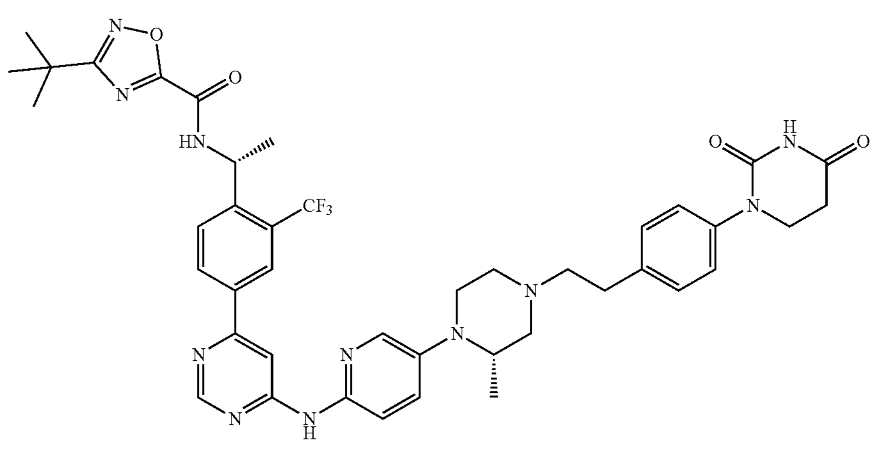 [SMILES: C[C@@H](NC(=O)c1nc(C(C)(C)C)no1)c1ccc(-c2cc(Nc3ccc(N4CCN(CCc5ccc(N6CCC(=O)NC6=O)cc5)C[C@@H]4C)cn3)ncn2)cc1C(F)(F)F] |

TABLE 1-continued

Exemplary Compounds

| EXAMPLE | COMPOUND STRUCTURE |
|---|---|
| 17 | 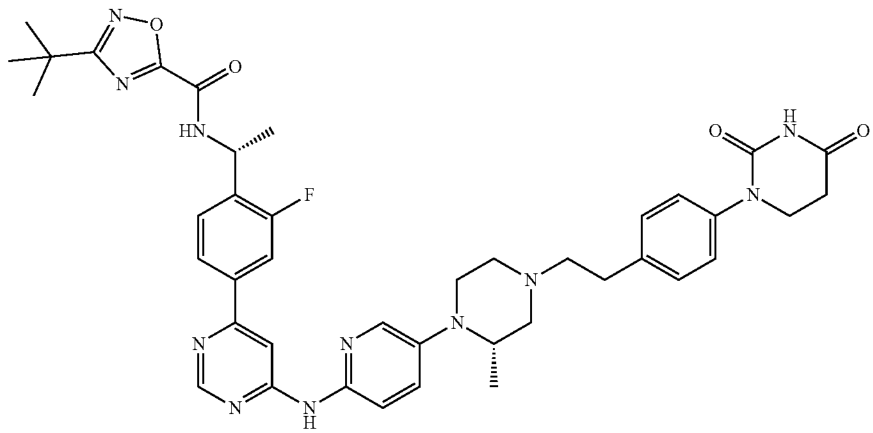 [SMILES: C[C@@H](NC(=O)c1nc(C(C)(C)C)no1)c1ccc(-c2cc(Nc3ccc(N4CCN(CCc5ccc(N6CCC(=O)NC6=O)cc5)C[C@@H]4C)cn3)ncn2)cc1F] |
| 18 | 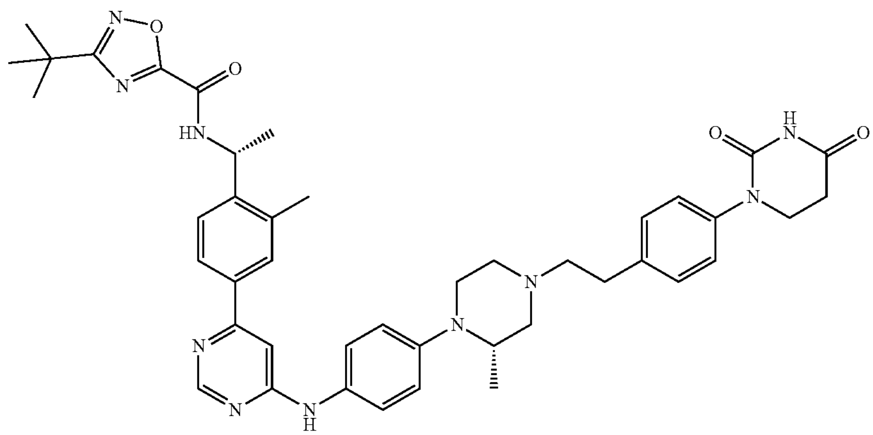 [SMILES: Cc1cc(-c2cc(Nc3ccc(N4CCN(CCc5ccc(N6CCC(=O)NC6=O)cc5)C[C@@H]4C)cc3)ncn2)ccc1[C@@H](C)NC(=O)c1nc(C(C)(C)C)no1] |
| 19 | 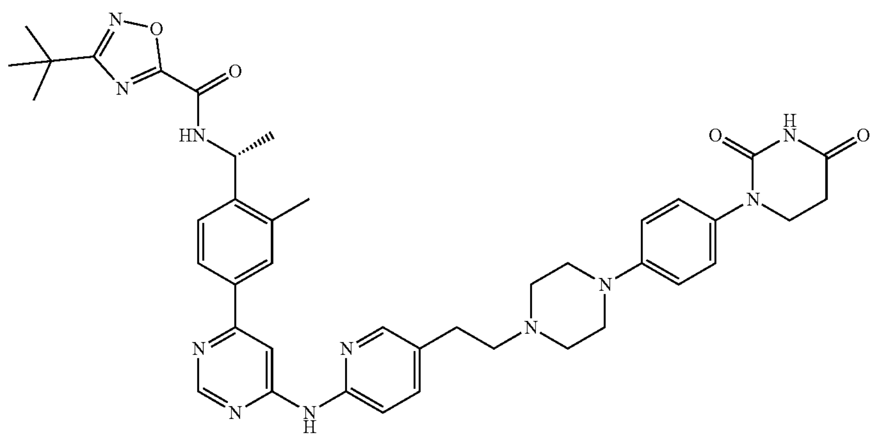 [SMILES: Cc1cc(-c2cc(Nc3ccc(CCN4CCN(c5ccc(N6CCC(=O)NC6=O)cc5)CC4)cn3)ncn2)ccc1[C@@H](C)NC(=O)c1nc(C(C)(C)C)no1] |

EXAMPLES

| Abbreviation | Definition |
|---|---|
| NMR | nuclear magnetic resonance |
| S | Singlet |
| br s | broad singlet |
| D | duplet or doublet |

-continued

| Abbreviation | Definition |
|---|---|
| br d | broad doublet |
| br dd | broad doublet of doublets |
| M | Multiplet |
| T | Triplet |
| br t | broad triplet |
| Td | triplet of doublets |

| Abbreviation | Definition |
| --- | --- |
| Q | Quartet |
| Qd | quartet of doublets |
| Dd | doublet of doublets |
| Dt | doublet of triplets |
| Dq | doublet of quartets |
| Ddd | doublet of doublet of doublets |
| Dtd | doublet of triplet of doublets |
| Quin | quintuplet |
| mL | milliliter |
| μL | microliter |
| L | liter |
| G | gram |
| Mg | milligram |
| Mol | moles |
| Mmol | millimoles |
| mM | millimolar |
| M | molarity (moles/liter) |
| μM | micromolar |
| N | normality (equivalent/liter) |
| Ppm | parts per million |
| Psi | pounds per square inch |
| HPLC | high pressure liquid chromatography |
| LC/MS or LCMS | liquid chromatography—mass spectrometry |
| MS | mass spectrometry |
| ESI | electrospray ionization |
| ATP | adenosine triphosphate |
| BSA | bovine serum albumin |
| EDTA | ethylenediaminetetraacetic acid |
| DTT | dithiothreitol |
| HEPES | (4-(2-hydroxyethyl)-1-piperazineethanesulfonic acid) |
| $IC_{50}$ | half maximal inhibitory concentration |
| $DC_{50}$ | half maximal degradation concentration |
| UV | ultraviolet |
| TLC | thin layer chromatography |
| Mm | millimeter |
| Mm | micrometer (micron) |
| MHz | megahertz |
| Nm | nanometer |
| ° C. | degrees Celsius |
| m/z | mass to charge ratio |
| pH | potential of hydrogen |
| Pd/C | palladium on carbon |

Final compounds obtained through preparative HPLC may have been concentrated through lyophilization. Final Examples were typically purified to ≥95% purity as determined by HPLC and LCMS at 254 nm. $^1$H NMR spectra were recorded on a Bruker Avance™ III 400 MHz NMR spectrometer, or a Bruker Ascend™ 500 MHz NMR spectrometer. Chemical shifts (δ) were reported as parts per million (ppm) relative to residual undeuterated solvent as an internal reference.

Example 1

3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-methylphenyl}ethyl]-1,2,4-oxadiazole-5-carboxamide Example 1A (S,E)-N-(4-bromo-2-methylbenzylidene)-2-methylpropane-2-sulfinamide A 5 L reactor was charged with triisopropyl borate (1.50 L, 6.53 mol), 4-bromo-2-methylbenzaldehyde (1.00 kg, 5.02 mol), and (S)-2-methylpropane-2-sulfinamide (669 g, 5.53 mol) at ambient temperature. The mixture was stirred at 80° C. for 12 hours. The reaction was duplicated twice on the same scale. To the combined reaction mixtures of the three batches was added water (10.0 L), and the mixture was extracted with ethyl acetate (4.0 L×2), washed with brine (5.0 L), dried with sodium sulfate, and filtered. The filtrate was concentrated under reduced pressure, and the residue was triturated in petroleum ether (5.0 L) for 2 hours and filtered. The filter cake was washed with petroleum ether, and the cake was dried under reduced pressure to provide the title compound. $^1$H NMR (400 MHz, CDCl$_3$): δ ppm 8.79 (s, 1H), 7.77 (d, J=6.4 Hz, 1H), 7.44 (s, 1H), 7.43 (d, J=6.4 Hz, 1H), 2.59 (s, 3H), 1.27 (s, 9H) ppm.

Example 1B (S)—N—((R)-1-(4-bromo-2-methylphenyl)ethyl)-2-methylpropane-2-sulfinamide A 50 L reactor was charged with dichloromethane (20.0 L) and Example 1A (1.00 kg, 3.31 mol). The mixture was chilled at −20° C. CH$_3$MgBr (3.0 M in tetrahydrofuran, 1.65 L, 4.96 mol) was added at −20° C. dropwise. The mixture was then stirred at ambient temperature for 16 hours. The reaction mixture was chilled in an ice bath, and to it was added saturated aqueous NH$_4$Cl solution (5.0 L). The organic phase was separated, and the aqueous phase was extracted with dichloromethane (3.0 L×2). The combined organic phase was washed with brine (5.0 L), dried with sodium sulfate, and filtered. The filtrate was concentrated under reduced pressure and the residue was triturated in petroleum ether. The crude material was isolated by filtration, washed with petroleum ether, and dried under reduced pressure. The same reaction was duplicated five times to provide the title compound. $^1$H NMR (400 MHz, dimethyl sulfoxide-d$_6$): δ ppm 7.38-7.31 (m, 3H), 5.33 (d, J=5.2 Hz, 1H), 4.55 (m, 1H), 2.30 (s, 3H), 1.40 (d, J=5.2 Hz, 1H), 1.08 (s, 9H) ppm. MS (ESI) m/z 318.0, 320.0 (M+H)$^+$.

Example 1C (S)-2-methyl-N—((R)-1-(2-methyl-4-(4,4,5,5-tetramethyl-1,3,2-dioxaborolan-2-yl)phenyl)ethyl)propane-2-sulfinamide A 5 L reactor was charged with Example 1B (600 g, 1.89 mol), dioxane (3.6 L), bis(pinacolato)diboron (600 g, 2.36 mol), potassium acetate (370 g, 3.77 mol) and Pd(dppf)Cl$_2$ ([1,1'-bis(diphenylphosphino)ferrocene]dichloropalladium (II), 23.0 g, 0.07 mol) at ambient temperature. The mixture was degassed with nitrogen and stirred at 85° C. for 8 hours under nitrogen. The same reaction was duplicated four times on the same scale. The combined reaction mixtures of the five batches were filtered through diatomaceous earth, and the filter cake was washed with ethyl acetate (0.5 L×3). The filtrate was concentrated under reduced pressure and the residue was subjected to silica flash column chromatography using petroleum ether and ethyl acetate to provide the title compound. $^1$H NMR (400 MHz, CDCl$_3$): δ ppm 7.58-7.38 (m, 3H), 5.31 (d, J=4.8 Hz, 1H), 4.60 (m, 1H), 2.31 (s, 3H), 1.40 (d, J=6.8 Hz, 1H), 1.27 (s, 12H), 1.08 (s, 9H) ppm. MS (ESI) m/z 366.2 (M+H)$^+$.

Example 1D (R)-1-(2-methyl-4-(4,4,5,5-tetramethyl-1,3,2-dioxaborolan-2-yl)phenyl)ethanamine A 3 L reactor was charged with Example 1C (250 g, 680 mmol) and ethyl acetate (750 mL) at 20° C. The mixture was chilled to 0° C. To the mixture was added hydrogen chloride in ethyl acetate (4 M, 750 mL) at 0° C. The reaction mixture was stirred for 2 hours at 20° C. The mixture was filtered, and the solid product was triturated in ethyl acetate, filtered, and dried under reduced pressure to afford the crude title compound as a hydrochloride salt. $^1$H NMR (400 MHz, dimethyl sulfoxide-$d_6$): 8.62 (br s, 3H), 7.52-7.60 (m, 3H), 4.51-4.54 (br d, J=5.2 Hz, 1H), 2.35 (s, 3H), 1.46 (d, J=6.8 Hz, 3H), 1.28 (s, 12H) ppm. MS (ESI) m/z 262.1 (M+H)$^+$.

Example 1E (R)-3-(tert-butyl)-N-(1-(2-methyl-4-(4,4,5,5-tetramethyl-1,3,2-dioxaborolan-2-yl)phenyl)ethyl)-1,2,4-oxadiazole-5-carboxamide To a solution of Example 1D (20 g, 77 mmol) and methyl 3-(tert-butyl)-1,2,4-oxadiazole-5-carboxylate (31.0 g, 168 mmol) in ethanol (200 mL) was added triethylamine (64.0 mL, 459 mmol) at 20° C. The mixture was stirred at 65° C. for 16 hours, and then concentrated under reduced pressure to remove ethanol. Water was added to the mixture, and the mixture was extracted with ethyl acetate (three times). The combined organic layer was washed with saturated ammonium chloride aqueous solution (once) and brine (once), dried with sodium sulfate, and filtered. The filtrate was concentrated under reduced pressure to provide the crude material. The crude material was purified by column chromatography on silica gel, eluted with petroleum ether and ethyl acetate to provide the title compound. $^1$H NMR (400 MHz, dimethyl sulfoxide-$d_6$): δ ppm 9.83 (d, J=7.7 Hz, 1H), 7.53-7.43 (m, 3H), 5.28 (quin, J=7.1 Hz, 1H), 2.37 (s, 3H), 1.45 (d, J=7.0 Hz, 3H), 1.35 (s, 9H), 1.27 (s, 12H) ppm. MS (ESI) m/z 414.3 (M+H)$^+$.

Example 1F 4-(2-((tert-butyldimethylsilyl)oxy)ethyl)aniline

A 3 L reactor was charged with 2-(4-aminophenyl)ethan-1-ol (176 g, 1.28 mol), N,N-dimethylformamide (1.8 L), imidazole (91.7 g, 1.35 mol), and tert-butyldimethylsilyl chloride (222 g, 1.48 mol) at ambient temperature. The mixture was stirred at ambient temperature for 6 hours. To the mixture were added ethyl acetate (500 mL) and water (300 mL). The organic phase was separated, washed with brine (300 mL), dried with sodium sulfate, concentrated under reduced pressure, and the residue was subjected to flash column chromatography (eluted with petroleum ether and ethyl acetate) to provide the title compound. MS (ESI) m/z 252.2 (M+H)$^+$.

Example 1G 3-((4-(2-((tert-butyldimethylsilyl)oxy)ethyl)phenyl)amino)propanoic acid Example 1F (196 g, 0.78 mol) was charged into a 3 L reactor. To the mixture were added toluene (1.4 L) and acrylic acid (67.4 g, 0.94 mol). The reaction mixture was stirred at 110° C. for 12 hours under nitrogen. The mixture was concentrated under reduced pressure to dryness to provide crude title compound. MS (ESI) m/z 324.2 (M+H)$^+$.

Example 1H 4-(2,4-dioxotetrahydropyrimidin-1(2H)-yl)phenethyl acetate

To crude Example 1G (252 g, 0.78 mol)) were added acetic acid (1.8 L) and urea (46.8 g, 0.78 mol). The reaction mixture was stirred at 110° C. for 12 hours under nitrogen and was cooled to ambient temperature. To the mixture were added water (600 mL) and ethyl acetate (600 mL). The organic phase was separated, and the aqueous phase was extracted with ethyl acetate (600 mL). The combined organic phase was washed with brine, dried with sodium sulfate, filtered and the filtrate was concentrated under reduced pressure to dryness to provide crude title compound. MS (ESI) m/z 277.1 (M+H)$^+$.

Example 1I 1-(4-(2-hydroxyethyl)phenyl)dihydropyrimidine-2,4 (1H,3H)-dione

To crude Example 1H (176 g, 0.63 mol) was added 6 N aqueous HCl (1.23 L, 7.39 mol), and the mixture was stirred at ambient temperature for 6 hours. The reaction mixture was concentrated under reduced pressure to dryness, and the residue was triturated with ethanol/ethyl acetate (250 mL/250 mL) for 30 minutes. The material was isolated by filtration and dried under vacuum to provide crude title compound. MS (ESI) m/z 235.1 (M+H)$^+$.

Example 1J 1-(4-(2-iodoethyl)phenyl)dihydropyrimidine-2,4(1H, 3H)-dione

A 250 mL flask was charged with Example 1I (10.0 g, 0.04 mol) and dichloromethane (100 mL). In an ice bath, iodine (16.3 g, 0.06 mol) was added in small portions, followed by Ph$_3$P (16.8 g, 0.06 mol) in small portions, followed by imidazole (4.36 g, 0.06 mol) in small portions. The reaction mixture was then stirred at ambient temperature for 3 hours. The same reaction was duplicated seven times in parallel on the same scale. The reaction mixtures of the eight batches were combined and poured into a mixture of water (800 mL) and ethyl acetate (800 mL). After vigorously stirring, the organic phase was separated, filtered, dried with sodium sulfate, and filtered. The filtrate was concentrated under reduced pressure to provide the title compound. $^1$H NMR (400 MHz, dimethyl sulfoxide-$d_6$): δ ppm 10.34 (s, 1H), 7.32-7.24 (m, 4H), 3.75 (m, 2H), 3.49 (m, 2H), 3.13 (m, 2H), 2.72 (m, 2H) ppm. MS (ESI) m/z 345.0 (M+H)$^+$.

Example 1K tert-butyl (S)-3-methyl-4-(6-nitropyridin-3-yl)piperazine-1-carboxylate To a solution of 5-chloro-2-nitropyridine (30 g, 189 mmol) in toluene (600 mL) were added (S)-tert-butyl 3-methylpiperazine-1-carboxylate (37.9 g, 189 mmol), potassium phosphate (60.2 g, 284 mmol) and (R)-(+)-2,2'-bis(diphenylphosphino)-1,1'-binaphthyl (5.89 g, 9.46 mmol) at 20° C. The reaction vessel was evacuated and backfilled with argon three times and palladium(II) acetate (2.124 g, 9.46 mmol) was added in one portion at 20° C. The vessel was then evacuated and backfilled with argon three times again. The reaction mixture was warmed to 90° C. and stirred at 90° C. for 24 hours under argon atmosphere. The reaction mixture was cooled, filtered through a pad of diatomaceous earth, and washed with ethyl acetate. The filtrate was concentrated under reduced pressure, and the residue was purified by silica flash column (eluted with tetrahydrofuran in petroleum ether from 0% to 50%) to provide the title compound. $^1$H NMR (400 MHz, dimethyl sulfoxide-d$_6$): δ ppm 8.11-8.26 (m, 2H), 7.42 (dd, J=9.38, 3.00 Hz, 1H), 4.32 (br s, 1H), 3.93 (br s, 1H), 3.79 (br d, J=12.76 Hz, 2H), 3.14-3.29 (m, 2H), 3.06 (br s, 1H), 1.42 (s, 9H), 1.08 (d, J=6.63 Hz, 3H) ppm. MS (ESI) m/z 323.2 (M+H)$^+$.

Example 1L tert-butyl (S)-4-(6-aminopyridin-3-yl)-3-methylpiperazine-1-carboxylate To a suspension of Pd/C (10 wt %, 46.2 g, 43.4 mmol) in tetrahydrofuran (700 mL) was added Example 1K (70 g, 217 mmol), and the reaction mixture was stirred at ambient temperature for 24 hours under hydrogen (15 psi). The same reaction was duplicated on the same scale. The combined reaction mixture was filtered through a pad of diatomaceous earth, and the filtrate was concentrated under reduced pressure to give crude product. The material was triturated with petroleum ether and ethyl acetate, the resulting solid was filtered, and the filter cake was dried under vacuum to provide the title compound. $^1$H NMR (400 MHz, CDCl$_3$): δ ppm 7.62 (d, J=2.63 Hz, 1H), 7.20 (dd, J=8.76, 2.63 Hz, 1H), 6.40 (d, J=8.76 Hz, 1H), 5.56 (s, 2H), 3.55 (br d, J=11.38 Hz, 1H), 3.39 (br d, J=5.13 Hz, 2H), 3.17 (br s, 2H), 2.71-2.90 (m, 2H), 1.41 (s, 9H), 0.75 (d, J=6.25 Hz, 3H) ppm. MS (ESI) m/z 293.2 (M+H)$^+$.

Example 1M (R)-3-(tert-butyl)-N-(1-(4-(6-chloropyrimidin-4-yl)-2-methylphenyl)ethyl)-1,2,4-oxadiazole-5-carboxamide To a mixture of Example 1E (10 g, 24.19 mmol) and 4,6-dichloropyrimidine (7.21 g, 48.4 mmol) in tetrahydrofuran (400 mL) was added a solution of potassium phosphate (10.27 g, 48.4 mmol) in water (100 mL) at 20° C. The mixture was degassed at ambient temperature using a nitrogen stream, and to the mixture was added [1,1'-bis(diphenylphosphino)ferrocene]dichloro-palladium(II) palladium (II) (0.885 g, 1.210 mmol) under N$_2$. The reaction mixture was heated to 80° C. and stirred for 2 hours. The mixture was cooled, poured into water, and extracted with ethyl acetate (three times). The combined organic layer was washed with brine, dried over sodium sulfate, and filtered. The filtrate was concentrated under reduced pressure, and the residue was purified by silica column chromatography, eluting with tetrahydrofuran in petroleum ether to provide crude title compound. $^1$H NMR (400 MHz, dimethyl sulfoxide-d$_6$): δ ppm 9.93 (d, J=7.8 Hz, 1H), 9.07 (s, 1H), 8.30 (s, 1H), 8.09 (d, J=7.8 Hz, 1H), 7.63 (d, J=8.5 Hz, 1H), 5.33 (quin, J=7.2 Hz, 1H), 2.48-2.47 (m, 1H), 2.47 (s, 2H), 1.50 (d, J=7.0 Hz, 3H), 1.36 (s, 9H) ppm. MS (ESI) miz 400.1 (M+H)$^+$.

Example 1N tert-butyl (S)-4-(6-((6-(4-((R)-1-(3-(tert-butyl)-1,2,4-oxadiazole-5-carboxamido)ethyl)-3-methylphenyl)pyrimidin-4-yl)amino)pyridin-3-yl)-3-methylpiperazine-1-carboxylate To a solution of Example 1L (25 g, 86 mmol) in 1,4-dioxane (500 mL) were added Example 1M (34.2 g, 86 mmol), Cs$_2$CO$_3$ (55.7 g, 171 mmol) and (9,9-dimethyl-9H-xanthene-4, 5-diyl)bis(diphenylphosphine) (4.95 g, 8.55 mmol) at 20° C. The reaction vessel was evacuated and backfilled with argon, and that process was repeated three times. Thereafter (tris(dibenzylidene-acetone)dipalladium (0)) (3.91 g, 4.28 mmol) was added under argon. The reaction vessel was evacuated and backfilled with argon, and that process was repeated three times. The reaction mixture was heated to 100° C. and stirred at 100° C. for 16 hours. The reaction mixture was cooled, filtered through a pad of diatomaceous earth, and washed with ethyl acetate. The filtrate was concentrated under reduced pressure and the residue was purified by silica column chromatography, eluting with tetrahydrofuran in petroleum ether to provide the title compound. $^1$H NMR (400 MHz, dimethyl sulfoxide-d$_6$): δ ppm 10.02 (s, 1H), 9.89 (d, J=7.88 Hz, 1H), 8.71 (d, J=0.75 Hz, 1H), 7.97-8.10 (m, 2H), 7.79-7.88 (m, 2H), 7.71 (br d, J=8.50 Hz, 1H), 7.61 (d, J=8.63 Hz, 1H), 7.44 (dd, J=9.13, 2.88 Hz, 1H), 5.33 (quin, J=7.13 Hz, 1H), 3.73-3.92 (m, 2H), 3.60 (br d, J=11.51 Hz, 1H), 3.31 (br s, 1H), 3.16 (br d, J=11.88 Hz, 2H), 2.88-3.01 (m, 1H), 2.47 (s, 3H), 1.51 (d, J=6.88 Hz, 3H), 1.42 (s, 9H), 1.36 (s, 9H), 0.88 (d, J=6.38 Hz, 3H) ppm. MS (ESI) m/z 656.2 (M+H)$^+$.

Example 1O 3-(tert-butyl)-N—((R)-1-(2-methyl-4-(6-((5-((S)-2-methylpiperazin-1-yl)pyridin-2-yl)amino)pyrimidin-4-yl)phenyl)ethyl)-1,2,4-oxadiazole-5-carboxamide To a solution of Example 1N (32 g, 48.8 mmol) in dioxane (300 mL) was added hydrochloride (4 N in dioxane, 300 mL) drop-wise. The reaction mixture was stirred at ambient temperature for 2 hours. The reaction mixture was filtered to isolate the crude material, which was dried under vacuum. The crude material was diluted with water (300 mL), and to the mixture was added saturated sodium bicarbonate aqueous solution to adjust the pH to 8. The mixture was extracted with ethyl acetate (twice), dried over anhydrous sodium sulfate, and filtered. The filtrate was concentrated under reduced pressure to provide the title compound. $^1$H NMR (400 MHz, dimethyl sulfoxide-d$_6$): δ ppm 10.00 (s, 1H), 9.88 (d, J=7.78 Hz, 1H), 8.70 (d, J=0.88 Hz, 1H), 8.04 (br s, 1H), 8.00 (d, J=2.89 Hz, 1H), 7.79-7.89 (m, 2H), 7.71 (br d, J=8.66 Hz, 1H), 7.61 (d, J=8.66 Hz, 1H) 7.43 (dd, J=9.16, 2.89 Hz, 1H) 5.33 (quin, J=7.12 Hz, 1H) 3.67-3.81 (m, 2H), 3.67-3.81 (m, 1H), 3.67-3.81 (m, 1H), 3.08-3.17 (m, 1H), 2.89-3.06 (m, 3H), 2.74-2.89 (m, 2H), 2.47 (s, 3H), 1.51 (d, J=7.03 Hz, 3H), 1.36 (s, 9H), 0.96 (d, J=6.53 Hz, 3H) ppm. MS (ESI) m/z 556.2 (M+H)$^+$.

Example 1P 3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-methylphenyl}ethyl]-1,2,4-oxadiazole-5-carboxamide To a solution of Example 1O (24.7 g, 44.5 mmol) in acetonitrile (500 mL) were added Example 1J (18.36 g, 53.3 mmol), N,N-diisopropylethylamine (46.6 mL, 267 mmol) and sodium iodide (19.99 g, 133 mmol) at 20° C. Then the reaction mixture was stirred at 90° C. for 16 hours. The reaction mixture was cooled, poured into ice water, and filtered. The filter cake was triturated with ethyl acetate/tetrahydrofuran (twice). The material was dried under reduced pressure to provide the title compound. $^1$H NMR (400 MHz, dimethyl sulfoxide-$d_6$): δ ppm 10.33 (s, 1H), 9.99 (s, 1H), 9.89 (d, J=7.78 Hz, 1H), 8.70 (s, 1H), 7.96-8.09 (m, 2H), 7.80-7.87 (m, 2H), 7.70 (br d, J=7.65 Hz, 1H), 7.61 (d, J=8.66 Hz, 1H), 7.44 (dd, J=9.10, 2.82 Hz, 1H), 7.19-7.32 (m, 4H), 5.33 (br t, J=7.28 Hz, 1H), 3.86 (br d, J=6.65 Hz, 1H), 3.76 (t, J=6.65 Hz, 2H), 3.21 (br d, J=11.92 Hz, 1H), 2.99 (br t, J=9.35 Hz, 1H), 2.84 (br d, J=10.79 Hz, 1H), 2.77 (br t, J=7.47 Hz, 2H), 2.69 (br t, J=6.65 Hz, 3H), 2.56 (br s, 2H), 2.47 (s, 3H), 2.44 (br s, 1H), 2.26-2.37 (m, 1H), 1.51 (d, J=6.90 Hz, 3H), 1.36 (s, 9H), 0.99 (d, J=6.27 Hz, 3H) ppm. MS (ESI) m/z 772.2 (M+H)$^+$.

Example 2

3-tert-butyl-N-[(1R)-1-{4-[6-({5-[(2R)-4-{2-[4-(2,4-dioxo-1,3-diazinan-1-yl)phenyl]ethyl}-2-methylpiperazin-1-yl]pyridin-2-yl}amino)pyrimidin-4-yl]-2-methylphenyl}ethyl]-1,2,4-oxadiazole-5-carboxamide Example 2A tert-butyl (R)-3-methyl-4-(6-nitropyridin-3-yl)piperazine-1-carboxylate The title compound was prepared according to the procedure used for Example 1K, substituting (R)-tert-butyl 3-methylpiperazine-1-carboxylate for (S)-tert-butyl 3-methylpiperazine-1-carboxylate. $^1$H NMR (400 MHz, dimethyl sulfoxide-$d_6$): δ ppm 8.13-8.24 (m, 2H), 7.43 (dd, J=9.32, 3.06 Hz, 1H), 4.32 (br s, 1H), 3.85-4.03 (br s, 1H), 3.79 (br d, J=12.88 Hz, 2H), 2.97-3.30 (m, 3H), 1.43 (s, 9H), 1.08 (d, J=6.50 Hz, 3H) ppm. MS (ESI) m/z 323.2 (M+H)$^+$.

Example 2B tert-butyl (R)-4-(6-aminopyridin-3-yl)-3-methylpiperazine-1-carboxylate The title compound was prepared according to the procedure used for Example 1L, substituting Example 2A for Example 1K. $^1$H NMR (400 MHz, dimethyl sulfoxide-$d_6$): δ ppm 7.62 (d, J=2.63 Hz, 1H), 7.20 (dd, J=8.76, 2.75 Hz, 1H), 6.40 (d, J=8.76 Hz, 1H), 5.54 (s, 2H), 3.56 (br d, J=10.76 Hz, 1H), 3.40 (br s, 2H) 3.17 (br s, 2H), 2.71-2.88 (m, 2H), 1.41 (s, 9H), 0.76 (d, J=6.13 Hz, 3H) ppm. MS (ESI) m/z 293.1 (M+H)$^+$.

Example 2C tert-butyl (R)-4-(6-((6-(4-((R)-1-(3-(tert-butyl)-1,2,4-oxadiazole-5-carboxamido)ethyl)-3-methylphenyl)pyrimidin-4-yl)amino)pyridin-3-yl)-3-methylpiperazine-1-carboxylate The title compound was prepared according to the procedure used for Example 1N, substituting Example 2B for Example 1L. $^1$H NMR (400 MHz, dimethyl sulfoxide-$d_6$): δ ppm 9.99 (s, 1H), 9.87 (d, J=7.78 Hz, 1H), 8.70 (d, J=1.00 Hz, 1H), 7.98-8.07 (m, 2H), 7.79-7.88 (m, 2H), 7.71 (br d, J=9.16 Hz, 1H), 7.60 (d, J=8.66 Hz, 1H), 7.45 (dd, J=9.10, 2.82 Hz, 1H), 5.33 (quin, J=7.25 Hz, 1H), 3.75-3.88 (m, 2H), 3.56-3.65 (m, 1H), 3.11-3.22 (m, 2H), 2.90 (s, 1H), 2.52 (br s, 1H), 2.47 (s, 3H), 1.51 (d, J=7.03 Hz, 3H), 1.42 (s, 9H), 1.36 (s, 9H), 0.89 (d, J=6.40 Hz, 3H) ppm. MS (ESI) m/z 656.3 (M+H)$^+$.

Example 2D 3-(tert-butyl)-N—((R)-1-(2-methyl-4-(6-((5-((R)-2-methylpiperazin-1-yl)pyridin-2-yl)amino)pyrimidin-4-yl)phenyl)ethyl)-1,2,4-oxadiazole-5-carboxamide The title compound was prepared according to the procedure used for Example 1O, substituting Example 2C for Example 1N. $^1$H NMR (400 MHz, dimethyl sulfoxide-$d_6$): δ ppm 9.97 (s, 1H), 9.87 (d, J=7.78 Hz, 1H), 8.70 (d, J=1.00 Hz, 1H), 8.03 (br s, 1H), 7.98 (d, J=2.76 Hz, 1H), 7.80-7.87 (m, 2H), 7.69 (br d, J=8.66 Hz, 1H), 7.60 (d, J=8.66 Hz, 1H), 7.41 (dd, J=9.16, 2.89 Hz, 1H), 5.26-5.40 (m, 1H), 3.65-3.77 (m, 1H), 3.01-3.15 (m, 1H), 2.90-2.98 (m, 2H), 2.84-2.90 (m, 1H), 2.69-2.79 (m, 2H), 2.52 (br d, J=1.88 Hz, 1H), 2.47 (s, 3H), 1.51 (d, J=6.90 Hz, 3H), 1.36 (s, 9H), 0.96 (d, J=6.53 Hz, 3H) ppm. MS (ESI) m/z 556.4 (M+H)$^+$.

Example 2E 3-tert-butyl-N-[(1R)-1-{4-[6-({5-[(2R)-4-{2-[4-(2,4-dioxo-1,3-diazinan-1-yl)phenyl]ethyl}-2-methylpiperazin-1-yl]pyridin-2-yl}amino)pyrimidin-4-yl]-2-methylphenyl}ethyl]-1,2,4-oxadiazole-5-carboxamide The title compound was prepared according to the procedure used for Example 1P, substituting Example 2D for Example 1O. $^1$H NMR (400 MHz, dimethyl sulfoxide-$d_6$): δ ppm 10.31 (br s, 1H), 9.97 (s, 1H), 9.87 (br d, J=6.02 Hz, 1H), 8.70 (d, J=0.88 Hz, 1H), 7.94-8.10 (m, 2H), 7.78-7.89 (m, 2H), 7.70 (br d, J=8.03 Hz, 1H), 7.60 (d, J=8.66 Hz, 1H), 7.43 (dd, J=9.16, 2.89 Hz, 1H), 7.18-7.32 (m, 4H), 5.24-5.42 (m, 1H), 3.81-3.90 (m, 1H), 3.76 (t, J=6.65 Hz, 2H), 3.16-3.26 (m, 1H), 2.93-3.05 (m, 1H), 2.84 (br d, J=10.67 Hz, 1H), 2.73-2.81 (m, 2H), 2.67-2.73 (m, 3H), 2.53-2.62 (m, 2H), 2.47 (s, 3H), 2.44 (br s, 1H), 2.27-2.36 (m, 1H), 1.51 (d, J=7.03 Hz, 3H), 1.36 (s, 9H), 0.99 (d, J=6.40 Hz, 3H) ppm. MS (ESI) m/z 772.2 (M+H)$^+$.

Example 3

3-tert-butyl-N-{(1R)-1-[4-(6-{[5-(4-{2-[4-(2,4-dioxo-1,3-diazinan-1-yl)phenyl]ethyl}piperazin-1-yl)pyridin-2-yl]amino}pyrimidin-4-yl)-2-methylphenyl]ethyl}-1,2,4-oxadiazole-5-carboxamide Example 3A tert-butyl 4-(6-nitropyridin-3-yl)piperazine-1-carboxylate The title compound was prepared according to the procedure used for Example 1K, substituting tert-butyl piperazine-1-carboxylate for (S)-tert-butyl 3-methylpiperazine-1-carboxylate. MS (ESI) m/z 309.2 (M+H)$^+$.

Example 3B tert-butyl 4-(6-aminopyridin-3-yl)piperazine-1-carboxylate

The title compound was prepared according to the procedure used for Example 1L, substituting Example 3A for Example 1K. MS (ESI) m/z 279.3 (M+H)$^+$.

Example 3C tert-butyl (R)-4-(6-((6-(4-(1-(3-(tert-butyl)-1,2,4-oxadiazole-5-carboxamido)ethyl)-3-methylphenyl)pyrimidin-4-yl)amino)pyridin-3-yl)piperazine-1-carboxylate The title compound was prepared according to the procedure used for Example 1N, substituting Example 3B for Example 1L. $^1$H NMR (400 MHz, dimethyl sulfoxide-d$_6$): δ ppm 10.03 (s, 1H), 9.90 (d, J=7.8 Hz, 1H), 8.71 (s, 1H), 8.06 (br d, J=2.9 Hz, 2H), 7.85-7.80 (m, 2H), 7.71 (br d, J=8.0 Hz, 1H), 7.60 (d, J=8.6 Hz, 1H), 7.47 (dd, J=2.9, 9.1 Hz, 1H), 5.38-5.28 (m, 1H), 3.46 (br d, J=4.8 Hz, 4H), 3.12-3.02 (m, 4H), 2.47 (s, 3H), 1.51 (d, J=6.9 Hz, 3H), 1.42 (s, 9H), 1.37-1.34 (m, 9H) ppm. MS (ESI) m/z 642.4 (M+H)$^+$.

Example 3D (R)-3-(tert-butyl)-N-(1-(2-methyl-4-(6-((5-(piperazin-1-yl)pyridin-2-yl)amino)pyrimidin-4-yl)phenyl)ethyl)-1,2,4-oxadiazole-5-carboxamide The title compound was prepared according to the procedure used for Example 1O, substituting Example 3C for Example 1N. $^1$H NMR (400 MHz, dimethyl sulfoxide-d$_6$): δ ppm 10.01 (s, 1H), 9.89 (d, J=7.8 Hz, 1H), 8.71 (s, 1H), 8.14-7.95 (m, 2H), 7.89-7.77 (m, 2H), 7.71 (br d, J=8.4 Hz, 1H), 7.60 (d, J=8.8 Hz, 1H), 7.46 (dd, J=2.9, 9.1 Hz, 1H), 5.33 (quin, J=7.1 Hz, 1H), 3.19-3.11 (m, 4H), 3.05-2.96 (m, 4H), 2.47 (s, 3H), 1.51 (d, J=7.0 Hz, 3H), 1.36 (s, 9H) ppm. MS (ESI) m/z 542.3 (M+H)$^+$.

Example 3E 3-tert-butyl-N-{(1R)-1-[4-(6-{[5-(4-{2-[4-(2,4-dioxo-1,3-diazinan-1-yl)phenyl]ethyl}piperazin-1-yl)pyridin-2-yl]amino}pyrimidin-4-yl)-2-methylphenyl]ethyl}-1,2,4-oxadiazole-5-carboxamide The title compound was prepared according to the procedure used for Example 1P, substituting Example 3D for Example 1O. $^1$H NMR (500 MHz, dimethyl sulfoxide-d$_6$): δ ppm 10.34 (s, 1H), 9.99 (s, 1H), 9.88 (d, J=7.8 Hz, 1H), 8.70 (s, 1H), 8.08-8.00 (m, 2H) 7.85-7.80 (m, 2H), 7.69 (brs, 1H), 7.63-7.58 (m, 1H), 7.47 (dd, J=9.1, 3.0 Hz, 1H), 7.30-7.21 (m, J=8.3 Hz, 4H), 5.33 (p, J=7.1 Hz, 1H), 3.76 (t, J=6.7 Hz, 2H), 3.14 (brs, 4H), 2.79 (brs, 2H), 2.70 (t, J=6.7 Hz, 2H), 2.61 (brs, 5H), 2.47 (s, 3H), 1.51 (d, J=7.0 Hz, 3H), 1.36 (s, 9H) ppm. MS (ESI) m/z 758.3 (M+H)$^+$.

Example 4

3-tert-butyl-N-[(1R)-1-{4-[6-({5-[(2S)-4-{2-[4-(2,4-dioxo-1,3-diazinan-1-yl)-3-fluorophenyl]ethyl}-2-methylpiperazin-1-yl]pyridin-2-yl}amino)pyrimidin-4-yl]-2-methylphenyl}ethyl]-1,2,4-oxadiazole-5-carboxamide

Example 4A (E)-2-(3-fluoro-4-nitrophenyl)-N,N-dimethylethen-1-amine

A mixture of 2-fluoro-4-methyl-1-nitrobenzene (1.50 kg, 9.63 mol) and N,N-dimethylformamide-dimethylacetal (1.72 kg, 14.5 mol, 1.92 L) in N,N-dimethylformamide (2.4 L) was degassed and purged with nitrogen three times, and the mixture was stirred at 120° C. (internal reading) for 2 hours under nitrogen. The reaction mixture was concentrated under reduced pressure. The crude material was triturated with petroleum ether/tert-butyl methyl ether (1:1, 10.0 L) and filtered. The filter cake was washed with petroleum ether/tert-butyl methyl ether (1:1, 2.0 L) and dried under vacuum to provide the title compound. $^1$H NMR (400 MHz, CDCl$_3$): δ ppm 7.92 (t, J=8.4 Hz, 1H), 7.03 (d, J=13.6 Hz, 1H), 6.89-6.84 (m, 2H), 5.05 (d, J=13.2 Hz, 1H), 2.95 (s, 6H) ppm.

Example 4B 2-(3-fluoro-4-nitrophenyl)ethan-1-ol

To aqueous hydrochloric acid (4 M, 7.50 L) was added Example 4A (1.00 kg, 4.76 mol) in small portions at ambient temperature. The mixture was stirred at ambient temperature for 12 hours and extracted with 2-methyl tetrahydrofuran (3.0 L×7). The combined organic phase was washed with brine (5.0 L) and dried with sodium sulfate. After filtration, the filtrate was concentrated to 10 L in volume under reduced pressure, and chilled in an ice bath. To the mixture was added sodium hydroborate (214 g, 5.68 mol) in small portions in the ice bath, and the reaction mixture was stirred at ambient temperature for 16 hours. The mixture was chilled in an ice bath and quenched with aqueous 0.5 N hydrochloric acid (5.0 L). The organic phase was separated, washed with brine (3.0 L), dried with sodium sulfate, and filtered. The filtrate was concentrated under reduced pressure to provide crude title compound.

Example 4C tert-butyl(3-fluoro-4-nitrophenethoxy)dimethylsilane

To a mixture of crude Example 4B (660 g, 3.56 mol) and imidazole (364 g, 5.34 mol) in tetrahydrofuran (4.4 L) was added tert-butyldimethylsilyl chloride (804 g, 5.34 mol, 654 mL) in portions at ambient temperature. The mixture was stirred at ambient temperature for 12 hours, quenched by addition of water (3.0 L), and diluted with ethyl acetate (3.0 L). The organic layer was separated, washed with brine (5.0 L), dried over sodium sulfate, and filtered. The filtrate was concentrated under reduced pressure. The residue was subjected to silica flash column chromatography (petroleum ether and ethyl acetate) to provide the title compound. $^1$H NMR (400 MHz, CDCl$_3$): δ ppm 7.92-8.05 (m, 1H), 7.11-7.20 (m, 2H), 3.79-3.92 (m, 2H), 2.80-2.93 (m, 2H), 0.80 (s, 9H), −0.09 (s, 6H) ppm.

Example 4D 4-(2-((tert-butyldimethylsilyl)oxy)ethyl)-2-fluoroaniline

To a suspension of Pd/C (2.346 g, 2.204 mmol) in tetrahydrofuran (100 mL) was added Example 4C (5.5 g, 18.37 mmol) at 25° C. The resulting mixture was stirred at 25° C. for 12 hours. The reaction mixture was filtered, and the filtrate was concentrated at 40° C. under reduced pressure to provide the title compound. MS (ESI) m/z 270.1 (M+H)$^+$.

Example 4E 3-((4-(2-((tert-butyldimethylsilyl)oxy)ethyl)-2-fluorophenyl)amino)propanoic acid To a solution of Example 4D (2.5 g, 9.28 mmol) in toluene (25 mL) was added acrylic acid (0.802 g, 11.13 mmol). The reaction mixture was heated to 120° C. and stirred for 16 hours. The reaction mixture was cooled to 20° C. and was concentrated under reduced pressure to provide crude title compound. MS (ESI) m/z 342.1 (M+H)$^+$.

Example 4F 4-(2,4-dioxotetrahydropyrimidin-1(2H)-yl)-3-fluorophenethyl acetate To a solution of Example 4E (3 g, 8.78 mmol) in acetic acid (30 mL) was added urea (1.583 g, 26.4 mmol). The reaction mixture was heated to 120° C. and stirred for 16 hours. The reaction mixture was cooled to 20° C. and was concentrated under reduced pressure. The crude material was purified by preparative HPLC (Phenomenex Luna® C18 column, 50*250 mm, 10 µm, using 0.1% formic acid in water and acetonitrile as mobile phases) to provide the title compound. MS (ESI) m/z 295.1 (M+H)$^+$.

Example 4G 1-(2-fluoro-4-(2-hydroxyethyl)phenyl)dihydropyrimidine-2,4(1H,3H)-dione To a solution of Example 4F (1.1 g, 3.74 mmol) in water (1 mL) was added concentrated hydrochloric acid (37%, 1 mL) at 20° C. The reaction mixture was stirred at 20° C. for 12 hours. The reaction mixture was concentrated under reduced pressure to provide the title compound. MS (ESI) m/z 253.1 (M+H)$^+$.

Example 4H 1-(4-(2-bromoethyl)-2-fluorophenyl)dihydropyrimidine-2,4(1H,3H)-dione To a solution of Example 4G (0.3 g, 1.189 mmol) in dichloromethane (20 mL) was added CBr$_4$ (0.789 g, 2.379 mmol) followed by Ph$_3$P (0.624 g, 2.379 mmol) at 0° C. The reaction mixture was stirred at 20° C. for 12 hours. The reaction mixture was concentrated at 40° C. under reduced pressure. The residue was purified by silica flash column chromatography (ethyl acetate in petroleum ether, 0-100%) to provide the title compound. $^1$H NMR (400 MHz, dimethyl sulfoxide-d$_6$): δ ppm 10.47 (s, 1H), 7.37 (t, J=8.0 Hz, 1H), 7.27 (br d, J=11.2 Hz, 1H), 7.16 (br d, J=7.6 Hz, 1H), 3.77 (t, J=7.2 Hz, 2H), 3.70 (t, J=6.8 Hz, 2H), 3.16 (t, J=7.2 Hz, 2H), 2.71 (t, J=6.8 Hz, 2H) ppm. MS (ESI) m/z 315.0, 317.0 (M+H)$^+$.

Example 4I 3-tert-butyl-N-[(1R)-1-{4-[6-({5-[(2S)-4-{2-[4-(2,4-dioxo-1,3-diazinan-1-yl)-3-fluorophenyl]ethyl}-2-methylpiperazin-1-yl]pyridin-2-yl}amino)pyrimidin-4-yl]-2-methylphenyl}ethyl]-1,2,4-oxadiazole-5-carboxamide To a solution of Example 10 (80 mg, 0.14 mmol) in N,N-dimethylformamide (1 mL) were added Example 4H (54 mg, 0.17 mmol), sodium iodide (65 mg, 0.43 mmol) and N,N-diisopropylethylamine (56 mg, 0.43 mmol). The mixture was stirred at 80° C. for 16 hours. The mixture was cooled to ambient temperature and filtered. The filtrate was directly subjected to reverse phase preparative HPLC to provide the title compound (Gilson GX-281 system, Waters™ Xbridge C18 column, 30×100 mm×10 µm, 10 mM ammonium bicarbonate in water and acetonitrile as mobile phases). $^1$H NMR (400 MHz, dimethyl sulfoxide-d$_6$): δ ppm 10.46 (s, 1H), 9.99 (s, 1H), 9.89 (d, J=7.89 Hz, 1H), 8.70 (d, J=0.66 Hz, 1H), 7.96-8.08 (m, 2H), 7.80-7.86 (m, 2H), 7.66-7.75 (m, 1H), 7.60 (d, J=8.77 Hz, 1H), 7.44 (dd, J=9.21, 2.85 Hz, 1H), 7.33 (t, J=8.11 Hz, 1H), 7.24 (dd, J=11.62, 1.53 Hz, 1H), 7.15 (dd, J=8.11, 1.53 Hz, 1H), 5.33 (t, J=7.34 Hz, 1H), 3.82-3.91 (m, 1H), 3.69 (t, J=6.69 Hz, 2H), 3.21 (br d, J=11.84 Hz, 1H), 2.98 (br t, J=9.32 Hz, 1H), 2.77-2.83 (m, 2H), 2.69-2.72 (m, 2H), 2.53-2.64 (m, 2H), 2.52 (d, J=1.75 Hz, 2H), 2.47 (s, 3H), 2.41-2.46 (m, 1H), 2.26-2.32 (m, 1H), 1.51 (d, J=7.02 Hz, 3H), 1.36 (s, 9H), 0.98 (d, J=6.36 Hz, 3H) ppm. LC/MS (ESI+) m/z 790.3 (M+H)$^+$.

Example 5

3-tert-butyl-N-[(1R)-1-{4-[6-({5-[(2R)-4-{2-[4-(2,4-dioxo-1,3-diazinan-1-yl)-3-fluorophenyl]ethyl}-2-methylpiperazin-1-yl]pyridin-2-yl}amino)pyrimidin-4-yl]-2-methylphenyl}ethyl]-1,2,4-oxadiazole-5-carboxamide To a solution of Example 2D (100 mg, 0.18 mmol) in N,N-dimethylformamide (2 mL) were added Example 4H (68 mg, 0.22 mmol), sodium iodide (81 mg, 0.54 mmol) and N,N-diisopropylethylamine (70 mg, 0.54 mmol). The mixture was stirred at 80° C. for 16 hours. The mixture was cooled to ambient temperature and filtered. The filtrate was directly subjected to reverse phase preparative HPLC to isolate the title compound (Gilson GX-281 system, Phenomenex Luna® C18 column, 30×75 mm×3 µm, 0.1% formic acid in water and acetonitrile as mobile phases). $^1$H NMR (400 MHz, dimethyl sulfoxide-d$_6$): δ ppm 10.45 (s, 1H), 9.99 (s, 1H), 9.88 (d, J=7.82 Hz, 1H), 8.70 (s, 1H), 7.98-8.07 (m, 2H), 7.79-7.87 (m, 2H), 7.66-7.74 (m, 1H), 7.60 (d, J=8.68 Hz, 1H), 7.40-7.48 (m, 1H), 7.33 (t, J=8.19 Hz, 1H), 7.21-7.28 (m, 1H), 7.15 (d, J=8.31 Hz, 1H), 5.24-5.44 (m, 1H), 3.76-3.97 (m, 1H), 3.69 (t, J=6.66 Hz, 2H), 3.13-3.26 (m, 2H), 2.94-3.06 (m, 1H), 2.77-2.92 (m, 3H), 2.71 (t, J=6.66 Hz, 3H), 2.56-2.65 (m, 1H), 2.47 (s, 3H), 2.33-2.46

(m, 2H), 1.51 (d, J=6.85 Hz, 3H), 1.36 (s, 9H), 0.98 (d, J=6.24 Hz, 3H) ppm. LC/MS (ESP): m/z 790.2 (M+H)$^+$.

Example 6

3-tert-butyl-N-[(1R)-1-{4-[6-({5-[(2S)-4-{2-[4-(2,4-dioxo-1,3-diazinan-1-yl)phenyl]ethyl}-2-ethylpiperazin-1-yl]pyridin-2-yl}amino)pyrimidin-4-yl]-2-methylphenyl}ethyl]-1,2,4-oxadiazole-5-carboxamide

Example 6A (S)-tert-butyl 3-ethyl-4-(6-nitropyridin-3-yl)piperazine-1-carboxylate 5-Fluoro-2-nitropyridine (1.00 g, 7.04 mmol) and (S)-tert-butyl 3-ethylpiperazine-1-carboxylate (1.96 g, 9.15 mmol) were dissolved in N,N-dimethylformamide, and potassium carbonate (2.92 g, 21.11 mmol) was added. The reaction mixture was stirred at 70° C. for 15 hours and concentrated under reduced pressure to remove most of the solvent. The residue was diluted with dichloromethane, washed with water, dried with sodium sulfate, and filtered. The filtrate was concentrated under reduced pressure to yield the crude title compound. $^1$H NMR (400 MHz, dimethyl sulfoxide-d$_6$): δ ppm 8.21 (d, J=2.88 Hz, 1H), 8.15 (d, J=9.26 Hz, 1H), 7.42 (dd, J=9.32, 2.94 Hz, 1H), 3.89-4.17 (m, 3H), 3.82 (br d, J=12.88 Hz, 1H), 2.90-3.27 (m, 3H), 1.47-1.69 (m, 2H), 1.42 (s, 9H), 0.90 (br s, 3H) ppm. LC/MS (ESP): m/z 337.0 (M+H)$^+$.

Example 6B (S)-tert-butyl 4-(6-aminopyridin-3-yl)-3-ethylpiperazine-1-carboxylate Example 6A (2.0 g, 5.95 mmol) was dissolved in methanol (200 mL). To the mixture was added Pd/C (10 wt %, 0.32 g, 3.0 mmol). The reaction mixture was hydrogenated using a hydrogen balloon at ambient temperature for 2 days. The mixture was filtered through diatomaceous earth, and the solid cake was washed with methanol and ethyl acetate. The filtrate was concentrated under reduced pressure to afford the crude title compound. $^1$H NMR (400 MHz, dimethyl sulfoxide-d$_6$): δ ppm 7.59 (br d, J=2.01 Hz, 1H), 7.12-7.21 (m, 1H), 6.40 (d, J=8.78 Hz, 1H), 5.46 (br s, 2H), 3.47-3.76 (m, 2H), 2.98-3.23 (m, 2H), 2.85 (br d, J=4.64 Hz, 2H), 2.52 (br d, J=1.88 Hz, 1H), 1.41 (s, 9H), 1.35 (s, 1H), 1.25 (br s, 1H), 0.77 (br t, J=7.22 Hz, 3H) ppm. LC/MS (ESP): m/z 307.2 (M+H)$^+$.

Example 6C tert-butyl (S)-4-(6-((6-(4-((R)-1-(3-(tert-butyl)-1,2,4-oxadiazole-5-carboxamido)ethyl)-3-methylphenyl)pyrimidin-4-yl)amino)pyridin-3-yl)-3-ethylpiperazine-1-carboxylate To a solution of Example 1E (300 mg, 0.75 mmol) in 1,4-dioxane (6 mL) were added Example 6B (253 mg, 0.83 mmol), Pd$_2$(dba)$_3$ (CAS 52409-22-0, 34 mg, 0.038 mmol), XantPhos (CAS 161265-03-8, 43 mg, 0.075 mmol) and cesium carbonate (489 mg, 1.50 mmol). The mixture was degassed using argon stream and stirred at 100° C. for 16 hours. The reaction mixture was cooled, diluted with ethyl acetate, and filtered through diatomaceous earth. The filtrate was concentrated under reduced pressure and purified by silica chromatography using ethyl acetate and petroleum ether to afford the title compound. $^1$H NMR (400 MHz, dimethyl sulfoxide-d$_6$): δ ppm 9.98 (s, 1H), 9.89 (d, J=7.78 Hz, 1H), 8.70 (s, 1H), 7.96-8.07 (m, 2H), 7.80-7.86 (m, 2H), 7.66-7.74 (m, 1H), 7.60 (d, J=8.66 Hz, 1H), 7.38-7.48 (m, 1H), 5.33 (quin, J=7.09 Hz, 1H), 3.90 (br d, J=11.04 Hz, 2H), 3.60 (br dd, J=6.53, 3.01 Hz, 1H), 3.12-3.29 (m, 2H), 2.89-3.05 (m, 2H), 2.47 (s, 3H), 1.61 (s, 1H), 1.51 (br d, J=6.90 Hz, 3H), 1.42 (s, 9H), 1.36 (s, 9H), 1.21-1.31 (m, 1H), 0.86 (br s, 3H) ppm. LC/MS (ESI+): m/z 670.4 (M+H)$^+$.

Example 6D 3-(tert-butyl)-N—((R)-1-(4-(6-((5-((S)-2-ethylpiperazin-1-yl)pyridin-2-yl)amino)pyrimidin-4-yl)-2-methylphenyl)ethyl)-1,2,4-oxadiazole-5-carboxamide To a solution of Example 6C (150 mg, 0.22 mmol) in 1,4-dioxane (3 mL) was added hydrochloride (4N in dioxane, 3 mL) dropwise at ambient temperature. The mixture was stirred for 2 hours, concentrated under reduced pressure, diluted with water (5 mL), and treated with saturated sodium carbonate aqueous solution to adjust the pH to 8. The mixture was extracted with ethyl acetate (15 mL, three times), and organic phase was dried over sodium sulfate and filtered. The filtrate was concentrated under reduced pressure to afford the crude title compound. $^1$H NMR (400 MHz, dimethyl sulfoxide-d$_6$): δ ppm 9.94 (s, 1H), 9.89 (d, J=7.78 Hz, 1H), 8.69 (s, 1H), 7.92-8.05 (m, 2H), 7.80-7.87 (m, 2H), 7.63-7.72 (m, 1H), 7.60 (d, J=8.66 Hz, 1H), 7.37 (dd, J=9.03, 2.89 Hz, 1H), 5.33 (quin, J=7.09 Hz, 1H), 3.45 (br dd, J=6.71, 2.45 Hz, 1H), 3.09-3.17 (m, 1H), 2.80-2.94 (m, 4H), 2.66-2.74 (m, 1H), 2.47 (s, 3H), 1.75 (ddd, J=13.61, 9.47, 7.40 Hz, 1H), 1.51 (d, J=6.90 Hz, 3H), 1.36 (s, 9H), 1.22-1.30 (m, 1H), 0.79 (t, J=7.47 Hz, 3H) ppm. LC/MS (ESI+): m/z 570.4 (M+H)$^+$.

Example 6E 3-tert-butyl-N-[(1R)-1-{4-[6-({5-[(2S)-4-{2-[4-(2,4-dioxo-1,3-diazinan-1-yl)phenyl]ethyl}-2-ethylpiperazin-1-yl]pyridin-2-yl}amino)pyrimidin-4-yl]-2-methylphenyl}ethyl]-1,2,4-oxadiazole-5-carboxamide Example 6D (480 mg, 0.79 mmol), Example 1J (327 mg, 0.95 mmol), N,N-diisopropylethylamine (277 μL, 1.58 mmol) and potassium iodide (657 mg, 3.96 mmol) were mixed in N,N-dimethylformamide (8 mL). The mixture was stirred at 80° C. for 4 hours. The mixture was cooled, quenched with a few drops of formic acid, and directly subjected to reverse phase preparative HPLC to isolate the title compound (Phenomenex Gemini® AXA C18 column, 30×250 mm×5 μm, 0.1% formic acid in water and acetonitrile as mobile phases). $^1$H NMR (500 MHz, dimethyl sulfoxide-d$_6$): δ ppm 9.89 (s, 1H), 9.53 (s, 1H), 9.38 (d, J=7.6 Hz, 1H), 8.64 (d, J=1.1 Hz, 1H), 7.94 (dd, J=11.8, 2.1 Hz, 2H), 7.84-7.78 (m, 2H), 7.64 (d, J=9.0 Hz, 1H), 7.58 (d, J=8.8 Hz, 1H), 7.33 (dd, J=9.1, 3.1 Hz, 1H), 7.28-7.18 (m, 4H), 5.34 (p, J=7.1 Hz, 1H), 3.73 (t, J=6.7 Hz, 2H), 3.53 (s, 1H), 3.24 (d, J=12.2 Hz, 1H), 3.10-3.02 (m, 1H), 2.79 (ddt, J=14.1, 7.8, 3.6 Hz, 4H), 2.68 (t, J=6.7 Hz, 2H), 2.60 (s, 2H), 2.45 (s, 3H), 2.41-2.27 (m, 3H), 1.73-1.59 (m, 1H), 1.52 (d, J=7.0 Hz, 3H), 1.35 (s, 9H), 0.79 (t, J=7.4 Hz, 3H) ppm. LC/MS (ESI+): m/z 786.7 (M+H)$^+$.

Example 7

3-tert-butyl-N-[(1R)-1-{4-[6-({5-[(2S)-4-{2-[4-(2,4-dioxo-1,3-diazinan-1-yl)-3-fluorophenyl]ethyl}-2-ethylpiperazin-1-yl]pyridin-2-yl}amino)pyrimidin-4-yl]-2-methylphenyl}ethyl]-1,2,4-oxadiazole-5-carboxamide Example 6D (120 mg, 0.21 mmol), Example 4H (100 mg, 0.32 mmol), N,N-diisopropylethylamine (184 μL, 1.05 mmol) and sodium iodide (95 mg, 0.63 mmol) were mixed in acetonitrile (2.4 mL). The mixture was stirred at 80° C. for 16 hours. The mixture was cooled, quenched with a few drops of formic acid, and directly subjected to reverse phase preparative HPLC to isolate the title compound (Phenomenex Luna® C18 column, 30×75 mm×3 μm, 0.1% formic acid in water and acetonitrile as mobile phases). $^1$H NMR (400 MHz, dimethyl sulfoxide-d$_6$): δ ppm 10.46 (s, 1H), 9.96 (s, 1H), 9.89 (d, J=7.75 Hz, 1H), 8.69 (s, 1H), 7.94-8.05 (m, 2H), 7.80-7.86 (m, 2H), 7.64-7.73 (m, 1H), 7.60 (d, J=8.63 Hz, 1H), 7.37-7.44 (m, 1H), 7.33 (t, J=8.19 Hz, 1H), 7.21-7.28 (m, 1H), 7.08-7.17 (m, 1H), 5.25-5.41 (m, 1H), 3.68 (t, J=6.63 Hz, 2H), 3.57-3.65 (m, 1H), 3.00 (br t, J=10.57 Hz, 1H), 2.86-2.95 (m, 2H), 2.81 (br d, J=6.38 Hz, 2H), 2.71 (br t, J=6.63 Hz, 2H), 2.60-2.65 (m, 1H), 2.47 (br s, 5H), 2.21-2.31 (m, 2H), 1.62-1.76 (m, 1H), 1.51 (d, J=7.00 Hz, 3H), 1.36 (s, 9H), 1.22-1.31 (m, 1H), 0.81 (br t, J=7.38 Hz, 3H) ppm. LC/MS (ESI+): m/z 804.3 (M+H)$^+$.

Example 8

3-tert-butyl-N-[(1R)-1-{4-[6-({5-[(2R)-4-{2-[4-(2,4-dioxo-1,3-diazinan-1-yl)phenyl]ethyl}-2-ethylpiperazin-1-yl]pyridin-2-yl}amino)pyrimidin-4-yl]-2-methylphenyl}ethyl]-1,2,4-oxadiazole-5-carboxamide

Example 8A (R)-tert-butyl 3-ethyl-4-(6-nitropyridin-3-yl)piperazine-1-carboxylate The title compound was prepared according to the procedure used for Example 6A, substituting (R)-tert-butyl 3-ethylpiperazine-1-carboxylate for (S)-tert-butyl 3-ethylpiperazine-1-carboxylate. LC/MS (EST): m/z 337.0 (M+H)$^+$.

Example 8B (R)-tert-butyl 4-(6-aminopyridin-3-yl)-3-ethylpiperazine-1-carboxylate The title compound was prepared according to the procedure used for Example 6B, substituting Example 8A for Example 6A. LC/MS (ESI$^+$): m/z 307.2 (M+H)$^+$.

Example 8C tert-butyl (R)-4-(6-((6-(4-((R)-1-(3-(tert-butyl)-1,2,4-oxadiazole-5-carboxamido)ethyl)-3-methylphenyl)pyrimidin-4-yl)amino)pyridin-3-yl)-3-ethylpiperazine-1-carboxylate The title compound was prepared according to the procedure used for Example 6C, substituting Example 8B for Example 6B. LC/MS (ESI+): m/z 670.1 (M+H)$^+$.

Example 8D 3-(tert-butyl)-N—((R)-1-(4-(6-((5-((R)-2-ethylpiperazin-1-yl)pyridin-2-yl)amino)pyrimidin-4-yl)-2-methylphenyl)ethyl)-1,2,4-oxadiazole-5-carboxamide The title compound was prepared according to the procedure used for Example 6D, substituting Example 8C for Example 6C. LC/MS (ESI+): m/z 570.7 (M+H)$^+$.

Example 8E 3-tert-butyl-N-[(1R)-1-{4-[6-({5-[(2R)-4-{2-[4-(2,4-dioxo-1,3-diazinan-1-yl)phenyl]ethyl}-2-ethylpiperazin-1-yl]pyridin-2-yl}amino)pyrimidin-4-yl]-2-methylphenyl}ethyl]-1,2,4-oxadiazole-5-carboxamide The title compound was prepared according to the procedure used for Example 6E, substituting Example 8D for Example 6D. $^1$H NMR (400 MHz, dimethyl sulfoxide-d$_6$): δ 9.95 (s, 1H), 9.79 (s, 1H), 9.40 (d, J=7.5 Hz, 1H), 8.70 (s, 1H), 8.09 (s, 1H), 7.99 (s, 1H), 7.82 (d, J=7.8 Hz, 2H), 7.74 (d, J=8.7 Hz, 1H), 7.59 (d, J=7.9 Hz, 1H), 7.51 (s, 1H), 7.33-7.28 (m, 4H), 5.34 (p, J=7.1 Hz, 1H), 3.75 (t, J=6.7 Hz, 2H), 3.40-3.32 (m, 4H), 3.28 (s, 2H), 3.20 (s, 1H), 3.10-3.03 (m, 1H), 3.00-2.90 (m, 3H), 2.69 (t, J=6.7 Hz, 2H), 2.46-2.45 (m, 5H), 1.52 (d, J=6.9 Hz, 3H), 1.35 (s, 9H), 0.83 (t, J=7.1 Hz, 3H) ppm. LC/MS (ESI+): m/z 786.9 (M+H)$^+$.

Example 9

3-tert-butyl-N-{(1R)-1-[4-(6-{{5-(4-{2-[4-(2,4-dioxo-1,3-diazinan-1-yl)phenyl]ethyl}-2,2-dimethylpiperazin-1-yl)pyridin-2-yl}amino}pyrimidin-4-yl)-2-methylphenyl]ethyl}-1,2,4-oxadiazole-5-carboxamide

Example 9A tert-butyl 3,3-dimethyl-4-(6-nitropyridin-3-yl)piperazine-1-carboxylate 5-Bromo-2-nitropyridine (5.68 g, 28.0 mmol) and tert-butyl 3,3-dimethylpiperazine-1-carboxylate (3.0 g, 14.00 mmol) were dissolved in dioxane (150 mL). To the mixture were added cesium carbonate (9.12 g, 28.0 mmol), BINAP ((R/S)-2,2'-bis(diphenylphosphino)-1,1'-binaphthyl, 0.872 g, 1.40 mmol) and tris(dibenzylideneacetone)dipalladium(0) (1.282 g, 1.40 mmol). The reaction mixture was stirred 120° C. for 15 hours under nitrogen atmosphere. The mixture was cooled and filtered. The filtrate was concentrated under reduced pressure, and the residue was purified using silica chromatography (ethyl acetate and hexane) to afford the title compound. LC/MS (ESI+) m/z 336.9 (M+H)+.

Example 9B tert-butyl 4-(6-aminopyridin-3-yl)-3,3-dimethylpiperazine-1-carboxylate Example 9A (1.1 g, 3.27 mmol) was dissolved in methanol (100 mL). To the mixture was added Pd/C (10 wt %, 0.17 g, 1.64 mmol). The reaction mixture was hydrogenated using a hydrogen balloon at ambient temperature for 2 days. The mixture was filtered through diatomaceous earth, and the filter cake was washed with methanol and ethyl acetate. The filtrate was concentrated under reduced pressure to afford the crude title compound. LC/MS (ESI+) m/z 307.2 (M+H)+.

Example 9C tert-butyl (R)-4-(6-((6-(4-(1-(3-(tert-butyl)-1,2,4-oxadiazole-5-carboxamido)ethyl)-3-methylphenyl)pyrimidin-4-yl)amino)pyridin-3-yl)-3,3-dimethylpiperazine-1-carboxylate A stirred mixture of Example 9B (400 mg, 1.30 mmol), Example 1E (522 mg, 1.30 mmol), racemic BINAP-Pd-G3 (CAS 2151915-22-7, 130 mg, 0.13 mmol) and cesium carbonate (1276 mg, 3.92 mmol) in 1,4-dioxane (6.5 mL) was heated at 105° C. in a Biotage™ Initiator+microwave synthesizer for 2 hours. The mixture was cooled and filtered. The filtrate was concentrated under reduced pressure and purified using silica chromatography with ethyl acetate and hexane to provide the title compound. LC/MS (ESI+): m/z 670.6 (M+H)+.

Example 9D (R)-3-(tert-butyl)-N-(1-(4-(6-((5-(2,2-dimethylpiperazin-1-yl)pyridin-2-yl)amino)pyrimidin-4-yl)-2-methylphenyl)ethyl)-1,2,4-oxadiazole-5-carboxamide Example 9C (845 mg, 1.26 mmol) was dissolved in 1,4-dioxane (3 mL), and to the mixture was added hydrochloride (4 N in 1,4-dioxane, 1.6 mL). The mixture was stirred at ambient temperature for 2 hours and concentrated under reduced pressure to afford the crude title compound as a hydrochloride salt. LC/MS (ESI+): m/z 570.7 (M+H)+.

Example 9E 3-tert-butyl-N-{(1R)-1-[4-(6-{[5-(4-{2-[4-(2,4-dioxo-1,3-diazinan-1-yl)phenyl]ethyl}-2,2-dimethylpiperazin-1-yl)pyridin-2-yl]amino}pyrimidin-4-yl)-2-methylphenyl]ethyl}-1,2,4-oxadiazole-5-carboxamide Example 9D (200 mg, 0.35 mmol), Example 1J (145 mg, 0.42 mmol), N,N-diisopropylethylamine (123 μL, 0.70 mmol) and potassium iodide (291 mg, 1.76 mmol) were mixed in N,N-dimethylformamide (3.5 mL). The mixture was stirred at 80° C. for 4 hours. The mixture was cooled, quenched with a few drops of formic acid, and directly subjected to reverse phase preparative HPLC to isolate the title compound (Phenomenex Gemini® AXA C18 column, 30×250 mm×5 μm, 0.1% formic acid in water and acetonitrile as mobile phases). $^1$H NMR (500 MHz, dimethyl sulfoxide-$d_6$): δ ppm 10.25 (s, 1H), 10.07 (s, 1H), 9.81 (d, J=7.8 Hz, 1H), 8.68 (d, J=1.1 Hz, 1H), 8.04 (d, J=3.0 Hz, 2H), 7.80-7.76 (m, 2H), 7.67 (d, J=8.8 Hz, 1H), 7.54 (d, J=8.7 Hz, 1H), 7.50 (dd, J=8.9, 2.7 Hz, 1H), 7.21 (d, J=8.6 Hz, 2H), 7.17 (d, J=8.5 Hz, 2H), 5.27 (p, J=7.1 Hz, 1H), 3.70 (t, J=6.7 Hz, 2H), 3.01 (s, 2H), 2.70 (t, J=7.6 Hz, 2H), 2.64 (td, J=6.7, 2.6 Hz, 2H), 2.50-2.43 (m, 4H), 2.41 (s, 3H), 2.37-2.27 (m, 2H), 1.45 (d, J=7.0 Hz, 3H), 1.29 (s, 9H), 0.94 (s, 6H). LC/MS (ESI+) m/z 786.9 (M+H)+.

Example 10

3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-3-fluoro-2-methylphenyl}ethyl]-1,2,4-oxadiazole-5-carboxamide Example 10A 1-bromo-2-fluoro-4-iodo-3-methylbenzene A 5 L reactor was changed with 1-bromo-2-fluoro-4-iodobenzene (288 g, 0.96 mol) in anhydrous tetrahydrofuran (2.0 L). The mixture was chilled to −60° C., lithium diisopropylamide (2 M in tetrahydrofuran, 526 mL, 1.05 mol) was added, and the mixture was stirred at −60° C. for 1 hour. Iodomethane (163 g, 1.15 mol) was added, and the mixture was stirred at −60° C. for 12 hours. The reaction mixture was diluted with water (1.0 L) and extracted with methyl tert-butyl ether (1.0 L×3). The same reaction was duplicated three times on the same scale. The combined organic layer of the four batches was washed with brine, dried with sodium sulfate, and filtered. The filtrate was concentrated under reduced pressure to provide crude title compound. $^1$H NMR (400 MHz, CDCl$_3$): δ ppm 7.46 (d, J=8.4 Hz, 1H), 7.10 (t, J=7.6 Hz, 1H), 2.41 (s, 3H) ppm.

Example 10B 4-bromo-3-fluoro-2-methylbenzaldehyde

A 5 L reactor was charged with Example 10A (360 g, 1.14 mol) and anhydrous tetrahydrofuran (1.8 L), and was chilled to −60° C. iPrMgCl (isopropyl magnesium chloride, 2 M in tetrahydrofuran, 572 mL, 1.14 mol) was added and the mixture was stirred at −60° C. for 1 hour. To the mixture was added morpholine-4-carbaldehyde (158 g, 1.37 mol) at −60° C. The mixture was stirred at 0-5° C. for 4 hours. The reaction mixture was diluted with saturated aqueous NH$_4$Cl solution (0.8 L) and extracted with methyl tert-butyl ether (1.7 L×3). The same reaction was duplicated on the same scale two times. The combined organic layer of the three batches was washed with brine, dried with sodium sulfate, and filtered. The filtrate was concentrated under reduced pressure to provide crude title compound. $^1$H NMR (400 MHz, CDCl$_3$): δ ppm 10.18 (s, 1H), 7.54 (d, J=8.4 Hz, 1H), 7.45 (d, J=8.4 Hz, 1H), 2.60 (s, 3H) ppm.

Example 10C (S,E)-N-(4-bromo-3-fluoro-2-methylbenzylidene)-2-methylpropane-2-sulfinamide A 3 L reactor was charged with triisopropyl borate (840 g, 4.47 mol) and crude Example 10B (746 g, 3.44 mol), and (S)-2-methylpropane-2-sulfinamide (542 g, 4.47 mol) at ambient temperature. The mixture was stirred at 70° C. for 12 hours. The mixture was cooled to ambient temperature, diluted with water (3.0 L), extracted with dichloromethane (2.0 L×2), washed with brine, dried with sodium sulfate, and filtered. The filtrate was concentrated under reduced pressure, and the residue was triturated with methyl tert-butyl ether to provide the title compound. $^1$H NMR (400 MHz, CDCl$_3$): δ ppm 8.78 (s, 1H), 7.60 (d, J=8.4 Hz, 1H), 7.49 (t, J=7.6 Hz, 1H), 2.55 (s, 3H), 1.28 (s, 9H) ppm. MS (ESI) m/z 320.0, 322.0 (M+H)$^+$.

Example 10D (S)—N—((R)-1-(4-bromo-3-fluoro-2-methylphenyl) ethyl)-2-methylpropane-2-sulfinamide A 10 L reactor was charged with anhydrous dichloromethane (4.4 L) and Example 10C (220 g, 0.69 mol). The mixture was chilled to 0° C. CH$_3$MgBr (3.0 M in tetrahydrofuran 573 mL, 1.72 mol) was added at 0° C. dropwise. The mixture was then stirred at ambient temperature for 12 hours. The reaction mixture was chilled in an ice bath, and to the mixture was added saturated aqueous NH$_4$Cl solution (2.2 L). The organic phase was separated, and the aqueous phase was extracted with dichloromethane (2.2 L×2). The combined organic layer was washed with brine, dried with sodium sulfate, and filtered. The filtrate was concentrated under reduced pressure, and the residue was triturated in hexane, filtered, and dried under reduced pressure to provide the title compound. $^1$H NMR (400 MHz, dimethyl sulfoxide): δ ppm 7.52 (t, J=8.0 Hz, 1H), 7.19 (d, J=8.8 Hz, 1H), 5.43 (d, J=5.6 Hz, 1H), 4.59 (m, 1H), 2.26 (s, 3H), 1.42 (d, J=6.8 Hz, 3H), 1.09 (s, 9H) ppm. MS (ESI) m/z 336.0, 338.0 (M+H)$^+$.

Example 10E (S)—N—((R)-1-(3-fluoro-2-methyl-4-(4,4,5,5-tetramethyl-1,3,2-dioxaborolan-2-yl)phenyl)ethyl)-2-methylpropane-2-sulfinamide To a solution of Example 10D (10.5 g, 30.0 mmol) in 1,4-dioxane (200 mL) were added bis(pinacolato)diboron (9.13 g, 36.0 mmol) and potassium acetate (5.88 g, 60.0 mmol) at 20° C. The reaction vessel was evacuated and backfilled with nitrogen three times, and then 1,1'-bis(diphenylphosphino)ferrocene-palladium(II)dichloride dichloromethane complex (2.45 g, 3.00 mmol) was added. The reaction vessel was evacuated and backfilled with nitrogen three times again. The reaction mixture was heated to 100° C. and stirred for 16 hours. The reaction mixture was cooled and filtered through a pad of diatomaceous earth. The filtrate was concentrated under reduced pressure, and the residue was purified by column chromatography on silica gel, by eluting with petroleum ether and ethyl acetate to provide the title compound. $^1$H NMR (400 MHz, dimethyl sulfoxide-d$_6$): δ ppm 7.38-7.48 (m, 1H), 7.24 (d, J=7.75 Hz, 1H), 5.35-5.43 (m, 1H), 4.53-4.69 (m, 1H), 2.19 (d, J=2.00 Hz, 3H), 1.42 (d, J=6.63 Hz, 3H), 1.28 (s, 12H), 1.08 (s, 9H) ppm.

Example 10F (R)-1-(3-fluoro-2-methyl-4-(4,4,5,5-tetramethyl-1,3, 2-dioxaborolan-2-yl)phenyl)ethan-1-amine To a solution of Example 10E (20.0 g, 52.2 mmol) in methyl tert-butyl ether (400 mL) was added hydrochloride (4 N in methyl tert-butyl ether, 400 mL) dropwise at ambient temperature. The mixture was stirred for 3 hours, concentrated under reduced pressure, and triturated in methyl tert-butyl ether (50 mL). The solid was isolated by filtration and dried under vacuum to give the crude title compound. $^1$H NMR (400 MHz, dimethyl sulfoxide-d$_6$): δ 8.63 (br s, 3H), 7.56-7.49 (m, 1H), 7.43 (d, J=7.9 Hz, 1H), 4.57 (q, J=6.7 Hz, 1H), 2.22 (d, J=1.8 Hz, 3H), 1.46 (d, J=6.6 Hz, 3H), 1.29 (s, 12H) ppm. MS (ESI) m/z 280.0 (M+H)$^+$.

Example 10G (R)-3-(tert-butyl)-N-(1-(3-fluoro-2-methyl-4-(4,4,5, 5-tetramethyl-1,3,2-dioxaborolan-2-yl)phenyl)ethyl)-1,2,4-oxadiazole-5-carboxamide To a solution of Example 10F (7.00 g, 21.1 mmol) and methyl 3-(tert-butyl)-1,2,4-oxadiazole-5-carboxylate (9.70 g, 52.7 mmol) in ethanol (140 mL) was added triethylamine (23.5 mL, 169 mmol) at 20° C. The mixture was stirred at 60° C. for 12 hours, and then concentrated under reduced pressure to remove ethanol. The crude material was purified by column chromatography on silica gel, eluting with petroleum ether and ethyl acetate to provide the title compound. $^1$H NMR (400 MHz, dimethyl sulfoxide-d$_6$): δ ppm 9.90 (br d, J=7.6 Hz, 1H), 7.47 (t, J=6.9 Hz, 1H), 7.38-7.22 (m, 1H), 5.28 (br t, J=7.2 Hz, 1H), 2.33-2.18 (m, 3H), 1.46 (br d, J=6.9 Hz, 3H), 1.42-1.19 (m, 21H) ppm. MS (ESI) m/z 432.2 (M+H)$^+$.

Example 10H (R)-3-(tert-butyl)-N-(1-(4-(6-chloropyrimidin-4-yl)-3-fluoro-2-methylphenyl)ethyl)-1,2,4-oxadiazole-5-carboxamide To a mixture of Example 10G (2.80 g, 6.49 mmol) and 4,6-dichloropyrimidine (1.93 g, 12.98 mmol) in tetrahydrofuran (120 mL) was added a solution of potassium phosphate (2.76 g, 12.98 mmol) in water (30 mL) at 20° C. The mixture was degassed at ambient temperature using a nitrogen stream, and to the mixture was added [1,1'-bis(diphenylphosphino)ferrocene]dichloro-palladium(II) (265 mg, 0.33 mmol) under N$_2$. The reaction mixture was heated to 80° C. and stirred for 2 hours. The mixture was cooled, poured into water, and extracted with ethyl acetate (three times). The combined organic layer was washed with brine, dried over sodium sulfate, and filtered. The filtrate was concentrated under reduced pressure, and the residue was purified by silica column chromatography, eluting with tetrahydrofuran in petroleum ether to provide crude title compound. $^1$H NMR (400 MHz, dimethyl sulfoxide-d$_6$): δ ppm 9.93 (d, J=7.8 Hz, 1H), 9.07 (s, 1H), 8.30 (s, 1H), 8.09 (d, J=7.8 Hz, 1H), 7.63 (d, J=8.5 Hz, 1H), 5.33 (quin, J=7.2 Hz, 1H), 2.48-2.47 (m, 1H), 2.47 (s, 2H), 1.50 (d, J=7.0 Hz, 3H), 1.36 (s, 9H) ppm. MS (ESI) m/z 418.2 (M+H)$^+$.

Example 10I tert-butyl (S)-4-(6-((6-(4-((R)-1-(3-(tert-butyl)-1,2,4-oxadiazole-5-carboxamido)ethyl)-2-fluoro-3-methylphenyl)pyrimidin-4-yl)amino)pyridin-3-yl)-3-methylpiperazine-1-carboxylate To a solution of Example 10H (500 mg, 1.20 mmol) in 1,4-dioxane (10 mL) were added Example 1L (385 mg, 1.32 mmol), Pd$_2$(dba)$_3$ (CAS 52409-22-0, 55 mg, 0.06 mmol), XantPhos (CAS 161265-03-8, 69 mg, 0.12 mmol) and cesium carbonate (780 mg, 2.39 mmol). The mixture was degassed using nitrogen stream and stirred at 100° C. for 16 hours under nitrogen atmosphere. The reaction mixture was cooled, diluted with ethyl acetate, filtered through diatomaceous earth, concentrated under reduced pressure, and purified by silica chromatography using ethyl acetate and petroleum ether to afford the title compound. LC/MS (ESI+): m/z 674.4 (M+H)$^+$.

Example 10J 3-(tert-butyl)-N—((R)-1-(3-fluoro-2-methyl-4-(6-((5-((S)-2-methylpiperazin-1-yl)pyridin-2-yl)amino)pyrimidin-4-yl)phenyl)ethyl)-1,2,4-oxadiazole-5-carboxamide To a solution of Example 10I (150 mg, 0.223 mmol) in methyl tert-butyl ether (2 mL) was added hydrochloride (4 N in methyl tert-butyl ether, 2 mL) drop-wise. The reaction mixture was stirred at ambient temperature for 2 hours. The reaction mixture was concentrated under reduced pressure to afford the title compound as hydrochloride salt. LC/MS (ESI+): m/z 574.4 (M+H)$^+$.

Example 10K 3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-3-fluoro-2-methylphenyl}ethyl]-1,2,4-oxadiazole-5-carboxamide To a solution of Example 10J (100 mg, 0.17 mmol) in N,N-dimethylformamide (2 mL) were added Example 1J (54 mg, 0.17 mmol), potassium iodide (145 mg, 0.87 mmol) and potassium carbonate (48 mg, 0.35 mmol). The mixture was stirred at 80° C. for 2 hours. The mixture was cooled to ambient temperature, filtered, and directly subjected to reverse phase preparative HPLC to isolate the title compound (Gilson GX-281 system, Phenomenex Gemini® NX C18 column, 30×75 mm×3 μm, 10 mM ammonium bicarbonate in water and acetonitrile as mobile phases). $^1$H NMR (400 MHz, dimethyl sulfoxide-d$_6$): δ ppm 10.33 (s, 1H), 10.08 (s, 1H), 9.93 (br d, J=7.5 Hz, 1H), 8.72 (s, 1H), 7.96 (br d, J=2.4 Hz, 2H), 7.81 (t, J=8.0 Hz, 1H), 7.72 (br d, J=2.0 Hz, 1H), 7.43 (br d, J=8.3 Hz, 2H), 7.32-7.17 (m, 4H), 5.33 (quin, J=6.9 Hz, 1H), 3.92-3.83 (m, 1H), 3.76 (t, J=6.7 Hz, 2H), 3.26-3.16 (m, 1H), 2.98 (br t, J=9.5 Hz, 1H), 2.85 (br d, J=10.6 Hz, 1H), 2.81-2.74 (m, 2H), 2.69 (br t, J=6.7 Hz, 3H), 2.61-2.54 (m, 2H), 2.46-2.42 (m, 1H), 2.35 (d, J=1.8 Hz, 3H), 2.31-2.25 (m, 1H), 1.52 (d, J=7.0 Hz, 3H), 1.36 (s, 9H), 0.98 (d, J=6.3 Hz, 3H) ppm. MS (ESI) m/z 790.3 (M+H)$^+$.

Example 11

3-tert-butyl-N-{(1R)-1-[4-(6-{[5-(4-{2-[4-(2,4-dioxo-1,3-diazinan-1-yl)phenyl]ethyl}piperazin-1-yl)pyridin-2-yl]amino}pyrimidin-4-yl)-3-fluoro-2-methylphenyl]ethyl}-1,2,4-oxadiazole-5-carboxamide Example 11A tert-butyl (R)-4-(6-((6-(4-(1-(3-(tert-butyl)-1,2,4-oxadiazole-5-carboxamido)ethyl)-2-fluoro-3-methylphenyl)pyrimidin-4-yl)amino)pyridin-3-yl)piperazine-1-carboxylate To a solution of Example 10H (2.40 g, 5.46 mmol) in 1,4-dioxane (80 mL) were added Example 3B (1.67 g, 6.00 mmol), Pd$_2$(dba)$_3$ (CAS 52409-22-0, 250 mg, 0.27 mmol), XantPhos (CAS 161265-03-8, 316 mg, 0.32 mmol) and cesium carbonate (3.56 g, 10.91 mmol). The mixture was degassed using nitrogen stream and stirred at 100° C. for 16 hours under nitrogen atmosphere. The reaction mixture was cooled, diluted with ethyl acetate, filtered through diatomaceous earth, concentrated under reduced pressure, and purified by silica chromatography using ethyl acetate and petroleum ether to afford the title compound. $^1$H NMR (400 MHz, dimethyl sulfoxide-d$_6$): δ ppm 10.15 (s, 1H), 9.96 (d, J=7.8 Hz, 1H), 8.75 (s, 1H), 8.08-7.94 (m, 2H), 7.87-7.68 (m, 2H), 7.52-7.40 (m, 2H), 5.41-5.29 (m, 1H), 3.48 (br d, J=4.8 Hz, 4H), 3.14-3.03 (m, 4H), 2.37 (d, J=1.9 Hz, 3H), 1.53 (d, J=7.0 Hz, 3H), 1.43 (s, 9H), 1.38 (s, 9H) ppm. LC/MS (ESI+): m/z 660.4 (M+H)$^+$.

Example 11B (R)-3-(tert-butyl)-N-(1-(3-fluoro-2-methyl-4-(6-((5-(piperazin-1-yl)pyridin-2-yl)amino)pyrimidin-4-yl)phenyl)ethyl)-1,2,4-oxadiazole-5-carboxamide To a solution of Example 11A (3.15 g, 4.30 mmol) in 1,4-dioxane (40 mL) was added hydrochloride (4 N in 1,4-dioxane, 40 mL) drop-wise. The reaction mixture was stirred at ambient temperature for 2 hours. The reaction mixture was concentrated under reduced pressure to afford the title compound as hydrochloride salt. $^1$H NMR (400 MHz, dimethyl sulfoxide-d$_6$): δ ppm 10.11 (s, 1H), 10.06-9.88 (m, 1H), 8.74 (s, 1H), 8.00 (br s, 2H), 7.87-7.64 (m, 2H), 7.45 (br d, J=7.1 Hz, 2H), 5.35 (br t, J=6.9 Hz, 1H), 3.04 (br s, 4H), 2.86 (br s, 4H), 2.37 (br s, 3H), 1.53 (br d, J=6.6 Hz, 3H), 1.37 (s, 9H) ppm. LC/MS (ESI+): m/z 560.3 (M+H)$^+$.

Example 11C 3-tert-butyl-N-{(1R)-1-[4-(6-{[5-(4-{2-[4-(2,4-dioxo-1,3-diazinan-1-yl)phenyl]ethyl}piperazin-1-yl)pyridin-2-yl]amino}pyrimidin-4-yl)-3-fluoro-2-methylphenyl]ethyl}-1,2,4-oxadiazole-5-carboxamide To a solution of Example 11B (130 mg, 0.21 mmol) in N,N-dimethylformamide (1 mL) were added Example 1J (86 mg, 0.25 mmol), sodium bromide (129 mg, 1.25 mmol) and sodium bicarbonate (70 mg, 0.84 mmol). The mixture was stirred at 80° C. for 12 hours. The mixture was cooled to ambient temperature, filtered, and directly subjected to reverse phase preparative HPLC to isolate the title compound (Phenomenex Gemini® NX C18 column, 40×80 mm×3 μm, 10 mM ammonium bicarbonate in water and acetonitrile as mobile phases). $^1$H NMR (400 MHz, dimethyl sulfoxide-d$_6$): δ ppm 10.34 (s, 1H), 10.09 (s, 1H), 9.94 (br d, J=7.63 Hz, 1H), 8.72 (s, 1H), 8.01 (br s, 1H), 7.81 (br t, J=8.07 Hz, 1H), 7.39-7.49 (m, 2H), 7.21-7.30 (m, 3H), 5.33 (br t, J=6.94 Hz, 1H), 3.76 (t, J=6.63 Hz, 2H), 3.14 (br s, 5H), 2.74-2.82 (m, 2H), 2.69 (br t, J=6.69 Hz, 2H), 2.52-2.64 (m, 6H), 2.35 (d, J=1.50 Hz, 3H), 1.51 (br d, J=6.88 Hz, 3H), 1.36 (s, 9H) ppm. MS (ESI) m/z 776.3 (M+H)$^+$.

Example 12

3-tert-butyl-N-{(1R)-1-[4-(6-{[5-(4-{2-[4-(2,4-di-oxo-1,3-diazinan-1-yl)phenyl]ethyl}piperazin-1-yl)pyridin-2-yl]amino}pyrimidin-4-yl)-5-fluoro-2-methylphenyl]ethyl}-1,2,4-oxadiazole-5-carboxamide

Example 12A 4-bromo-5-fluoro-2-methylbenzaldehyde

A 2 L flask was charged with 1-bromo-2-fluoro-4-iodo-5-methylbenzene (25 g, 79 mmol) and anhydrous tetrahydrofuran (400 mL) and chilled to −25° C. iPrMgC$_1$ (isopropyl magnesium chloride, 1.3 M in tetrahydrofuran, 67.2 mL, 87 mmol) were added, and the mixture was stirred at −25° C. for 30 minutes. To the mixture was added anhydrous N,N-dimethylformamide (7.38 mL, 96 mmol) at −25° C. The mixture was allowed to warm up to 0-5° C. and stirred for 1.5 hours. The reaction mixture was quenched with 1 N hydrochloric acid (200 mL) carefully, and the mixture was extracted with ethyl acetate (three times). The combined organic phase was dried over sodium sulfate, filtered, and concentrated under reduced pressure to provide crude title compound. $^1$H NMR (400 MHz, CDCl$_3$): δ ppm 10.21 (d, J=1.7 Hz, 1H), 7.58-7.54 (m, 2H), 2.64 (s, 3H) ppm.

Example 12B (S,E)-N-(4-bromo-5-fluoro-2-methylbenzylidene)-2-methylpropane-2-sulfinamide A 1 L flask was charged with Example 12A (17.00 g, 78.0 mmol) and dichloromethane (340 mL). To this stirred solution were added (S)-2-methylpropane-2-sulfinamide (10.44 g, 86.0 mmol) and titanium (IV) ethoxide (35.7 g, 157 mmol) at ambient temperature. The mixture was stirred for 16 hours, and then quenched at 0° C. with water (36 mL). The mixture was filtered, and the filter cake was washed with dichloromethane (three times using 300 mL). The filtrate was concentrated under reduced pressure, and the crude material was triturated in hexane (50 mL) for 30 minutes. The solid was isolated by filtration, washed with hexane, and dried under high vacuum to afford the title compound.

Example 12C (S)—N—((R)-1-(4-bromo-5-fluoro-2-methylphenyl)ethyl)-2-methylpropane-2-sulfinamide A 2 L flask was charged with anhydrous dichloromethane (400 mL) and Example 12B (21.6 g, 67.5 mmol). The mixture was chilled to 0° C. CH$_3$MgBr (3.0 M in tetrahydrofuran, 56.2 mL, 169 mmol) was added at 0° C. dropwise. The mixture was then stirred at 0° C. for 5 hours. The reaction mixture was quenched with saturated aqueous NH$_4$C$_1$ solution (500 mL). The organic phase was separated, and the aqueous phase was extracted with dichloromethane (100 mL×3). The combined organic layer was washed with brine, dried with sodium sulfate, and filtered. The filtrate was concentrated under reduced pressure, and the residue was purified by silica column chromatography using ethyl acetate and petroleum ether to isolate the title compound. MS (ESI) m/z 335.9, 337.9 (M+H)$^+$.

Example 12D (S)—N—((R)-1-(5-fluoro-2-methyl-4-(4,4,5,5-tetramethyl-1,3,2-dioxaborolan-2-yl)phenyl)ethyl)-2-methylpropane-2-sulfinamide To a solution of Example 12C (15.0 g, 43.3 mmol) in 1,4-dioxane (300 mL) were added bis(pinacolato)diboron (13.19 g, 51.9 mmol) and potassium acetate (8.49 g, 87.0 mmol) at 20° C. The reaction vessel was evacuated and backfilled with nitrogen three times, and then 1,1'-bis(diphenylphosphino)ferrocene-palladium(II)dichloride dichloromethane complex (3.53 g, 4.33 mmol) was added. The reaction vessel was evacuated and backfilled with nitrogen three times again. The reaction mixture was heated to 100° C. and stirred for 16 hours. The reaction mixture was cooled and filtered through a pad of diatomaceous earth. The filtrate was concentrated under reduced pressure, and the residue was purified by column chromatography on silica gel, by eluting with petroleum ether and ethyl acetate to provide the title compound. $^1$H NMR (400 MHz, dimethyl sulfoxide-d$_6$): δ ppm 7.51 (d, J=6.0 Hz, 1H), 7.05 (d, J=10.5 Hz, 1H), 4.80 (br d, J=3.4 Hz, 1H), 3.49 (br d, J=2.6 Hz, 1H), 2.34 (s, 3H), 1.50-1.44 (m, 3H), 1.36 (s, 12H), 1.23-1.19 (m, 9H) ppm.

Example 12E (R)-1-(5-fluoro-2-methyl-4-(4,4,5,5-tetramethyl-1,3,2-dioxaborolan-2-yl)phenyl)ethan-1-amine To a solution of Example 12D (3.00 g, 7.83 mmol) in dichloromethane (10 mL) was added hydrochloride (4 N in 1,4-dioxane, 30 mL) dropwise at ambient temperature. The mixture was stirred for 24 hours and concentrated under reduced pressure to give the crude title compound. MS (ESI) m/z 280.0 (M+H)$^+$.

Example 12F (R)-3-(tert-butyl)-N-(1-(5-fluoro-2-methyl-4-(4,4,5,5-tetramethyl-1,3,2-dioxaborolan-2-yl)phenyl)ethyl)-1,2,4-oxadiazole-5-carboxamide To a solution of Example 12E (3.80 g, 13.61 mmol) and methyl 3-(tert-butyl)-1,2,4-oxadiazole-5-carboxylate (3.76 g, 20.42 mmol) in tetrahydrofuran (60 mL) was added 2,3,4,6,7,8,9,10-octahydropyrimido[1,2-a]azepine (6.16 mL, 40.80 mmol) at ambient temperature. The reaction mixture was stirred at 85° C. for 16 hours, cooled, concentrated under reduced pressure, and purified by column chromatography on silica gel, and eluted with hexane and ethyl acetate to provide the title compound. MS (ESI) m/z 432.2 (M+H)$^+$.

Example 12G (R)-3-(tert-butyl)-N-(1-(4-(6-chloropyrimidin-4-yl)-5-fluoro-2-methylphenyl)ethyl)-1,2,4-oxadiazole-5-carboxamide The title compound was prepared according to the procedure used for Example 10H, substituting Example 12F for Example 10G. MS (ESI) m/z 418.2 (M+H)$^+$.

Example 12H tert-butyl (R)-4-(6-((6-(4-(1-(3-(tert-butyl)-1,2,4-oxadiazole-5-carboxamido)ethyl)-2-fluoro-5-methylphenyl)pyrimidin-4-yl)amino)pyridin-3-yl)piperazine-1-carboxylate A stirred mixture of Example 3B (406 mg, 1.46 mmol), Example 12G (435 mg, 1.04 mmol), racemic BINAP-Pd-G3 (CAS 2151915-22-7, 99 mg, 0.1 mmol) and cesium carbonate (746 mg, 2.29 mmol) in 1,4-dioxane (6.5 mL) was heated at 110° C. for 4 hours under nitrogen atmosphere. The mixture was cooled, filtered, concentrated under reduced pressure, and the residue was purified using silica chromatography with ethyl acetate and hexane to isolate the title compound. LC/MS (ESI+): m/z 660.4 (M+H)$^+$.

Example 12I (R)-3-(tert-butyl)-N-(1-(5-fluoro-2-methyl-4-(6-((5-(piperazin-1-yl)pyridin-2-yl)amino)pyrimidin-4-yl)phenyl)ethyl)-1,2,4-oxadiazole-5-carboxamide The title compound was prepared according to the procedure used for Example 11B, substituting Example 12H for Example 11A. MS (ESI) m/z 560.4 (M+H)$^+$.

Example 12J 3-tert-butyl-N-{(1R)-1-[4-(6-{[5-(4-{2-[4-(2,4-dioxo-1,3-diazinan-1-yl)phenyl]ethyl}piperazin-1-yl)pyridin-2-yl]amino}pyrimidin-4-yl)-5-fluoro-2-methylphenyl]ethyl}-1,2,4-oxadiazole-5-carboxamide To a solution of Example 12I (100 mg, 0.17 mmol) in N,N-dimethylformamide (1.7 mL) were added Example 1J (81 mg, 0.24 mmol), potassium iodide (139 mg, 0.84 mmol) and N,N-diisopropylethylamine (205 μL, 1.17 mmol). The mixture was stirred at 80° C. for 2 hours. The mixture was cooled to ambient temperature, filtered, and directly subjected to reverse phase preparative HPLC to isolate the title compound (Phenomenex Gemini® AXA C18 column, 30×250 mm×5 μm, 0.1% formic acid in water and acetonitrile as mobile phases). $^1$H NMR (500 MHz, dimethyl sulfoxide-d$_6$): δ ppm 10.34 (s, 1H), 10.11 (s, 1H), 9.87 (d, J=7.9 Hz, 1H), 8.73 (s, 1H), 8.04-7.95 (m, 2H) 7.83 (d, J=8.0 Hz, 1H), 7.72 (brs, 1H), 7.50-7.45 (m, 1H), 7.43 (d, J=12.5 Hz, 1H), 7.30-7.20 (m, 4H), 5.29 (p, J=7.2 Hz, 1H), 3.76 (t, J=6.7 Hz, 2H), 3.14 (brs, 4H), 2.81 (brs, 2H), 2.70 (t, J=6.8 Hz, 2H), 2.67-2.55 (m, 3H), 2.42 (s, 3H), 1.51 (d, J=7.0 Hz, 3H), 1.37 (s, 9H) ppm. MS (ESI) m/z 776.8 (M+H)$^+$.

Example 13

3-tert-butyl-N-[(1R)-1-{4-[6-({5-[(2S)-4-{2-[4-(2,4-dioxo-1,3-diazinan-1-yl)phenyl]ethyl}-2-(propan-2-yl)piperazin-1-yl]pyridin-2-yl}amino)pyrimidin-4-yl]-2-methylphenyl}ethyl]-1,2,4-oxadiazole-5-carboxamide

Example 13A tert-butyl (S)-3-isopropyl-4-(6-nitropyridin-3-yl)piperazine-1-carboxylate To a mixture of 5-fluoro-2-nitropyridine (467 mg, 3.28 mmol) in dimethyl sulfoxide (10 mL) were added (S)-tert-butyl 3-isopropylpiperazine-1-carboxylate (500 mg, 2.190 mmol) and N,N-diisopropylethylamine (1.147 mL, 6.57 mmol) under N$_2$ at 20° C. The reaction mixture was stirred at 120° C. for 16 hours. The mixture was cooled and poured into ice water (30 mL). The material in the mixture was collected by filtration. The material was triturated in a mixture of ethyl acetate and petroleum ether to form a slurry. The slurry was filtered, and the filter cake was dried under vacuum to provide the title compound. $^1$H NMR (400 MHz, dimethyl sulfoxide-d$_6$): δ ppm 8.25 (d, J=3.00 Hz, 1H), 8.11 (d, J=9.26 Hz, 1H), 7.46 (dd, J=9.38, 3.00 Hz, 1H), 4.02-4.13 (m, 1H), 3.92 (br d, J=12.26 Hz, 3H), 3.18 (br s, 1H), 2.84-3.10 (m, 2H), 2.01-2.15 (m, 1H), 1.41 (s, 9H), 1.05 (br d, J=4.38 Hz, 3H), 0.73 (d, J=6.75 Hz, 3H) ppm.

Example 13B tert-butyl (S)-4-(6-aminopyridin-3-yl)-3-isopropylpiperazine-1-carboxylate To a mixture of Pd/C (10 wt %, 121 mg, 0.114 mmol) in ethyl acetate (12 mL) was added Example 13A (400 mg, 1.142 mmol) at ambient temperature. The mixture was hydrogenated using a hydrogen balloon for 2 hours. The mixture was filtered through a pad of diatomaceous earth, and the filtrate was concentrated under reduced pressure to provide the crude title compound. $^1$H NMR (400 MHz, dimethyl sulfoxide-d$_6$): δ ppm 7.66 (br s, 1H), 7.21 (br d, J=7.75 Hz, 1H), 6.39 (d, J=8.75 Hz, 1H), 5.49 (br s, 2H), 3.35-3.65 (m, 2H), 2.90 (br s, 3H), 2.51-2.54 (m, 2H), 1.77 (br s, 1H), 1.41 (s, 9H), 0.70-0.91 (m, 6H) ppm.

Example 13C tert-butyl (S)-4-(6-((6-(4-((R)-1-(3-(tert-butyl)-1,2,4-oxadiazole-5-carboxamido)ethyl)-3-methylphenyl)pyrimidin-4-yl)amino)pyridin-3-yl)-3-isopropylpiperazine-1-carboxylate To a solution of Example 1M (200 mg, 0.49 mmol) in 1,4-dioxane (5 mL) were added Example 13B (233 mg, 0.73 mmol), Pd$_2$(dba)$_3$ (CAS 52409-22-0, 44 mg, 0.049 mmol), XantPhos (CAS 161265-03-8, 28 mg, 0.049 mmol) and cesium carbonate (316 mg, 0.97 mmol). The mixture was degassed using nitrogen stream and stirred at 100° C. for 12 hours. The reaction mixture was cooled, diluted with ethyl acetate, and filtered through diatomaceous earth. The filtrate was concentrated under reduced pressure, and the residue was purified by silica chromatography using tetrahydrofuran and petroleum ether to afford the title compound. LC/MS (ESI+): m/z 684.5 (M+H)$^+$.

Example 13D 3-(tert-butyl)-N—((R)-1-(4-(6-((5-((S)-2-isopropylpiperazin-1-yl)pyridin-2-yl)amino)pyrimidin-4-yl)-2-methylphenyl)ethyl)-1,2,4-oxadiazole-5-carboxamide To a solution of Example 13C (280 mg, 0.372 mmol) in 1,4-dioxane (3 mL) was added hydrochloride (4 N in dioxane, 3 mL) dropwise at ambient temperature. The mixture was stirred for 1 hour and concentrated under reduced pressure to afford the crude title compound as hydrochloride salt. $^1$H NMR (400 MHz, dimethyl sulfoxide-d$_6$): δ ppm 9.89 (s, 1H), 8.67 (s, 1H), 7.97 (br d, J=2.64 Hz, 2H), 7.77-7.88 (m, 1H), 7.74-7.89 (m, 1H), 7.55-7.69 (m, 2H), 7.21-7.43 (m, 2H), 5.33 (quin, J=7.12 Hz, 1H), 3.21-3.31 (m, 3H), 3.00-3.11 (m, 1H), 2.83-2.92 (m, 1H), 2.62-2.82 (m, 3H), 2.47 (s, 3H), 1.51 (d, J=6.90 Hz, 3H), 1.36 (s, 9H), 0.89 (d, J=6.53 Hz, 3H), 0.75 (d, J=6.78 Hz, 3H) ppm. LC/MS (ESI+): m/z 584.5 (M+H)$^+$.

Example 13E 3-tert-butyl-N-[(1R)-1-{4-[6-({5-[(2S)-4-{2-[4-(2,4-dioxo-1,3-diazinan-1-yl)phenyl]ethyl}-2-(propan-2-yl)piperazin-1-yl]pyridin-2-yl}amino)pyrimidin-4-yl]-2-methylphenyl}ethyl]-1,2,4-oxadiazole-5-carboxamide To a solution of Example 13D (220 mg, 0.34 mmol) in acetonitrile (5 mL) were added Example 1J (175 mg, 0.51 mmol), sodium iodide (153 mg, 1.02 mmol) and N,N-diisopropylethylamine (296 μL, 1.70 mmol). The mixture was stirred at 80° C. for 16 hours. The mixture was cooled to ambient temperature, filtered, and directly subjected to reverse phase preparative HPLC to isolate the title compound (Waters™ Xbridge C18 column, 30×100 mm×10 μm, 10 mM ammonium bicarbonate in water and acetonitrile as mobile phases). $^1$H NMR (400 MHz, dimethyl sulfoxide-d$_6$): δ ppm 10.35 (s, 1H), 9.86-10.00 (m, 2H), 8.68 (s, 1H), 8.00 (br d, J=2.63 Hz, 2H), 7.82 (br s, 2H), 7.60 (br d, J=8.55 Hz, 2H), 7.36-7.47 (m, 1H), 7.25 (q, J=8.70 Hz, 4H), 5.27-5.39 (m, 1H), 3.69-3.80 (m, 2H), 3.38-3.43 (m, 2H), 3.09-3.20 (m, 1H), 2.88 (br s, 1H), 2.73-2.79 (m, 2H), 2.67-2.71 (m, 2H), 2.52 (d, J=1.75 Hz, 2H), 2.47 (s, 3H), 2.28-2.35 (m, 2H), 2.17-2.26 (m, 2H), 1.51 (d, J=7.02 Hz, 3H), 1.36 (s, 9H), 0.89 (d, J=6.58 Hz, 3H), 0.76 (d, J=6.80 Hz, 3H) ppm. MS (ESI) m/z 800.5 (M+H)$^+$.

Example 14

3-tert-butyl-N-[(1R)-1-{2-chloro-4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]phenyl}ethyl]-1,2,4-oxadiazole-5-carboxamide Example 14A (S,E)-N-(4-bromo-2-chlorobenzylidene)-2-methylpropane-2-sulfinamide A 1 L flask was charged with triisopropyl borate (139 g, 0.74 mol), 4-bromo-2-chlorobenzaldehyde (125 g, 0.57 mol), and (S)-2-methylpropane-2-sulfinamide (90 g, 0.74 mol) at ambient temperature. The mixture was stirred at 70° C. for 12 hours. Water (0.5 L) was added, and the mixture was extracted with dichloromethane (0.5 L×3), washed with brine (1.0 L), dried with sodium sulfate, and filtered. The filtrate was concentrated under reduced pressure. The reaction was duplicated three times on the same scale. The crude material from all four batches were combined to provide the title compound. MS (ESI) m/z 322.0, 324.0 (M+H)$^+$.

Example 14B (S)—N—((R)-1-(4-bromo-2-chlorophenyl)ethyl)-2-methylpropane-2-sulfinamide A 5 L reactor was charged with dichloromethane (3.5 L) and Example 14A (173 g, 0.53 mol). The mixture was chilled at 0° C. CH$_3$MgBr (3.0 M in tetrahydrofuran, 268 mL, 0.80 mol) was added at 0° C. dropwise. The mixture was stirred at ambient temperature for 12 hours. The reaction mixture was chilled in an ice bath, and to the mixture was added saturated aqueous NH$_4$Cl solution (1.6 L). The organic phase was separated, and the aqueous phase was extracted with dichloromethane (0.5 L×3). The reaction was duplicated four times on the same scale. The combined organic layer was washed with brine (5.5 L), dried with sodium sulfate, and filtered. The filtrate was concentrated under reduced pressure, and the residue was triturated in hexane to provide crude title compound. MS (ESI) m/z 338.0, 340.0 (M+H)$^+$.

Example 14C (S)—N—((R)-1-(2-chloro-4-(4,4,5,5-tetramethyl-1,3,2-dioxaborolan-2-yl)phenyl)ethyl)-2-methylpropane-2-sulfinamide To a solution of Example 14B (15.0 g, 40.0 mmol) in 1,4-dioxane (150 mL) were added bis(pinacolato)diboron (10.1 g, 40.0 mmol) and potassium acetate (7.82 g, 80.0 mmol) at 20° C. The reaction vessel was evacuated and backfilled with nitrogen three times, and 1,1'-bis(diphenylphosphino)ferrocene-palladium(II)dichloride dichloromethane complex (3.26 g, 4.0 mmol) was added. The reaction vessel was evacuated and backfilled with nitrogen three times again. The reaction mixture was heated to 110° C. and stirred for 16 hours. The reaction mixture was cooled and filtered through a pad of diatomaceous earth. The filtrate was concentrated under reduced pressure, and the residue was purified by column chromatography on silica gel, by eluting with petroleum ether and ethyl acetate to provide the title compound. MS (ESI) m/z 386.2 (M+H)$^+$.

Example 14D (R)-1-(2-chloro-4-(4,4,5,5-tetramethyl-1,3,2-dioxaborolan-2-yl)phenyl)ethan-1-amine To a solution of Example 14C (8.00 g, 20.7 mmol) in 1,4-dioxane (100 mL) was added hydrochloride (4 N in 1,4-dioxane, 100 mL) dropwise at ambient temperature. The mixture was stirred for 2 hours and concentrated under reduced pressure to give the crude title compound as hydrochloride salt. MS (ESI) m/z 282.3 (M+H)$^+$.

Example 14E (R)-3-(tert-butyl)-N-(1-(2-chloro-4-(4,4,5,5-tetramethyl-1,3,2-dioxaborolan-2-yl)phenyl)ethyl)-1,2,4-oxadiazole-5-carboxamide To a solution of Example 14D (6.60 g, 20.8 mmol) and methyl 3-(tert-butyl)-1,2,4-oxadiazole-5-carboxylate (7.64 g, 41.5 mmol) in ethanol (180 mL) was added triethylamine (17.4 mL, 125 mmol) at 20° C. The mixture was stirred at 80° C. for 12 hours, and then concentrated under reduced pressure to remove ethanol. The crude material was purified by column chromatography on silica gel, eluting with petroleum ether and ethyl acetate to provide the title compound. $^1$H NMR (400 MHz, dimethyl sulfoxide-d$_6$): δ ppm 9.95 (d, J=7.5 Hz, 1H), 7.65-7.56 (m, 3H), 5.42 (quin, J=7.2 Hz, 1H), 1.48 (d, J=7.1 Hz, 3H), 1.36 (s, 9H), 1.28 (s, 12H) ppm. MS (ESI) m/z 434.4 (M+H)$^+$.

Example 14F (R)-3-(tert-butyl)-N-(1-(4-(6-chloropyrimidin-4-yl)-2-chlorophenyl)ethyl)-1,2,4-oxadiazole-5-carboxamide To a mixture of Example 14E (6.00 g, 13.83 mmol) and 4,6-dichloropyrimidine (2.47 g, 16.60 mmol) in 1,4-dioxane (111 mL) and water (28 mL) were added [1,1'-bis(diphenylphosphino)ferrocene]dichloro-palladium(II) (1.13 g, 1.38 mmol) and potassium phosphate (5.87 g, 27.7 mmol). The mixture was degassed at ambient temperature using a nitrogen stream and stirred at 80° C. for 1 hour under nitrogen atmosphere. The mixture was cooled, poured into water, and extracted with ethyl acetate (three times). The combined organic layer was washed with brine, dried over sodium sulfate, and filtered. The filtrate was concentrated under reduced pressure, and the residue was purified by silica column chromatography, eluting with ethyl acetate in hexane to provide crude title compound. $^1$H NMR (400 MHz, dimethyl sulfoxide-$d_6$): δ ppm 10.02 (br d, J=7.63 Hz, 1H), 9.11 (d, J=0.63 Hz, 1H), 8.39 (d, J=0.75 Hz, 1H), 8.31 (d, J=1.63 Hz, 1H), 8.23 (dd, J=8.25, 1.63 Hz, 1H), 7.74 (d, J=8.25 Hz, 1H), 5.47 (br t, J=7.19 Hz, 1H), 1.53 (d, J=7.00 Hz, 3H), 1.37 (s, 9H) ppm. MS (ESI) m/z 420.1, 422.1 (M+H)$^+$.

Example 14G tert-butyl (S)-4-(6-((6-(4-((R)-1-(3-(tert-butyl)-1,2,4-oxadiazole-5-carboxamido)ethyl)-3-chlorophenyl)pyrimidin-4-yl)amino)pyridin-3-yl)-3-methylpiperazine-1-carboxylate To a solution of Example 14H (288 mg, 0.69 mmol) in 1,4-dioxane (6.4 mL) were added Example 1L (240 mg, 0.82 mmol), Pd$_2$(dba)$_3$ (CAS 52409-22-0, 38 mg, 0.04 mmol), XantPhos (CAS 161265-03-8, 40 mg, 0.07 mmol) and cesium carbonate (447 mg, 1.37 mmol). The mixture was degassed using nitrogen stream and stirred at 100° C. for 16 hours under nitrogen atmosphere. The reaction mixture was cooled, diluted with ethyl acetate, filtered through diatomaceous earth, concentrated under reduced pressure, and purified by silica chromatography using ethyl acetate and petroleum ether to afford the title compound. $^1$H NMR (400 MHz, dimethyl sulfoxide-$d_6$): δ ppm 9.97-10.11 (m, 2H), 7.92-8.11 (m, 4H), 7.72 (br d, J=8.11 Hz, 2H), 7.44 (dd, J=9.12, 2.80 Hz, 1H), 5.46 (m, 1H), 3.75-3.89 (m, 2H), 3.61 (br d, J=11.09 Hz, 1H), 3.17 (br d, J=11.80 Hz, 3H), 2.90-3.00 (m, 1H), 1.53 (d, J=7.03 Hz, 3H), 1.41 (s, 9H), 1.37 (s, 9H), 0.88 (d, J=6.32 Hz, 3H) ppm. LC/MS (ESI+): m/z 676.4 (M+H)$^+$.

Example 14H 3-(tert-butyl)-N—((R)-1-(2-chloro-4-(6-((5-((S)-2-methylpiperazin-1-yl)pyridin-2-yl)amino)pyrimidin-4-yl)phenyl)ethyl)-1,2,4-oxadiazole-5-carboxamide To a solution of Example 14G (258 mg, 0.38 mmol) in 1,4-dioxane (3 mL) was added hydrochloride (4 N in 1,4-dioxane, 3 mL) drop-wise. The reaction mixture was stirred at ambient temperature for 1 hour. The reaction mixture was concentrated under reduced pressure, dissolved in water (10 mL), and basified with saturated sodium bicarbonate aqueous solution to adjust pH to 8. The mixture was extracted with dichloromethane (10 mL, three times), and the combined organic phase was washed with brine (10 mL), dried over sodium sulfate and filtered. The filtrate was concentrated under reduced pressure to afford the title compound. $^1$H NMR (400 MHz, dimethyl sulfoxide-$d_6$): δ ppm 10.08 (br s, 2H), 8.72 (s, 1H), 7.91-8.10 (m, 4H), 7.71 (br d, J=8.13 Hz, 2H), 7.40 (br dd, J=9.13, 2.75 Hz, 2H), 5.46 (br s, 1H), 3.64-3.80 (m, 1H), 3.01-3.15 (m, 1H), 2.79-2.98 (m, 3H), 2.62-2.77 (m, 2H), 1.53 (br d, J=6.88 Hz, 3H), 1.36 (s, 9H), 0.95 (d, J=6.38 Hz, 3H) ppm. LC/MS (ESI+): m/z 576.3 (M+H)$^+$.

Example 14I 3-tert-butyl-N-[(1R)-1-{2-chloro-4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]phenyl}ethyl]-1,2,4-oxadiazole-5-carboxamide To a solution of Example 14H (85 mg, 0.15 mmol) in acetonitrile (2 mL) were added Example 1J (102 mg, 0.30 mmol), sodium iodide (66 mg, 0.44 mmol) and N,N-diisopropylethylamine (129 μL, 0.74 mmol). The mixture was stirred at 80° C. for 16 hours. The mixture was cooled to ambient temperature, filtered, and directly subjected to reverse phase preparative HPLC to isolate the title compound (Phenomenex Luna® C18 column, 30×75 mm×3 μm, 0.1% formic acid in water and acetonitrile as mobile phases). $^1$H NMR (400 MHz, dimethyl sulfoxide-$d_6$): δ ppm 10.34 (s, 1H), 9.97-10.13 (m, 2H), 8.73 (s, 1H), 7.91-8.11 (m, 4H), 7.72 (br d, J=8.13 Hz, 2H), 7.47 (br d, J=8.00 Hz, 1H), 7.20-7.33 (m, 4H), 5.46 (quin, J=7.10 Hz, 1H), 3.80-3.95 (m, 1H), 3.76 (t, J=6.63 Hz, 2H), 3.16-3.26 (m, 2H), 2.95-3.10 (m, 2H), 2.57-2.93 (m, 8H), 1.53 (d, J=7.00 Hz, 3H), 1.37 (s, 9H), 1.00 (br d, J=6.00 Hz, 3H) ppm. MS (ESI) m/z 792.2 (M+H)$^+$.

Example 15

3-tert-butyl-N-[(1R)-1-{4-[6-({5-[(2R)-4-{2-[4-(2,4-dioxo-1,3-diazinan-1-yl)phenyl]ethyl}-2-(methoxymethyl)piperazin-1-yl]pyridin-2-yl}amino)pyrimidin-4-yl]-2-methylphenyl}ethyl]-1,2,4-oxadiazole-5-carboxamide

Example 15A (R)-1-benzyl 4-tert-butyl 2-(hydroxymethyl)piperazine-1,4-dicarboxylate To a solution of (R)-tert-butyl 3-(hydroxymethyl)piperazine-1-carboxylate (1.5 g, 6.94 mmol) in tetrahydrofuran (30 mL) was added a solution of sodium carbonate (2.205 g, 20.81 mmol) in water (6.00 mL) at 20° C. Benzyl chloroformate (1.775 g, 10.40 mmol) was added dropwise at 0° C. The reaction mixture was extracted with ethyl acetate (three times), washed with brine, dried over sodium sulfate, and filtered. The filtrate was concentrated under reduced pressure, and the residue was purified by column chromatography on silica gel using ethyl acetate in petroleum ether to provide the title compound. $^1$H NMR (400 MHz, dimethyl sulfoxide-$d_6$): δ ppm 7.28-7.39 (m, 5H), 5.09 (s, 2H), 4.82 (br t, J=4.63 Hz, 1H), 3.97 (br d, J=13.63 Hz, 1H), 3.80 (br d, J=12.76 Hz, 2H), 3.34-3.49 (m, 2H), 2.68-3.07 (m, 4H), 1.99 (s, 1H), 1.40 (s, 9H), 1.17 (t, J=7.07 Hz, 1H) ppm. MS (ESI) m/z 295.2 (M−tBu+H)$^+$.

Example 15B (R)-1-benzyl 4-tert-butyl 2-(methoxymethyl)piperazine-1,4-dicarboxylate Example 15A (2.0 g, 5.71 mmol) was dissolved in dichloromethane (40 mL), and the mixture was chilled to 0° C. To the mixture were added 1,8-bis(dimethylamino)naphthalene (4.89 g, 22.83 mmol) in one portion and then trimethyloxonium tetrafluoroborate (3.38 g, 22.83 mmol) was added slowly over 5 minutes. The mixture was stirred for 30 minutes at 0° C., allowed to warm to 20° C., and stirred for 1 hour. The reaction mixture was extracted with ethyl acetate (five times). The combined organic layer was washed with brine, dried over sodium sulfate, and filtered. The filtrate was concentrated under reduced pressure, and the residue was purified by silica column chromatography using ethyl acetate in petroleum ether to provide the title compound. $^1$H NMR (400 MHz, dimethyl sulfoxide-$d_6$): δ ppm 7.27-7.40 (m, 4H), 5.01-5.17 (m, 2H), 4.18 (br d, J=0.88 Hz, 1H), 3.68-3.97 (m, 3H), 3.32 (d, J=2.26 Hz, 2H), 3.24 (br s, 3H), 2.68-3.04 (m, 3H), 1.40 (s, 9H) ppm.

Example 15C tert-butyl (R)-3-(methoxymethyl)piperazine-1-carboxylate

To a suspension of Pd/C (10 wt %, 0.38 g, 0.357 mmol) in ethyl acetate (26 mL) was added Example 15B (1.3 g, 3.57 mmol). The reaction mixture was hydrogenated using a hydrogen balloon at ambient temperature for 16 hours. The mixture was filtered through a pad of diatomaceous earth, and the filtrate was concentrated under reduced pressure to provide the crude title compound. $^1$H NMR (400 MHz, dimethyl sulfoxide-$d_6$): δ ppm 3.65-3.87 (m, 2H), 3.26 (s, 3H), 3.20-3.22 (m, 1H), 3.22 (d, J=6.02 Hz, 1H), 2.83 (br d, J=11.80 Hz, 1H), 2.59-2.77 (m, 2H), 2.46-2.56 (m, 2H), 2.30 (br s, 1H), 1.40 (s, 9H) ppm.

Example 15D (R)-tert-butyl 3-(methoxymethyl)-4-(6-nitropyridin-3-yl)piperazine-1-carboxylate To a mixture of 5-fluoro-2-nitropyridine (740 mg, 5.21 mmol) in dimethyl sulfoxide (16 mL) were added Example 15C (800 mg, 3.47 mmol) and N,N-diisopropylethylamine (1.820 mL, 10.42 mmol) at ambient temperature. The reaction mixture was heated to 120° C. and stirred for 12 hours. The reaction mixture was cooled and poured into water, and the mixture was extracted with ethyl acetate (twice). The combined organic layer was washed with brine, dried over sodium sulfate, and filtered. The filtrate was concentrated under reduced pressure, and the residue was purified by silica column chromatography using ethyl acetate in petroleum ether to provide the title compound. $^1$H NMR (400 MHz, dimethyl sulfoxide-$d_6$): δ ppm 8.64 (d, J=2.88 Hz, 1H), 8.44 (d, J=8.88 Hz, 1H), 8.22 (d, J=3.00 Hz, 1H), 8.16 (d, J=9.26 Hz, 1H), 8.04 (dd, J=8.94, 2.81 Hz, 1H), 7.44 (dd, J=9.26, 3.00 Hz, 1H), 4.34 (br s, 1H), 3.96-4.07 (m, 1H), 3.90 (br d, J=1.63 Hz, 1H), 3.80 (br d, J=12.88 Hz, 1H), 3.36-3.48 (m, 2H), 3.32 (s, 1H), 3.23 (s, 5H), 1.42 (s, 9H) ppm. MS (ESI) m/z 353.3 (M+H)$^+$.

Example 15E (R)-tert-butyl 4-(6-aminopyridin-3-yl)-3-(methoxymethyl)piperazine-1-carboxylate To a suspension of Pd/C (10 wt %, 362 mg, 0.341 mmol) in ethyl acetate (36 mL) was added Example 15D (1.2 g, 3.41 mmol). The reaction mixture was hydrogenated using a hydrogen balloon at ambient temperature for 16 hours. The reaction mixture was filtered through a pad of diatomaceous earth, and the filtrate was concentrated under reduced pressure to provide the crude title compound. $^1$H NMR (400 MHz, dimethyl sulfoxide-$d_6$): δ ppm 7.62 (d, J=2.63 Hz, 1H), 7.21 (dd, J=8.76, 2.50 Hz, 1H), 6.40 (d, J=8.76 Hz, 1H), 5.51 (br s, 2H), 3.39-3.69 (m, 3H), 3.01-3.18 (m, 5H), 2.72-2.94 (m, 2H), 1.41 (s, 9H) ppm.

Example 15F tert-butyl (R)-4-(6-((6-(4-((R)-1-(3-(tert-butyl)-1,2,4-oxadiazole-5-carboxamido)ethyl)-3-methylphenyl)pyrimidin-4-yl)amino)pyridin-3-yl)-3-(methoxymethyl)piperazine-1-carboxylate To a solution of Example 1E (300 mg, 0.75 mmol) in 1,4-dioxane (5 mL) were added Example 15E (363 mg, 1.13 mmol), Pd$_2$(dba)$_3$ (CAS 52409-22-0, 69 mg, 0.075 mmol), XantPhos (CAS 161265-03-8, 43 mg, 0.075 mmol) and cesium carbonate (489 mg, 1.50 mmol). The mixture was degassed using argon stream and stirred at 100° C. for 12 hours. The reaction mixture was cooled, diluted with ethyl acetate, filtered through diatomaceous earth, concentrated under reduced pressure, and purified by silica chromatography using ethyl acetate and petroleum ether to afford the title compound. $^1$H NMR (400 MHz, dimethyl sulfoxide-$d_6$): δ ppm 10.02 (s, 1H), 9.91 (d, J=7.89 Hz, 1H), 8.70 (s, 1H), 8.02 (br d, J=2.85 Hz, 1H), 7.79-7.87 (m, 2H), 7.65-7.74 (m, 1H), 7.60 (d, J=8.55 Hz, 1H), 7.46 (dd, J=9.21, 2.63 Hz, 1H), 7.25-7.35 (m, 1H), 5.24-5.39 (m, 1H), 3.69-4.00 (m, 3H), 3.24-3.33 (m, 2H), 3.20 (br s, 5H), 2.89-3.10 (m, 2H), 2.47 (s, 3H), 1.51 (d, J=6.80 Hz, 3H), 1.42 (s, 9H), 1.36 (s, 9H) ppm. LC/MS (ESI+): m/z 686.5 (M+H)$^+$.

Example 15G 3-(tert-butyl)-N—((R)-1-(4-(6-((5-((R)-2-(methoxymethyl)piperazin-1-yl)pyridin-2-yl)amino)pyrimidin-4-yl)-2-methylphenyl)ethyl)-1,2,4-oxadiazole-5-carboxamide To a solution of Example 15F (450 mg, 0.66 mmol) in 1,4-dioxane (3 mL) was added hydrochloride (4N in dioxane, 3 mL) dropwise at ambient temperature. The mixture was stirred for 1 hour and concentrated under reduced to afford the crude title compound as hydrochloride salt. $^1$H NMR (400 MHz, dimethyl sulfoxide-$d_6$): δ ppm 9.97 (s, 1H), 9.91 (br d, J=8.11 Hz, 1H), 8.69 (s, 1H), 7.95-8.00 (m, 1H), 7.80-7.86 (m, 2H), 7.55-7.70 (m, 2H), 7.38-7.43 (m, 1H), 7.27-7.34 (m, 1H), 5.27-5.38 (m, 1H), 3.67-3.81 (m, 2H), 3.56 (s, 6H), 3.51-3.61 (m, 1H), 3.34 (s, 3H), 3.14-3.20 (m, 1H), 3.12-3.20 (m, 1H), 2.92-3.05 (m, 1H), 2.90-3.03 (m, 1H), 2.78-2.86 (m, 1H), 2.65-2.74 (m, 1H), 2.47 (s, 3H), 1.51 (br d, J=6.80 Hz, 3H), 1.33-1.39 (m, 9H) ppm. LC/MS (ESI+): m/z 586.4 (M+H)$^+$.

Example 15H 3-tert-butyl-N-[(1R)-1-{4-[6-({5-[(2R)-4-{2-[4-(2,4-dioxo-1,3-diazinan-1-yl)phenyl]ethyl}-2-(methoxymethyl)piperazin-1-yl]pyridin-2-yl}amino)pyrimidin-4-yl]-2-methylphenyl}ethyl]-1,2,4-oxadiazole-5-carboxamide Example 15G (130 mg, 0.22 mmol), Example 1J (115 mg, 0.33 mmol), N,N-diisopropylethylamine (194 µL, 1.11 mmol) and sodium iodide (100 mg, 0.66 mmol) were mixed in acetonitrile (5 mL). The mixture was stirred at 80° C. for 16 hours. The mixture was cooled, quenched with a few drops of formic acid, and directly subjected to reverse phase preparative HPLC to isolate the title compound (Phenomenex Luna® C18 column, 30×75 mm×3 µm, 0.1% formic acid in water and acetonitrile as mobile phases). $^1$H NMR (400 MHz, dimethyl sulfoxide-$d_6$): δ ppm 10.33 (s, 1H), 9.96 (s, 1H), 9.88 (br d, J=7.65 Hz, 1H), 8.70 (s, 1H), 8.14 (s, 1H), 8.00 (br d, J=2.38 Hz, 2H), 7.76-7.91 (m, 2H), 7.64-7.73 (m, 1H), 7.60 (br d, J=8.66 Hz, 1H), 7.44 (br dd, J=8.91, 2.64 Hz, 1H), 7.18-7.31 (m, 4H), 5.33 (quin, J=7.09 Hz, 1H), 3.85-3.96 (m, 1H), 3.76 (t, J=6.65 Hz, 2H), 3.51-3.68 (m, 1H), 3.29 (br s, 1H), 3.17 (s, 3H), 2.85-3.08 (m, 3H), 2.73-2.82 (m, 2H), 2.69 (br t, J=6.65 Hz, 2H), 2.51-2.63 (m, 3H), 2.47 (s, 3H), 2.17-2.34 (m, 2H), 1.51 (br d, J=6.90 Hz, 3H), 1.36 (s, 9H) ppm. MS (ESI) m/z 802.3 (M+H)$^+$.

Example 16

3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-(trifluoromethyl)phenyl}ethyl]-1,2,4-oxadiazole-5-carboxamide

Example 16A (S,E)-N-(4-bromo-2-(trifluoromethyl)benzylidene)-2-methylpropane-2-sulfinamide A 500 mL flask was charged with 4-bromo-2-(trifluoromethyl)benzaldehyde (10.00 g, 39.5 mmol) and dichloromethane (100 mL). To the stirred mixture were added (S)-2-methylpropane-2-sulfinamide (6.23 g, 51.4 mmol) and then titanium (IV) ethoxide (18.03 g, 79.0 mmol) at ambient temperature. The mixture was stirred at 30° C. for 12 hours and quenched with ethyl acetate (50 mL) and water (50 mL). The mixture was filtered, and the organic phase was separated. The aqueous phase was extracted with ethyl acetate (100 mL, three times), and the combined organic phase was dried over sodium sulfate and filtered. The filtrate was concentrated under reduced pressure to afford the crude title compound. $^1$H NMR (400 MHz, CDCl$_3$): δ ppm 8.89 (d, J=1.5 Hz, 1H), 8.09 (d, J=8.4 Hz, 1H), 7.91 (d, J=1.3 Hz, 1H), 7.79 (d, J=8.4 Hz, 1H), 1.31-1.21 (m, 9H) ppm.

Example 16B (S)—N—((R)-1-(4-bromo-2-(trifluoromethyl)phenyl)ethyl)-2-methylpropane-2-sulfinamide A 250 mL flask was charged with anhydrous toluene (60 mL) and Example 16A (5.40 g, 15.16 mmol). The mixture was chilled to −5° C. CH$_3$MgBr (3.0 M in tetrahydrofuran, 10.1 mL, 30.3 mmol) was added dropwise. The mixture was then stirred at 0° C. for 3 hours, and saturated aqueous NH$_4$Cl solution (120 mL) was added to quench the reaction. The organic phase was separated, and the aqueous phase was extracted with ethyl acetate (30 mL, three times). The combined organic layer was washed with brine (30 mL), dried over sodium sulfate, and filtered. The filtrate was concentrated under reduced pressure, and the residue was purified by silica column chromatography using ethyl acetate and petroleum ether to afford the title compound. $^1$H NMR (400 MHz, dimethyl sulfoxide): δ ppm 7.92 (dd, J=8.50, 1.75 Hz, 1H), 7.81 (d, J=1.88 Hz, 1H), 7.74 (d, J=8.50 Hz, 1H), 5.63 (d, J=4.50 Hz, 1H), 4.69 (quin, J=5.78 Hz, 1H), 1.44 (d, J=6.63 Hz, 3H), 1.06 (s, 9H) ppm. MS (ESI) m/z 372.0, 374.0 (M+H)$^+$.

Example 16C (S)—N—((R)-1-(2-trifluoromethyl-4-(4,4,5,5-tetramethyl-1,3,2-dioxaborolan-2-yl)phenyl)ethyl)-2-methylpropane-2-sulfinamide To a solution of Example 16B (1.00 g, 2.69 mmol) in 1,4-dioxane (20 mL) were added bis(pinacolato)diboron (853 mg, 3.36 mmol) and potassium acetate (527 mg, 5.37 mmol) at 20° C. The reaction vessel was evacuated and backfilled with nitrogen three times, and then 1,1'-bis(diphenylphosphino)ferrocene-palladium(II)dichloride dichloromethane complex (197 mg, 0.27 mmol) was added. The reaction vessel was evacuated and backfilled with nitrogen three times again. The reaction mixture was heated to 80° C. and stirred for 16 hours. The reaction mixture was cooled and filtered through a pad of diatomaceous earth. The filtrate was concentrated under reduced pressure, and the residue was purified by column chromatography on silica gel, by eluting with petroleum ether and ethyl acetate to provide the title compound. $^1$H NMR (400 MHz, dimethyl sulfoxide-$d_6$): δ ppm 7.93 (br d, J=6.58 Hz, 1H), 7.71-7.89 (m, 2H), 5.62 (br d, J=3.73 Hz, 1H), 4.66-4.82 (m, 1H), 1.45 (br d, J=6.14 Hz, 3H), 1.30 (s, 9H), 1.06 (br d, J=2.19 Hz, 12H) ppm. MS (ESI) m/z 420.2 (M+H)$^+$.

Example 16D (R)-1-(2-trifluoromethyl-4-(4,4,5,5-tetramethyl-1,3,2-dioxaborolan-2-yl)phenyl)ethan-1-amine To a solution of Example 16C (900 mg, 2.15 mmol) in 1,4-dioxane (5 mL) was added hydrochloride (4 N in 1,4-dioxane, 10 mL) dropwise at ambient temperature. The mixture was stirred for 1 hour and then concentrated under reduced pressure to give the crude title compound as hydrochloride salt. $^1$H NMR (400 MHz, dimethyl sulfoxide-$d_6$): 8.94 (br s, 3H), 8.01-8.15 (m, 2H), 7.93 (s, 1H), 4.52 (br d, J=4.75 Hz, 1H), 1.54 (d, J=6.63 Hz, 3H), 1.31 (s, 12H) ppm. MS (ESI) m/z 316.2 (M+H)$^+$.

Example 16E (R)-3-(tert-butyl)-N-(1-(2-trifluoromethyl-4-(4,4,5,5-tetramethyl-1,3,2-dioxaborolan-2-yl)phenyl)ethyl)-1,2,4-oxadiazole-5-carboxamide To a solution of Example 16D (360 mg, 1.02 mmol) and methyl 3-(tert-butyl)-1,2,4-oxadiazole-5-carboxylate (471 mg, 2.56 mmol) in ethanol (8 mL) was added triethylamine (622 mg, 6.14 mmol) at 20° C. The mixture was stirred at 60° C. for 16 hours, and then concentrated under reduced pressure to remove ethanol. The crude material was purified by column chromatography on silica gel, eluting with petroleum ether and ethyl acetate to provide the title compound. $^1$H NMR (400 MHz, dimethyl sulfoxide-d$_6$): δ ppm 10.04 (d, J=7.23 Hz, 1H), 7.93-8.00 (m, 1H), 7.84-7.92 (m, 2H), 5.40 (quin, J=6.91 Hz, 1H), 1.49 (d, J=6.80 Hz, 3H), 1.36 (s, 9H), 1.30 (s, 12H) ppm. MS (ESI) m/z 468.2 (M+H)$^+$.

Example 16F (R)-3-(tert-butyl)-N-(1-(4-(6-chloropyrimidin-4-yl)-2-(trifluoromethyl)phenyl)ethyl)-1,2,4-oxadiazole-5-carboxamide To a mixture of Example 16E (230 mg, 0.49 mmol) and 4,6-dichloropyrimidine (147 mg, 0.98 mmol) in tetrahydrofuran (10 mL) was added a solution of potassium phosphate (209 mg, 0.98 mmol) in water (2.5 mL) and [1,1'-bis(diphenylphosphino)ferrocene]dichloro-palladium(II) (22 mg, 0.03 mmol). The mixture was degassed at ambient temperature using a nitrogen stream and stirred at 80° C. for 2 hours under nitrogen atmosphere. The mixture was cooled, poured into water, and extracted with ethyl acetate (three times). The combined organic layer was washed with brine, dried over sodium sulfate, and filtered. The filtrate was concentrated under reduced pressure, and the residue was purified by silica column chromatography, eluting with ethyl acetate in hexane to provide crude title compound. $^1$H NMR (400 MHz, dimethyl sulfoxide-d$_6$): δ ppm 10.10 (br d, J=7.23 Hz, 1H), 9.14 (s, 1H), 8.52-8.59 (m, 2H), 8.49 (s, 1H), 8.06 (d, J=8.11 Hz, 1H), 5.45 (br t, J=6.91 Hz, 1H), 1.55 (d, J=6.80 Hz, 3H), 1.37 (d, J=1.32 Hz, 9H) ppm. MS (ESI) m/z 454.1 (M+H)$^+$.

Example 16G tert-butyl (S)-4-(6-((6-(4-((R)-1-(3-(tert-butyl)-1,2,4-oxadiazole-5-carboxamido)ethyl)-3-(trifluoromethyl)phenyl)pyrimidin-4-yl)amino)pyridin-3-yl)-3-methylpiperazine-1-carboxylate To a solution of Example 16F (170 mg, 0.38 mmol) in 1,4-dioxane (4 mL) were added Example 1L (138 mg, 0.45 mmol), Pd$_2$(dba)$_3$ (CAS 52409-22-0, 21 mg, 0.022 mmol), XantPhos (CAS 161265-03-8, 22 mg, 0.037 mmol) and cesium carbonate (244 mg, 0.75 mmol). The mixture was degassed using nitrogen stream and stirred at 100° C. for 16 hours under nitrogen atmosphere. The reaction mixture was cooled, diluted with ethyl acetate, and filtered through diatomaceous earth. The filtrate was concentrated under reduced pressure, and the residue was purified by silica chromatography using ethyl acetate and petroleum ether to afford the title compound. $^1$H NMR (400 MHz, dimethyl sulfoxide-d$_6$): δ ppm 10.24 (br s, 1H), 10.10 (d, J=7.23 Hz, 1H), 8.78 (s, 1H), 8.34 (s, 1H), 8.29 (br d, J=8.33 Hz, 1H), 7.99-8.07 (m, 2H), 7.67-7.78 (m, 1H), 7.49 (br dd, J=8.99, 2.41 Hz, 1H), 7.25-7.35 (m, 1H), 5.45 (br t, J=7.13 Hz, 1H), 3.77-3.92 (m, 2H), 3.56-3.69 (m, 1H), 3.26-3.37 (m, 1H), 3.19 (br d, J=11.18 Hz, 2H), 2.91-3.01 (m, 1H), 1.56 (br d, J=6.80 Hz, 3H), 1.42 (s, 9H), 1.37 (s, 9H), 0.89 (d, J=6.58 Hz, 3H) ppm. LC/MS (ESI+): m/z 710.4 (M+H)$^+$.

Example 16H 3-(tert-butyl)-N—((R)-1-(2-trifluoromethyl-4-(6-((5-((S)-2-methylpiperazin-1-yl)pyridin-2-yl)amino)pyrimidin-4-yl)phenyl)ethyl)-1,2,4-oxadiazole-5-carboxamide To a solution of Example 16G (100 mg, 0.14 mmol) in methanol (20 mL) was added hydrochloride (4 N in methanol, 20 mL) drop-wise. The reaction mixture was stirred at ambient temperature for 2 hours. The reaction mixture was concentrated under reduced pressure to afford the crude title compound as hydrochloride salt. $^1$H NMR (400 MHz, dimethyl sulfoxide-d$_6$): δ ppm 9.99-10.17 (m, 2H), 8.75 (s, 1H), 8.35 (s, 1H), 8.28 (br d, J=8.25 Hz, 1H), 7.93-8.18 (m, 3H), 7.65-7.78 (m, 1H), 7.41 (dd, J=9.13, 2.75 Hz, 1H), 7.22-7.35 (m, 1H), 5.45 (quin, J=6.69 Hz, 1H), 3.68-3.78 (m, 1H), 3.18-3.35 (m, 1H), 3.01-3.12 (m, 1H), 2.81-2.98 (m, 3H), 2.66-2.77 (m, 2H), 1.55 (br d, J=6.88 Hz, 3H), 1.37 (s, 9H), 0.96 (d, J=6.38 Hz, 3H) ppm. LC/MS (ESI+): m/z 610.3 (M+H)$^+$.

Example 16I 3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-(trifluoromethyl)phenyl}ethyl]-1,2,4-oxadiazole-5-carboxamide To a solution of Example 16H (63 mg, 0.11 mmol) in acetonitrile (2 mL) were added Example 1J (56 mg, 0.16 mmol), sodium iodide (65 mg, 0.43 mmol) and N,N-diisopropylethylamine (56 μL, 0.32 mmol). The mixture was stirred at 80° C. for 16 hours. The mixture was cooled to ambient temperature, filtered, and directly subjected to reverse phase preparative HPLC to isolate the title compound (Waters™ Xbridge C18 column, 30×100 mm×10 μm, 10 mM ammonium bicarbonate in water and acetonitrile as mobile phases). $^1$H NMR (400 MHz, dimethyl sulfoxide-d$_6$): δ ppm 10.34 (br s, 1H), 10.10 (s, 2H), 8.75 (s, 1H), 8.35 (s, 1H), 8.28 (br d, J=8.25 Hz, 1H), 8.10 (br s, 1H), 8.02 (br d, J=10.38 Hz, 2H), 7.72 (br s, 1H), 7.39-7.54 (m, 1H), 7.17-7.33 (m, 4H), 5.45 (br d, J=5.88 Hz, 1H), 3.88 (br d, J=5.13 Hz, 1H), 3.76 (br t, J=6.57 Hz, 2H), 3.22 (br d, J=11.88 Hz, 1H), 2.99 (br t, J=9.38 Hz, 1H), 2.86 (br d, J=10.76 Hz, 1H), 2.78 (br t, J=7.32 Hz, 2H), 2.66-2.73 (m, 4H), 2.44 (br d, J=11.63 Hz, 2H), 2.31 (br d, J=11.63 Hz, 1H), 1.56 (br d, J=6.75 Hz, 3H), 1.37 (s, 9H), 0.99 (br d, J=6.25 Hz, 3H) ppm. MS (ESI) m/z 826.4 (M+H)$^+$.

Example 17

3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-fluorophenyl}ethyl]-1,2,4-oxadiazole-5-carboxamide Example 17A (S,E)-N-(4-bromo-2-fluorobenzylidene)-2-methylpropane-2-sulfinamide A 1 L reactor was charged with triisopropyl borate (243 g, 1.29 mol), 4-bromo-2-fluorobenzaldehyde (250 g, 1.23 mol), and (S)-2-methylpropane-2-sulfinamide (179 g, 1.48 mol) at ambient temperature. The mixture was stirred at 70° C. for 12 hours. To the reaction mixture was added water (500 mL), and the mixture was extracted with dichloromethane (500 mL×3). The combined organic phase was washed with brine (1.0 L), dried with sodium sulfate, and filtered. The filtrate was concentrated under reduced pressure to provide the title compound. $^1$H NMR (400 MHz, CDCl$_3$): δ ppm 8.82 (s, 1H), 7.81-8.92 (m, 1H), 7.30-7.47 (m, 2H), 1.26 (s, 9H) ppm.

Example 17B (S)—N—((R)-1-(4-bromo-2-fluorophenyl)ethyl)-2-methylpropane-2-sulfinamide A 5 L reactor was charged with anhydrous dichloromethane (3.0 L) and Example 16A (150 g, 0.49 mol). The mixture was chilled to 0° C. CH$_3$MgBr (3.0 M in tetrahydrofuran, 245 mL, 0.73 mol) was added dropwise. The mixture was allowed to warm up to the ambient temperature and stirred for 12 hours, and then saturated aqueous NH$_4$Cl solution (1.0 L) was added to quench the reaction. The organic phase was separated, and the aqueous phase was extracted with dichloromethane (1.0 L, three times). The combined organic layer was washed with brine (2.0 L), dried over sodium sulfate, and filtered. The filtrate was concentrated under reduced pressure to afford the crude title compound. $^1$H NMR (400 MHz, CDCl$_3$): δ ppm 7.21-7.28 (m, 3H), 4.73-4.90 (m, 1H), 3.33 (d, J=4.03 Hz, 1H), 1.56 (d, J=6.85 Hz, 3H), 1.20 (s, 9H) ppm.

Example 17C (R)-1-(4-bromo-2-fluorophenyl)ethan-1-amine

A 1 L reactor was charged with Example 17B (87.0 g, 0.27 mol) and methanol (870 mL). To the stirred solution at 0° C. was added hydrochloride (4 N in methanol, 435 mL, 1.74 mol). The reaction mixture was stirred at 0° C. for 2 hours and concentrated under reduced pressure to dryness to afford the crude title compound as hydrochloride salt. $^1$H NMR (400 MHz, dimethyl sulfoxide-d$_6$): δ ppm 8.80 (s, 3H), 7.59-7.76 (m, 2H), 7.53 (dd, J=8.38, 1.41 Hz, 1H), 4.41-4.63 (m, 1H), 1.44-1.57 (m, 3H) ppm.

Example 17D tert-butyl (R)-(1-(4-bromo-2-fluorophenyl)ethyl)carbamate

A 3 L reactor was charged with Example 17C (65.0 g, 0.30 mol), tetrahydrofuran (650 mL) and water (650 mL). To the stirred solution at 0° C., were added sodium hydroxide (35.8 g, 0.89 mol) and di-tert-butyl decarbonate (78.1 g, 0.36 mol). The reaction was allowed to warm up to the ambient temperature and was stirred for 2 hours. The mixture was diluted with water (1.0 L), and the mixture was extracted with ethyl acetate (1.0 L, three times). The combined organic layer was washed with brine (2.0 L), dried over sodium sulfate, and filtered. The filtrate was concentrated under reduced pressure, and the residue was purified by silica column chromatography with ethyl acetate and petroleum to afford the title compound. $^1$H NMR (400 MHz, CD$_3$OD): δ ppm 7.18-7.39 (m, 3H), 4.88-4.95 (m, 1H), 1.28-1.49 (m, 12H) ppm.

Example 17E tert-butyl (R)-(1-(2-fluoro-4-(4,4,5,5-tetramethyl-1,3,2-dioxaborolan-2-yl)phenyl)ethyl)carbamate To a solution of Example 17D (76.0 g, 0.24 mol) in 1,4-dioxane (760 mL) were added bis(pinacolato)diboron (72.8 g, 0.29 mol) and potassium acetate (46.9 g, 0.48 mol) at 20° C. The reaction vessel was evacuated and backfilled with nitrogen three times, and then 1,1'-bis(diphenylphosphino)ferrocene-palladium(II)dichloride dichloromethane complex (17.5 g, 0.02 mol) was added. The reaction vessel was evacuated and backfilled with nitrogen three times again. The reaction mixture was heated to 100° C. and stirred for 16 hours under a nitrogen atmosphere. The reaction mixture was cooled and filtered through a pad of diatomaceous earth. The filtrate was concentrated under reduced pressure, and the residue was purified by column chromatography on silica gel, by eluting with petroleum ether and ethyl acetate to provide the title compound. $^1$H NMR (400 MHz, CDCl$_3$): δ ppm 7.54 (d, J=7.50 Hz, 1H), 7.45 (d, J=11.03 Hz, 1H), 7.28-7.32 (m, 1H), 4.99 (s, 2H), 1.42 (s, 12H), 1.34 (s, 12H) ppm.

Example 17F (R)-1-(2-fluoro-4-(4,4,5,5-tetramethyl-1,3,2-dioxaborolan-2-yl)phenyl)ethan-1-amine To a solution of Example 17E (1030 mg, 2.15 mmol) in dichloromethane (20 mL) was added hydrochloride (4 N in 1,4-dioxane, 14 mL) dropwise at ambient temperature. The mixture was stirred for 3 hours and was concentrated under reduced pressure to give the crude title compound as hydrochloride salt. $^1$H NMR (400 MHz, dimethyl sulfoxide-d$_6$): 8.68 (br s, 3H), 7.64-7.72 (m, 1H), 7.56 (d, J=7.58 Hz, 1H), 7.40 (d, J=10.64, 1H), 4.62 (br s, 1H), 1.52 (d, J=6.85 Hz, 3H), 1.31 (s, 12H) ppm. MS (ESI) m/z 249.2 (M+H)$^+$.

Example 17G (R)-3-(tert-butyl)-N-(1-(2-fluoro-4-(4,4,5,5-tetramethyl-1,3,2-dioxaborolan-2-yl)phenyl)ethyl)-1,2,4-oxadiazole-5-carboxamide To a solution of Example 17F (850 mg, 2.82 mmol) and methyl 3-(tert-butyl)-1,2,4-oxadiazole-5-carboxylate (779 mg, 4.23 mmol) in 2-methyltetrahydrofuran (10 mL) was added 1,8-diazabicyclo[5.4.0]undec-7-ene (DBU, 1.28 mL, 8.46 mmol) at ambient temperature. The mixture was stirred for 2 hours, and then diluted with ethyl acetate (50 mL) and brine (20 mL). The organic phase was separated, and the aqueous phase was extracted with ethyl acetate (20 mL). The combined organic phase was dried over sodium sulfate and filtered. The filtrate was concentrated under reduced pressure, and the residue was purified by column chromatography on silica gel, eluting with hexane and ethyl acetate to provide the title compound. $^1$H NMR (400 MHz, dimethyl sulfoxide-d$_6$): 9.95 (d, J=7.70 Hz, 1H), 7.49-7.63 (m, 2H), 7.39 (d, J=10.64 Hz, 1H), 5.42 (t, J=7.27 Hz, 1H), 1.56 (d, J=6.97 Hz, 3H), 1.42 (s, 9H), 1.35 (s, 12H) ppm. MS (ESI) m/z 418.2 (M+H)$^+$.

Example 17H (R)-3-(tert-butyl)-N-(1-(4-(6-chloropyrimidin-4-yl)-2-fluorophenyl)ethyl)-1,2,4-oxadiazole-5-carboxamide To a mixture of Example 17G (762 mg, 1.83 mmol) and 4,6-dichloropyrimidine (326 mg, 2.19 mmol) in 1,4-dioxane (7.3 mL) were added a solution of potassium phosphate (775 mg, 3.65 mmol) in water (2 mL) and [1,1'-bis(diphenylphosphino)ferrocene]dichloro-palladium(II) (149 mg, 0.18 mmol). The mixture was degassed at ambient temperature using a nitrogen stream and stirred at 85° C. for 20 minutes under nitrogen atmosphere. The mixture was cooled, poured into water, and extracted with ethyl acetate (three times).

The combined organic layer was washed with brine, dried over sodium sulfate, and filtered. The filtrate was concentrated under reduced pressure, and the residue was purified by silica column chromatography, eluting with ethyl acetate in hexane to provide crude title compound. MS (ESI) m/z 404.1 (M+H)$^+$.

Example 17I tert-butyl (S)-4-(6-((6-(4-((R)-1-(3-(tert-butyl)-1,2,4-oxadiazole-5-carboxamido)ethyl)-3-fluorophenyl)pyrimidin-4-yl)amino)pyridin-3-yl)-3-methylpiperazine-1-carboxylate To a solution of Example 17G (268 mg, 0.66 mmol) in 1,4-dioxane (10 mL) were added Example 1L (349 mg, 1.20 mmol), racemic BINAP-Pd-G3 (CAS 2151915-22-7, 66 mg, 0.066 mmol) and cesium carbonate (649 mg, 1.99 mmol). The mixture was heated at 75° C. for 40 minutes under nitrogen atmosphere. The mixture was cooled, filtered, and the filtrate was concentrated under reduced pressure. The residue was purified using silica chromatography with ethyl acetate and hexane to isolate the title compound. LC/MS (ESI+): m/z 660.4 (M+H)$^+$.

Example 17J 3-(tert-butyl)-N—((R)-1-(2-fluoro-4-(6-((5-((S)-2-methylpiperazin-1-yl)pyridin-2-yl)amino)pyrimidin-4-yl)phenyl)ethyl)-1,2,4-oxadiazole-5-carboxamide To a solution of Example 17J (346 mg, 0.52 mmol) in dichloromethane (10 mL) was added hydrochloride (4 N in 1,4-dioxane, 6.6 mL). The reaction mixture was stirred at ambient temperature for 2 hours. The reaction mixture was concentrated under reduced pressure and purified by silica column chromatography using dichloromethane and methanol (added with 7 N ammonia in methanol) to afford the title compound. LC/MS (ESI+): m/z 560.3 (M+H)$^+$.

Example 17K 3-tert-butyl-N-[(1R)-1-{4-[6-({5-[(2S)-4-{2-[4-(2,4-dioxo-1,3-diazinan-1-yl)phenyl]ethyl}-2-methylpiperazin-1-yl]pyridin-2-yl}amino)pyrimidin-4-yl]-2-fluorophenyl}ethyl]-1,2,4-oxadiazole-5-carboxamide To a solution of Example 17J (80 mg, 0.14 mmol) in N,N-dimethylformamide (1 mL) were added Example 1J (56 mg, 0.16 mmol), potassium iodide (119 mg, 0.72 mmol) and N,N-diisopropylethylamine (50 µL, 0.29 mmol). The mixture was stirred at 80° C. for 2 hours. It was cooled to ambient temperature, filtered, and the filtrate was directly subjected to reverse phase preparative HPLC to isolate the title compound (Phenomenex Gemini® NX C18 column, 30×250 mm×5 µm, 0.1% ammonium hydroxide in water and acetonitrile as mobile phases). $^1$H NMR (500 MHz, dimethyl sulfoxide-d$_6$): δ ppm 10.30 (s, 1H), 9.98 (s, 1H), 9.86 (d, J=7.8 Hz, 1H), 8.66 (s, 1H), 8.00 (s, 1H), 7.94 (d, J=2.9 Hz, 1H), 7.78 (dd, J=8.1, 1.7 Hz, 1H), 7.71 (dd, J=11.5, 1.7 Hz, 1H), 7.66-7.57 (m, 2H), 7.37 (dd, J=9.3, 2.9 Hz, 1H), 7.21 (d, J=8.4 Hz, 2H), 7.17 (d, J=8.4 Hz, 2H), 5.34 (p, J=7.2 Hz, 1H), 3.80 (s, 1H), 3.69 (t, J=6.7 Hz, 2H), 3.15 (d, J=11.3 Hz, 1H), 2.93 (dd, J=10.6 Hz, 1H), 2.79 (d, J=10.4 Hz, 1H), 2.71 (dd, J=7.7, 7.7 Hz, 2H), 2.66-2.59 (m, 2H), 2.55-2.42 (m, 2H), 2.38 (d, J=10.9 Hz, 1H), 2.31-2.20 (m, 2H), 1.49 (d, J=7.0 Hz, 3H), 1.30 (s, 9H), 0.93 (d, J=6.3 Hz, 3H) ppm. MS (ESI) m/z 776.4 (M+H)$^+$.

General

BTK Screening

Btk kinase activity was measured in vitro using an electrophoretic mobility shift assay (MSA). The ability of Btk to phosphorylate a fluorescent peptide substrate (FAM-GEEP-LYWSFPAKKK-NH$_2$) was measured. The kinase reactions were assembled in a total volume of 25 µL per well in 384 well plates. The following was added to each well: compound buffer (or control); enzyme buffer; and substrate buffer, as further described below.

Specifically the following was added: (1) compound buffer or control: 5 µL of 5× compound buffer [(5× compound buffer comprised of: 1× Master Buffer, X µM test compound in 5% dimethyl sulfoxide; (2× Master Buffer comprised of 200 mM HEPES, pH 7.5, 0.2% BSA, and 0.02% Triton X-100)]; and (2) enzyme buffer: 10 µL of 2.5× enzyme buffer (1× Master Buffer, 12.5 mM MgCl$_2$, 2.5 mM DTT, 25 µM sodium orthovanadate, 25 µM beta-glycerophosphate, and 1.25 nM BTK enzyme). Human BTK enzyme Nanosyn-293HEK, wild-type, available from Nanosyn, Santa Clara, CA). Enzyme and compound were pre-incubated for 15 minutes. Additionally, the following was added: (3) substrate buffer: 10 µL of 2.5× substrate buffer (1× Master Buffer, 50 µM ATP, and 2.5 µM of the peptide substrate FAM). Each plate was incubated at 25° C. for 3 hours. The reaction was terminated by adding to each well: 45 µL of 1.55× stop buffer (1× Master Buffer and 31 mM EDTA). The final reaction mixture was as follows: 100 mM HEPES, pH 7.5; 0.1% BSA; 0.01% Triton X-100; 1 mM DTT; 5 mM MgCl$_2$; 10 µM sodium orthovanadate; 10 µM beta-glycerophosphate; 50 µM ATP; 1% dimethyl sulfoxide (from compound); 1 µM fluorescent peptide substrate and 0.5 nM BTK-enzyme.

The terminated reactions were analyzed using a 12 channel LABCHIP® 3000 microfluidic detection instrument (available from Caliper Life Sciences, Waltham, MA). The enzymatic phosphorylation of the peptide resulted in a change in net charge, which enabled electrophoretic separation of product from substrate peptide. As substrate and product peptides were separated, two peaks of fluorescence were observed. Change in the relative fluorescence intensity of the substrate and product peaks was the parameter measured, reflecting enzyme activity. In the presence of an active compound, the ratio between product and substrate was altered. The signal of the product decreased, while the signal of the substrate increased. Capillary electrophoregrams (RDA acquisition files) were analyzed using HTS Well Analyzer software (available from Caliper Life Sciences, Waltham, MA).

Activity in each sample was determined as the product to sum ratio (PSR): P/(S+P), where P was the peak height of the product peptide and S was the peak height of the substrate peptide. For each compound, enzyme activity was measured at various concentrations (12 concentrations of compound spaced by 3× dilution intervals). Negative control samples (0% inhibition in the absence of an active compound) and positive control samples (100% inhibition, in the presence of 20 mM EDTA) were assembled in replicates of four and were used to calculate % inhibition values for each active compound at each concentration. Percent inhibition (Pinh) was determined using following equation: Pinh= (PSR0%−PSRinh)/(PSR0%−PSR100%)*100, where PSRinh was the product sum ratio in the presence of inhibitor, PSR0% was the average product sum ratio in the absence of active compound and PSR100% was the average product sum ratio in 100%-inhibition control samples.

The $IC_{50}$ values of active compounds were determined by 4 parameter sigmoidal dose response model fitting of the inhibition curves (Pinh versus inhibitor concentration) using XLfit® 4 software (IDBS, Boston, MA). The $IC_{50}$ values are reported in Table 2 in the BTK $IC_{50}$ (nM) column.

Cereblon Binding Assay

Cereblon binding was measured in vitro using an AlphaLISA® Human Cereblon Binding Kit (PerkinElmer, Waltham, MA) according to the manufacturer's protocol ("Alpha" refers to Amplified Luminescent Proximity Homogeneous Assay). In this assay, donor beads and acceptor beads come into proximity through ligand binding to CRBN protein. Excitation of the donor beads provokes the release of singlet oxygen that triggers a cascade of energy transfer reactions to the acceptor beads, resulting in a sharp peak in light emission at 615 nm.

Specifically, nickel chelate acceptor beads (PerkinElmer AL108M) were used to capture a 6×HIS-tagged CRBN protein, and streptavidin-coated donor beads (PerkinElmer 6760002) were used to capture 50 nM biotinylated ligand. Each well included the following: sample or control; HIS-tagged CRBN protein; biotinylated ligand; nickel chelate acceptor beads; and streptavidin donor beads.

Competition Assay: Test compounds in 100% dimethyl sulfoxide were plated onto white, low volume 384 well plates (PerkinElmer Proxiplate 384 plus #6008289) using an Labcyte Echo acoustic dispenser, in an 11-point dose curve and 3-fold dilution scheme. This resulted in 10 μM top dose (starting concentration) and 0.1% DMSO final concentrations after the addition of 10 μL of an assay mixture containing His-tagged Cereblon/DDB1 complex and 50 μM biotin-labeled ligand in a buffer (buffer: 10 mM HEPES pH 7.4, 150 mM NaCl, 0.05% Tween-20 and 10 mM DTT). Plates were incubated for 30 minutes at room temperature.

Detection: 10 μL detection reagents were added in low light conditions containing nickel chelate acceptor beads and streptavidin donor beads (Perkin Elmer 6760002), resulting in a final concentration 20 ng/ml. Plates were incubated 1 hour and read on a PerkinElmer™ Envision™ plate reader (680 nm excitation and 570 nM emission settings). The $IC_{50}$ of each compound was determined by calculating percent inhibition from no drug and no protein controls, and the $K_i$ of each compound was calculated using the Cheng-Prusoff transformation. From the $K_i$, the $IC_{50}$ values were determined. The $IC_{50}$ values are reported in Table 2 in the CRBN $IC_{50}$ (nM) column.

Bik Protein in Human Whole Blood MSD ELISA Based Assay

Btk protein degradation was tested using an Meso Scale Discovery-ELISA system (MSD-ELISA): (1) Test compounds were added to human whole blood; (2) human whole blood cells treated with test compounds were lysed; (3) lysed cells were treated with capture antibody, an antibody to Btk; (4) lysed cells were treated with anti-mouse primary antibody to Btk; and (5) lysed cells were treated with anti-mouse antibody (tagged).

Specifically, about 80 μl of fresh human whole blood from healthy donors was transferred into each well of a 96-well V-bottom plate (Costar, Cat No. 3894). Using a TECAN™ D300e Digital Dispenser (Tecan)), 1:4 serially diluted compounds [(8 pt assay) in DMSO solution (final 0.2%) starting at 3 μM top concentration], were added in duplicate. Thereafter, plates were placed in a 37° C. incubator and incubated for 6 hours.

At the end of incubation, 80 μl of 2×CST lysis buffer (Cell Signaling Technology, Cat No. 9803), prepared from a 10× stock solution, was added per well to lyse the blood. Plates were then sealed with a plate sealer and the samples were frozen overnight at −80° C.

Total amount of BTK protein remaining in the blood samples after compound treatment was measured using MSD-ELISA. After thawing the frozen plates, blood lysates were mixed thoroughly and transferred to small spot high-bind MSD plates (Meso Scale Discovery, Cat No. L45XB-3) and coated with capturing antibody, rabbit anti-human BTK (D3H5) (Cell Signaling Technology, Cat No. 8547CF). Thereafter, primary detection antibody, mouse anti-human BTK monoclonal antibody, (BD Biosciences, Cat No. 611117) and secondary detection antibody, anti-mouse SULFO-TAG (Meso Scale Discovery, Cat No. R32AC-1) were added. The assay plates were read on an MSD S600 plate reader by the addition of 2×MSD read buffer (Meso Scale Discovery, R92TC-1). All reagent transfers, including blood lysis, was conducted using a Biomed i7 liquid handler. From the dose response curves, $DC_{50}$ values were calculated by averaging data from duplicate experiments. and Curve fitting was done by non-linear regression using GraphPad Prism. The $DC_{50}$ values are reported in Table 2 in the hWB BTK $DC_{50}$ (nM) column The $D_{max}$ values represent the maximum amount of BTK degradation observed upon compound treatment compared to DMSO only treated samples. The dMax (%) values are reported in Table 2 in the hWB BTK dMax (%) column.

Mouse Bone Marrow Assay

Female $C_{57}BL/6J$ mice (Jackson Laboratories) were used for this study. Compounds or vehicle/control were prepped with EtOH; PEG-400; Phosal 53 MCT (10:30:60, v/v). Four mice were tested per compound or vehicle/control. On Day 1, mice were administered a single dose of Dose A. On Day 2 (after 24 hours), tissue (bone marrow) was collected from one hind leg per mouse.

An MSD (Meso Scale Discovery) ELISA (enzyme-linked immunosorbent assay) based assay was used to determine BTK degradation in mouse bone marrow. The following materials and equipment were used: 10% NP40 solution (nonionic polyoxyethylene surfactant, ThermoFisher, cat no. 28324); protease inhibitor mini tablet (Roche, cat no. 05 892 970 001); PhosphoSTOP™ tablet (Roche, cat no. 04 906 837 001); Pierce™ BCA Protein Assay Kit (Thermofisher, Cat No. 23225); Precellys® 2 mL lysing tube with 2.8 mm beads (VWR, cat no. 10032-756); Bertin Precellys® 24/Cryolys® cooling system; 96-well MSD streptavidin pre-coated plates (MSD, cat no. L15SA-1); MSD Blocker A (MSD, cat no. R93BA-4); capture antibody, biotinylated BTK mAb (BD Biosciences, cat no. 624008; custom order); primary detection antibody, BTK RpAb (rabbit polyclonal antibody, CST, cat no. 8547S, D3H5 clone); secondary detection antibody, anti-Rabbit-Sulfo-Tag (MSD, cat no. R32AB-1); read Buffer, 4× (MSD, cat no. R92TC-1); recombinant BTK protein (Thermofisher, cat no. PR5442A); MSD Tris Wash Buffer (10×) (MSD, cat no. R61TX-1); PBS (phosphate-buffered saline); deionized water (diH$_2$O); Lysis Buffer [0.2% NP40 in PBS+Protease Inhibitor tablet (1 tablet/10 mL)+PhosphoSTOP tablet (1 tablet/10 mL)]; 3% MSD Blocker A [MSD Blocker A+450 mL diH$_2$O+50 mL]; and 10×MSD Tris Wash Buffer.

Procedure

Sample Processing for PD Assay

Mice Bone Marrow Lysates Preparation

Lysis buffer [(PBS+0.2% NP40+PI (protease inhibitor)+ PhosphoSTOP)] was prepared and put on ice until it was fully cold. Ice cold lysis buffer (30011.1) was added to each Precellys® tube containing beads and bone marrow sample. Sample tubes were transferred into Precellys® machine and homogenized using 5000 rpm—2×20 seconds. The sample lysates were centrifuged at 14,000 rpm for 20 minutes at 4° C. after homogenizing.

Protein Estimation (BCA)

The protein concentration was determined using Pierce™ BCA Protein Assay Kit following manufacturer's recommended protocol. The protein normalized working solution was prepared, using 30 µg protein per sample lysate for assay.

Standard Curve Sample Preparation

A 300 ng/ml working stock solution of recombinant BTK protein in lysis buffer was prepared, and the sample was serially diluted at 3-fold dilution (10-point assay, highest concentration was 300 ng/mL and lowest concentration was 0.015 ng/mL)

Performing MSD Assay

Day 1

MSD plate coating: Coating antibody (biotinylated-BTK mAb) stock solution was prepared at 1 µg/mL in PBS buffer. 50 µL/well capture antibody (Biotinylated BTK mAb) solution was added, and the plates were shaken gently at ambient temperature for two hours. The plates were washed 3 times with 1×MSD Tris Wash Buffer in a plate washer (300 µL/well), and the plates were blocked with 3% MSD Blocker A (150 µL/well). The plates were incubated for an additional 1-2 hours at ambient temperature with gentle shaking. The plates were washed 3 times with 1×MSD wash buffer using plate washer. Bone marrow lysates (30 µg) at a final volume of 50 µL/well were added into the plates. The serially diluted standard samples were added to the same plates at a final volume of 50 µL/well. The plates were incubated overnight at 4° C. with gentle shaking.

Day 2

The plates were washed three times with 1×MSD wash buffer (prepared from 10× concentration buffer) using plate washer. Primary detection antibody at 50 µL/well was added (BTK RpAb; 1:1000 dilution in 1% MSD Blocker A). The plates were incubated for two hours at ambient temperature with gentle shaking. The plates were washed three times with 1×MSD wash buffer using plate washer. Anti-Rabbit-SULFO-TAG secondary antibodies (50 µl/well) were added, 1:500 diluted in 1% MSD Blocker A, and the plates were incubated for one to two hours at ambient temperature. The plates were washed three times with 1×MSD tris wash buffer using plate wash. MSD read buffer (150 µL) (1×) was added and the plates were read with MSD machine. Standard curves were generated, and the absolute BTK amounts were used to calculate % remaining BTK in vehicle versus treated samples. The % remaining Btk in the samples is reported in Table 2.

Assay results for Examples 1-19 are shown in Table 2 in the "Mouse Bone Marrow (%) Column"

TABLE 2

| Example | hWB BTK $DC_{50}$ (nM) | hWB BTK dMax (%) | BTK $IC_{50}$ (nM) | CRBN $IC_{50}$ (nM) | Mouse Bone Marrow (%) |
|---|---|---|---|---|---|
| 1 | 4.08 | 99.99 | 0.0977 | 1260 | 11 |
| 2 | 5.93 | 98.84 | 0.128 | 749 | 12 |
| 3 | 2.88 | 99.24 | 0.0339 | 9570 | 22 |
| 4 | 7.62 | 99.78 | 0.141 | ≥10000 | 13 |
| 5 | 6.00 | 99.26 | 0.113 | 648 | 12 |
| 6 | 2.45 | 99.79 | 0.0403 | 378 | 19 |
| 7 | 18.7 | 99.34 | 0.0979 | 609 | 22 |
| 8 | 4.04 | 98.56 | 0.0804 | 3380 | 30 |
| 9 | 9.61 | 99.51 | 0.0988 | 658 | 31 |
| 10 | 3.04 | 98.5 | 0.106 | 6310 | 9 |
| 11 | 4.31 | 97.67 | 0.0973 | 2150 | 29 |
| 12 | 2.27 | 99.82 | 0.0363 | 2010 | 17 |
| 13 | 17.3 | 98.98 | 0.14 | ≥10000 | 26 |
| 14 | 7.91 | 99.73 | 0.053 | 2330 | 16 |
| 15 | 4.21 | 99.91 | 0.0986 | ≥10000 | Nd |
| 16 | 14.22 | 100.29 | 0.438 | ≥10000 | Nd |
| 17 | 4.13 | 99.56 | 0.103 | 3870 | Nd |
| 18 | 15.6 | 99.5 | 0.496 | 1250 | 25 |
| 19 | 3 | 100 | 0.1 | ≥10000 | 51 |

Nd = not determined

Compound 1 (Example 1) Controls Circulating Leukemia Burden of a TCL1-driven CLL Bearing $BTK^{C481S}$ Mutation in C57BL/6 Mice Tumor Cell Generation EIA-TCL1 CLL transgenic mice (Crogen Pharmaceuticals LLC) were crossed with $BTK^{C481S}$ knock-in mice (AbbVie) to generate Eµ-TCL1 transgenic mice carrying the $BTK^{C481S}$ mutation. The leukemic splenocytes from these $BTK^{C481S}$ Eµ-TCL1 transgenic mice (Passage 1) were transplanted intravenously into $C_{57}BL/6$ mice, leading to CLL development in the peripheral blood and spleen. When circulating CLL burden (CD5+CD19+ cells as described below) in the recipient mice reached over 90%, their splenocytes (Passage 2) containing high CLL burden were cryopreserved and used for CLL efficacy studies.

Animal Husbandry

The mouse tumor efficacy study was conducted in compliance with AbbVie's Institutional Animal Care and Use Committee and the National Institutes of Health Guide for Care and Use of Laboratory Animals guidelines in the vivarium at South San Francisco, California. C57BL/6 mice were obtained from Jackson Laboratories and group-housed at 5 per cage under a 14-hour light:10-hour dark schedule.

Tumor Implantation and Animal Treatment

The Passage 2 Eµ-TCL1 $BTK^{C481S}$ splenocytes containing high CLL burden were thawed, washed, and filtered through a 70-µM strainer in cold Hanks' Balanced Salt Solution (HBSS). $10 \times 10^6$ splenocytes cells in 0.2 mL HBSS were injected intravenously per mouse into the tail vein of female 8-10-week-old $C_{57}BL/6$ mice to develop CLL.

To determine the absolute/total leukocyte numbers, complete blood counts were determined for each mouse using the Genesis™ veterinary hematology analyzer (Oxford Science Inc.).

Flow Cytometry

Cells isolated from murine peripheral blood mononuclear cells (PMBCs) were collected to determine antigen expression. The PMBCs were stained with antibodies specific for murine CD5, CD19, and CD45 (cells expressing CD5+CD19+ are frequently present in murine B cell leukemias and are considered CLL cells). Cells were gated on CD45+, and thereafter the percentage of cells that were CD5+CD19+ from that subset was calculated. Flow cytometry was carried out on an BD LSRFortessa™ X-20 Cell Analyzer (BD Biosciences).

Whole blood was collected weekly post tumor implantation via submandibular cheek bleeding. Circulating leukemic burden was calculated by multiplying absolute/total leukocyte count with the percentage of the leukocytes have the immunophenotype CD19⁺CD5⁺.

Beginning 9 days post-inoculation, mice were weighed, bled, and randomized into five groups of N=10 with mean circulating CD19⁺CD5⁺ CLL cell counts of 1,525/μL. Compound 1 (Example 1) was formulated at different concentrations in the vehicle containing 10% ethanol, 30% PEG-400 and 60% Phosal-50 MCT. The vehicle contained 10% ethanol, 30% PEG-400, and 60% Phosal-50 MCT.

Two days after CLL count randomization, mice were treated with the following once daily (QD) for 19 days: Group 1: vehicle; Group 2: Compound 1 Dosage 1; Group 3: Compound 1 Dosage 2; Group 4: Compound 1 Dosage 3; Group 5: Compound 1 Dosage 4.

As shown in FIG. 1, Compound 1 (Example 1) controlled circulating leukemia burden of the TCL1-driven CLL bearing BTK$^{C481S}$ mutation in C57BL/6 mice in a dose-dependent manner. The y-axis shows number of CLL cells (CD19+CD5+) per μL mouse PMBC. Complete CLL burden control (i.e., no increase from the initial tumor burden) was achieved by Compound 1 at Dosage 3 and Dosage 4.

All publications and patents mentioned herein are hereby incorporated by reference in their entirety as if each individual publication or patent was specifically and individually indicated to be incorporated by reference.

It is understood that the foregoing detailed description and accompanying examples are merely illustrative and are not to be taken as limitations upon the scope of the present disclosure, which is defined by the appended claims and their equivalents.

What is claimed is:

1. A compound which is

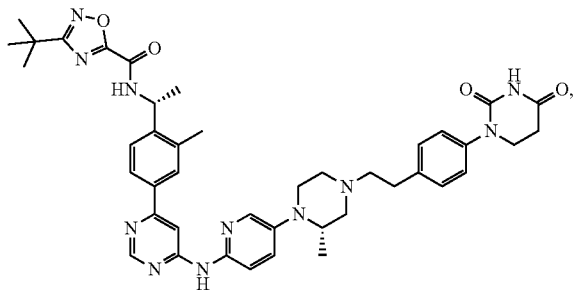 [SMILES: Cc1cc(-c2cc(Nc3ccc(N4CCN(CCc5ccc(N6CCC(=O)NC6=O)cc5)C[C@@H]4C)cn3)ncn2)ccc1[C@@H](C)NC(=O)c1nc(C(C)(C)C)no1]

or a pharmaceutically acceptable salt thereof.

2. A compound, which is a pharmaceutically acceptable salt of

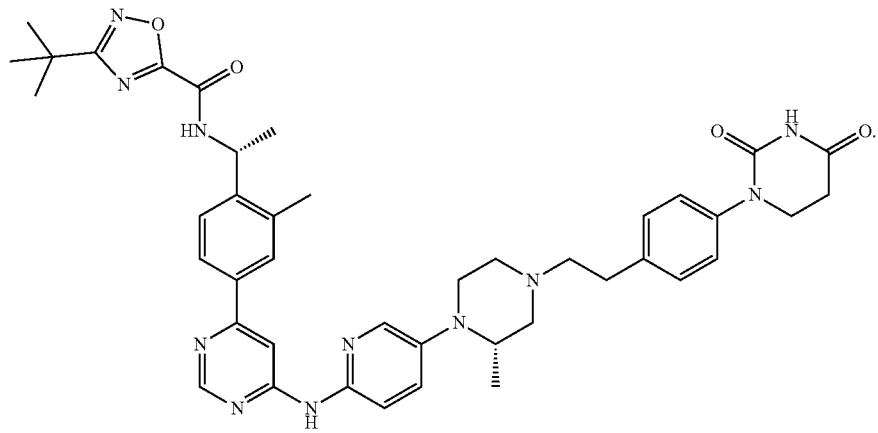 [SMILES: Cc1cc(-c2cc(Nc3ccc(N4CCN(CCc5ccc(N6CCC(=O)NC6=O)cc5)C[C@@H]4C)cn3)ncn2)ccc1[C@@H](C)NC(=O)c1nc(C(C)(C)C)no1]

3. A compound which is

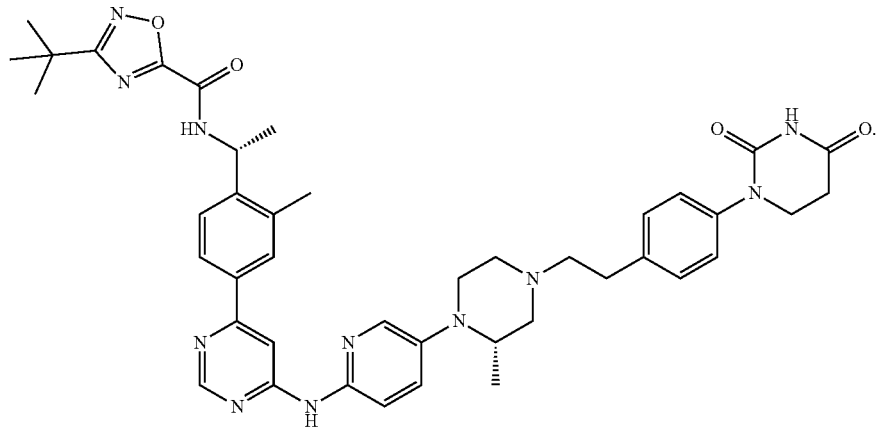 [SMILES: Cc1cc(-c2cc(Nc3ccc(N4CCN(CCc5ccc(N6CCC(=O)NC6=O)cc5)C[C@@H]4C)cn3)ncn2)ccc1[C@@H](C)NC(=O)c1nc(C(C)(C)C)no1]

UNITED STATES PATENT AND TRADEMARK OFFICE
CERTIFICATE OF CORRECTION

PATENT NO. : 12,172,992 B2  
APPLICATION NO. : 18/187489  
DATED : December 24, 2024  
INVENTOR(S) : Zhiguo Bian et al.

Page 1 of 5

It is certified that error appears in the above-identified patent and that said Letters Patent is hereby corrected as shown below:

On the Title Page

In Column 2, item (57), under ABSTRACT, below Structure (I), Line 1, delete "$R^{4A}$," and insert -- $R^{4a}$, --, therefor.

On page 2, in Column 2, item (56), under OTHER PUBLICATIONS, Line 4, delete "2018 ," and insert -- 2018, --, therefor.

On page 3, in Column 1, item (56), under OTHER PUBLICATIONS, Line 28, delete "( E2-2)" and insert -- (E2-2) --, therefor.

On page 3, in Column 1, item (56), under OTHER PUBLICATIONS, Line 36, delete "2018 ," and insert -- 2018, --, therefor.

On page 3, in Column 2, item (56), under OTHER PUBLICATIONS, Line 55, delete "Molecules :" and insert -- Molecules: --, therefor.

On page 4, in Column 1, item (56), under OTHER PUBLICATIONS, Line 5, delete "Wang.," and insert -- Wang --, therefor.

On page 4, in Column 2, item (56), under OTHER PUBLICATIONS, Line 16, delete "BTK, "Abstracts" and insert -- BTK," Abstracts --, therefor.

On page 4, in Column 2, item (56), under OTHER PUBLICATIONS, Line 18, delete "BTK ," and insert -- BTK, --, therefor.

On page 4, in Column 2, item (56), under OTHER PUBLICATIONS, Line 19, delete "Malignancies. "Blood:" and insert -- Malignancies." Blood: --, therefor.

Signed and Sealed this  
Thirtieth Day of December, 2025

John A. Squires  
*Director of the United States Patent and Trademark Office*

In the Specification

In Columns 5-6, delete

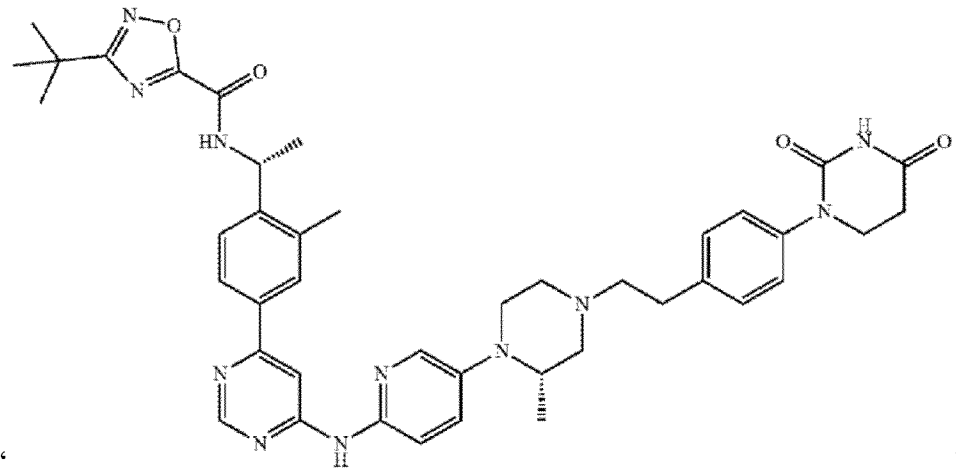

" and insert

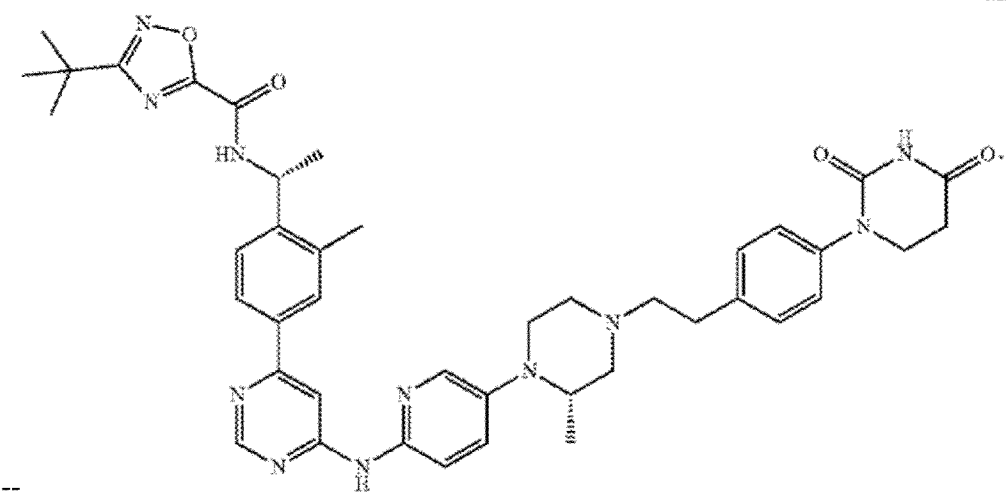

--, therefor.

In Column 9, Line 28, delete "C₄₈₁" and insert -- C481 --, therefor.

In Column 13, Line 19, delete "Hartwing" and insert -- Hartwig --, therefor.

In Column 15, Lines 43-44, delete "4,6-dicholopyrimidine" and insert -- 4,6-dichloropyrimidine --, therefor.

In Column 16, Line 40, delete "Hartwing" and insert -- Hartwig --, therefor.

In Column 32, Line 15, delete "(S)—N—((R)" and insert -- (S)-N-((R) --, therefor.

In Column 32, Line 39, delete "N—((R)" and insert -- N-((R) --, therefor.

In Column 34, Line 6, delete "mol))" and insert -- mol) --, therefor.

CERTIFICATE OF CORRECTION (continued)
U.S. Pat. No. 12,172,992 B2

In Column 34, Line 18, delete "1l" and insert -- 1I --, therefor.

In Column 35, Lines 54-55, delete "palladium(II) palladium(II)" and insert -- palladium(II) --, therefor.

In Column 35, Line 67, delete "miz" and insert -- m/z --, therefor.

In Column 36, Line 51, delete "1H)" and insert -- 1H), --, therefor.

In Column 36, Line 52, delete "1H)" and insert -- 1H), --, therefor.

In Column 36, Line 52, delete "1H)" and insert -- 1H), --, therefor.

In Column 36, Line 66, delete "10" and insert -- 1O --, therefor.

In Column 37, Line 52, delete "2H)" and insert -- 2H), --, therefor.

In Column 38, Line 11, delete "N—((R)" and insert -- N-((R) --, therefor.

In Column 39, Line 39, delete "10," and insert -- 1O, --, therefor.

In Column 39, Line 59, delete "10." and insert -- 1O. --, therefor.

In Column 39, Line 61, delete "2H)" and insert -- 2H), --, therefor.

In Column 39, Line 67, delete "miz" and insert -- m/z --, therefor.

In Column 42, Line 15, delete "10" and insert -- 1O --, therefor.

In Column 43, Line 2, delete "(ESP):" and insert -- (ESI$^+$): --, therefor.

In Column 43, Line 30, delete "(ESP):" and insert -- (ESI$^+$): --, therefor.

In Column 43, Line 50, delete "(ESP):" and insert -- (ESI$^+$): --, therefor.

In Column 45, Line 55, delete "(EST):" and insert -- (ESI$^+$): --, therefor.

In Column 46, Line 14, delete "N—((R)" and insert -- N-((R) --, therefor.

In Column 46, Line 47, delete "{{5" and insert -- {[5 --, therefor.

In Column 48, Line 24, delete "changed" and insert -- charged --, therefor.

CERTIFICATE OF CORRECTION (continued)
U.S. Pat. No. 12,172,992 B2

In Column 49, Line 14, delete "(S)—N—((R)" and insert -- (S)-N-((R) --, therefor.

In Column 49, Line 37, delete "(S)—N—((R)" and insert -- (S)-N-((R) --, therefor.

In Column 51, Line 12, delete "N—((R)" and insert -- N-((R) --, therefor.

In Column 53, Line 16, delete "iPrMgC$_1$" and insert -- iPrMgCl --, therefor.

In Column 53, Line 51, delete "(S)—N—((R)" and insert -- (S)-N-((R) --, therefor.

In Column 54, Line 3, delete "(S)—N—((R)" and insert -- (S)-N-((R) --, therefor.

In Column 55, Line 46, delete "2H)" and insert -- 2H), --, therefor.

In Column 57, Line 61, delete "(S)—N—((R)" and insert -- (S)-N-((R) --, therefor.

In Column 58, Line 16, delete "(S)—N—((R)" and insert -- (S)-N-((R) --, therefor.

In Column 62, Line 49, delete "N—((R)" and insert -- N-((R) --, therefor.

In Column 62, Line 57, delete "reduced" and insert -- reduced pressure --, therefor.

In Column 63, Line 61, delete "(S)—N—((R)" and insert -- (S)-N-((R) --, therefor.

In Column 64, Line 18, delete "(S)—N—((R)" and insert -- (S)-N-((R) --, therefor.

In Column 67, Line 3, delete "(S)—N—((R)" and insert -- (S)-N-((R) --, therefor.

In Column 69, Line 33, delete "17J" and insert -- 17I --, therefor.

In Column 70, Line 21, delete "100)];" and insert -- 100))]; --, therefor.

In Column 70, Line 26, delete "CA)." and insert -- CA. --, therefor.

In Column 71, Lines 31-32, delete "an Labcyte" and insert -- a Labcyte --, therefor.

In Column 71, Line 53, delete "MSD ELISA Based" and insert -- MSD ELISA-Based --, therefor.

In Column 71, Line 66, delete "(Tecan))," and insert -- (Tecan), --, therefor.

In Column 72, Line 18, delete "antibody," and insert -- antibody --, therefor.

In Column 72, Line 26, delete "experiments." and insert -- experiments --, therefor.

CERTIFICATE OF CORRECTION (continued)
U.S. Pat. No. 12,172,992 B2

In Column 72, Line 29, delete "column" and insert -- column. --, therefor.

In Column 72, Line 36, delete "$C_{57}BL/6J$" and insert -- C57BL/6J --, therefor.

In Column 73, Line 7, delete "(30011.1)" and insert -- (300 μl) --, therefor.

In Column 74, Line 29, delete "EIA" and insert -- Eμ --, therefor.

In Column 74, Line 34, delete "$C_{57}BL/6J$" and insert -- C57BL/6J --, therefor.

In Column 74, Line 53, delete "$C_{57}BL/6J$" and insert -- C57BL/6J --, therefor.

In Column 75, Line 11, delete "$and_{60}$ %" and insert -- and 60% --, therefor.

In Column 75, Line 12, delete "$and_{60}$ %" and insert -- and 60% --, therefor.